IMAGE

United States Patent [19]
Scadden et al.

[11] Patent Number: 6,087,144
[45] Date of Patent: Jul. 11, 2000

[54] PROTEIN TYROSINE KINASES

[75] Inventors: David T. Scadden, Weston, Mass.; Kevin P. Baker, Millbrae; Will F. Baron, Brisbane, both of Calif.

[73] Assignee: Genentech, Inc., South San Francisco, Calif.

[21] Appl. No.: 08/447,314

[22] Filed: May 22, 1995

Related U.S. Application Data

[62] Division of application No. 08/170,558, Dec. 20, 1993, which is a continuation of application No. 08/157,563, Nov. 23, 1993, abandoned.

[51] Int. Cl.$^7$ .................................................. C07K 14/705
[52] U.S. Cl. ................... 435/194; 435/69.1; 530/350; 530/395; 514/2
[58] Field of Search ............................ 435/69.1, 194; 530/350, 395; 514/2

[56] References Cited

U.S. PATENT DOCUMENTS 5,185,438  2/1993  Lemischke .......................... 536/23.2

FOREIGN PATENT DOCUMENTS

| 455460 | 11/1991 | European Pat. Off. . |
| 519869 | 12/1992 | European Pat. Off. . |
| WO 92/13948 | 8/1992 | WIPO . |
| WO 92/14748 | 9/1992 | WIPO . |
| WO 93/00425 | 1/1993 | WIPO . |
| WO 93/14124 | 7/1993 | WIPO . |
| WO 93/15201 | 8/1993 | WIPO . |
| WO 93/23429 | 11/1993 | WIPO . |
| WO 94/19463 | 9/1994 | WIPO . |

OTHER PUBLICATIONS

Stark et al., "FGFR-4, a new member of the fibroblast growth factor receptor family, expressed in the definitive endoderm and skeletal muscle lineages of the mouse" *Development* 113:641–651 (1991).
"Chapter 16: Expression of Cloned Genes in Cultured Mamalian Cells" *Molecular Cloning: A Laboratory Manual*, Sambrook et al., Second edition, Cold Spring Harbor Laboratory Press vol. 3:16.2–16.30 (1989).
"Chapter 16: Expression of Cloned Genes in *Escherichia coli*" *Molecular Cloning: A Laboratory Manual*, Sambrook et al., Second edition, Cold Spring Harbor Laboratory Press vol. 3:17.2–17.28 (1989).
Capon et al., "Designing CD4 Immunoadhesins for AIDS Therapy" *Nature* 337:525–531 (Feb. 9, 1989).
Godowski et al., "Reevaluation of the Roles of Protein S and Gas6 as Ligands for the Receptor Tyrosine Kinase Rse/Tyro3" *Cell* 82:355–358 (Aug. 11, 1995).
Li et al., "Identification of Gas6 as a Growth Factor for Human Schwann Cells" *The Journal of Neuroscience* 16(6):2012–2019 (Mar. 15, 1996).
Paborsky et al., "Mammalian Cell Transient Expression of Tissue Factor for the Production of Antigen" *Protein Eng.* 3(6):547–553 (1990).

Sarup, "Characterization of an Anti–P185$^{her2}$ Monoclonal Antibody that Stimulates Receptor Function and Inhibits Tumor Cell Growth" *Growth Regulation* 1(2):73–82 (1991).
Taylor et al., "Mouse Mammary Tumors Express Elevated Levels of RNA Encoding the Murine Homolog of SKY, a Putative Receptor Tyrosine Kinase" *The Journal of Biological Chemistry* 270(12):6872–6880 (Mar. 24, 1995).
Aroian et al., "The let–23 Gene Necessary for Caenorhabditis elgans Vulval Induction Encodes a Tyrosine Kinase of the EGF Receptor Subfamily" *Nature* 348:693–699 (1990).
Birchmeier et al., "Characterization of an Activated Human ros Gene" *Molecular & Cellular Biology* 6(9):3109–3116 (1986).
Brauninger et al., "Isolation and Characterization of a Human Gene That Encodes a New Subclass of Protein Tyrosine Kinases" *Gene* 110(2):205–211 (1992).
Dai et al., "Molecular Cloning of a Novel Receptor Tyrosine Kinase, tif, Highly Expressed in Human Ovary and Testis" *Oncogene* 9:975–979 (1994).
Faust et al., "The murine ufo receptor: molecular cloning, chromosomal localization and in situ expression analysis" *Oncogene* 7:1287–1293 (1992).
Fujumoto, "brt, A Mouse Gene Encoding a Novel Receptor–Type Protein–Tyrosine Kinase, is Preferentially Expressed in the Brain" *Oncogene* 9:693–698 (1994).
GenBank, "Release 79" (Oct. 15, 1993).
Hanks et al., "The Protein Kinase Family: Conserved Features and Deduced Phylogeny of the Catalytic Domains" *Science* 241:42–52 (1988).
Hao et al., "Isolation and sequence analysis of a novel human tyrosine kinase gene" *Molecular & Cellular Biology* 9(4):1587–1593 (1989).
Hart et al, "Extracellular Domain of the Boss Transmembrane Ligand Acts as an Antagonist of the Sev Receptor" *Nature* 361:732–736 (1993).
Holtrich et al., "Two additional protein–tyrosine kinases expressed in human lung: Fourth member of the fibroblast growth factor receptor family and an intracellular protein–tyrosine" *Proc. Natl. Acad. Sci.* 88:10411–10415 (1991).
Janssen et al., "A novel putative tyrosine kinase receptor with oncogenic potential" *Oncogene* 6:2113–2120 (1991).
Johnson et al., "A receptor tyrosine kinase found in breast carcinoma cells has an extracellular discoidin I–like domain" *Proc. Natl. Acad. Sci.* 90:5677–5681 (Jun. 15, 1993).
Lai et al., "An Extended Family of Protein–Tyrosine Kinase Genes Differentially Expressed in the Vertebrate Nervous System" *Neuron* 6:691–704 (May 1991).

(List continued on next page.)

*Primary Examiner*—Sally Teng

[57] ABSTRACT

The protein tyrosine kinase receptors, designated Rse and HPTK6, have been purified from human and/or murine cell tissues. Rse and HPTK6 have been cloned from a cDNA library of a human liver carcinoma cell line (i.e., Hep 3B) using PCR amplification. Provided herein are nucleic acid sequences encoding Rse and HPTK6 useful as diagnostics and in the recombinant preparation of Rse and HPTK6. Rse and HPTK6 are used in the preparation and purification of antibodies thereto and in diagnostic assays.

10 Claims, 23 Drawing Sheets

OTHER PUBLICATIONS

Lai et al., "Structure, expression, and activity of Tyro 3, a neural adhesion–related receptor tyrosine kinase" *Oncogene* 9:2567–2578 (1994).

Mark et al., "rse, a Novel Receptor–type Tryosine Kinase with Homology to Axl/Ufo, Is Expressed at High Levels in the Brain" *Journal of Biological Chemistry* 269(14):10720–10728 (Apr. 8, 1994).

Martin–Zanca et al., "Molecular and Biochemical Characterization of the Human trk Proto–Oncogene" *Molecular & Cellular Biology* 9(1):24–33 (Jan. 1989).

Matthews et al., "A receptor tyrosine kinase cDNA isolated from a population of enriched primitive hematopoietic cells and exhibiting close genetic linkage to c–kit" *Proc. Natl. Acad. Sci.* 88:9026–9030 (1991).

Matthews et al., "A receptor tyrosine kinase specific to hematopoietic stem and progenitor cell–enriched populations" *Cell* 65:1143–1152 (1991).

O'Bryan et al., "axl, a transforming gene isolated from primary human myeloid leukemia cells, encodes a novel receptor tyrosine kinase" *Molecular & Cellular Biology* 11:5016–5031 (1991).

Ohashi et al., "Cloning of the cDNA for a Novel Receptor Tyrosine Kinase, Sky, Predominantly Expressed in Brain" *Oncogene* 9:699–705 (1994).

Park et al., "Sequence of Met Protooncogene cDNA has Features Characteristic of the Tyrosine Kinase Family of Growth–Factor Receptors" *Proc. Natl. Acad. Sci. USA* 84:6379–6383 (1987).

Partanen et al., "Putative tryosine kinases expressed in K–562 human leukemia cells" *Proc. Natl. Acad. Sci.* 87:8913–8917 (1990).

Pazin et al., "Triggering Signaling Cascades by Receptor Tyrosine Kinases" *TIBS* 17:374–378 (1992).

Polvi et al., "The Human TYRO3 Gene and Pseudogene are Located in Chromosome 15q14–q25" *Gene* 134:289–293 (1993).

Pulido et al., "Etrk, a Drosophilia Gene Related to the trk Family of Neurotrophin Receptors, Encodes a Novel Class of Neural Cell Adhesion Molecule" *EMBO Journal* 11(2):391–404 (1992).

Rescigno et al., "A putative receptor tyrosine kinase with unique structural topology" *Oncogene* 6:1909–1913 (1991).

Schlessinger et al., "Growth factor signaling by receptor tyrosine kinases" *Neuron* 9:383–391 (1992).

Ullrich et al., "Human Insulin Receptor and Its Relationship to the Tyrosine Kinase Family of Oncogenes" *Nature* 313:756–761 (1985).

Ullrich et al., "Insulin–like growth factor I receptor primary structure: comparison with insulin receptor suggests structural determinants that define functional specificity" *EMBO Journal* 5(10):2503–2512 (1986).

Ullrich et al., "Signal transduction by receptors with tyrosine kinase activity" *Cell* 61:203–212 (1990).

Wilks et al., "The application of the polymerase chain reaction to cloning members of the protein tyrosine kinase family" *Gene* 85:67–74 (1989).

Yarden, "Angonistic Antibodies Stimulate the Kinase Encoded by the neu Protooncogene in Living Cells but the Oncogenic Mutant is Constitutively Active" *Proc. Natl. Acad. Sci. USA* 87:2569–2573 (1990).

Zerlin et al., "NEP:a novel receptor–like tyrosine kinase expressed in proliferating neuroepithelia" *Oncogene* 8(10):2731–2739 (Oct. 1993).

Duan et al., J. of Biol. Chem., vol. 266, pp. 413–418, 1991.

```
748                M  E  E     V  Y  D     L  M  Y  Q     C  W  S     A  D  P     K  Q  R  P     S  F  T     C  L  R     M  E  L  E     N  I  L
2301   GCATGGAGGA AGTGTATGAT CTCATGTACC AGTGCTGGAG CGCCGACCCC AAGCAGCGCC CAAGCTTCAC GTGTCTGCGA ATGGAACTGG AGAACATTCT

781     G  H  L     S  V  L  S     T  S  Q     D  P  L           Y  I  N  I     E  R  A           E  Q  P     T  E  S  G     S  P  E     L  H  C
2401   GGGCCACCTG TCTGTGCTGT CCACCAGCCA GGACCCCTTG TACATCAACA TTGAGAGAGC TGAGCAGCCT ACTGAGAGTG GCAGCCCTGA GCTGCACTGT

814     G  E  R  S     S  S  E     A  G  D     G  S  G  V     G  A  V     G  G  I     P  S  D  S     R  Y  I     F  S  P     G  G  L  S
2501   GGAGAGCGAT CCAGCAGCGA GGCAGGGGAC GGCAGTGGCG TGGGGGCAGT AGTGGCATC CCCAGTGACT CTCGGTACAT CTTCAGCCCC GGAGGGCTAT

848    E  S  P     G  Q  L          E  Q  Q  P     E  S  P           L  N  E     N  Q  R  L           L  L  L     Q  Q     L  L  P  H     S  S  C
2601   GAGTCACC AGGGCAGCTG GAGCAGCAGC CAGAAAGCCC CCTCAATGAG AACCAGAGGC TGTTGTTGCT GCAGCAAGGG CTACTGCCTC ACAGTAGCTG

881    O
2701   TTAACCCTCA GGCAGAGGAA AGTTGGGGCC CCTGGCTCTG CTGACGCGCTG CGCTGCCTGA CTAGGCCCAG TCTGATCACA GCCCAGGCAG CAAGGTATGG

2801   AGGCTCCTGT GGTAGCCCTC CCAAGCTGTG TGGCCGCCTG ACGGACCAAA TTGCCCAATC CCAGTTCTTC CTGCAGCCGC TCTGGCCAGC CTGGCATCAG

2901   TTTCAGGCCTT GGCTTAGAGG AGTGAGCCA GAGCTGGTTG CCTGAATGCA AGGAGGGGAG GGTGGCTATG TTTCCATGGG TTGGAGCCGC CTGCAGCCTG

3001   GTGGATGGCA GTAAGGGAGG GTAGCAACAG CACTTGGGCC CCTGTGGGCC CCTACCCTCC TGGCTGAGCT TAGTGCATGC AAAGAGATGT CCATGTATTG TTCCCTTTTA GGTGATGATT

3101   GAACTCAGCA CTGCCCACCA GGGTCCCTAA GCCCTATGGC GAAATGCCAG GCCCTATGGC AGGAAATGGT GGATATTCT CAGGTCTGAA TCCTCATCAT CTTCCTGATT CCCCACCCTG

3201   AGGAAGGGAT TGGCACACTT GGGTCCCTAA TGGGGCTCTG ACGCATGCTG AAGGACAAAA GGTTACAGAG ATCCGACTTC AAAAGGCAGG GTCTGAGTCT GGCAGGTGGA

3301   CAAAGGCCTG GAACTGGCTG TGGGGCTGCC CAGGAGTCAG GCATTTCAGG ACCCCTCCAA GCTTCTACAG TCTGTCTGAG CATGCTACCA AGCCCCCAGA TACCCAAAA

3401   GAGGTGCTAA GGGGCTGGCC CAGGAGTCAG CCTCCCAGC GATGACCCTT AGTCTACCC TCCTCTCTAA ATGGACATCC TCGTTTGTCC CAAGTCTCCA

3501   CTAACAGAGG CAGTTTTGTC TGAGCCCAGC CCTCCCACAT GATGACCCTT AGTCTACCC TCCTCTCTAA ATGGACATCC TCGTTTGTCC CAAGTCTCCA

3601   GAGAGACTAC TGATGGCTAA AAAAGTTCCA GGAACCAGGG CTGGGGTGGA ACCAGGCTG GAACCAGGG ACCAGGCTG GGTCGAGGC AGGCTCTTGG GCAGGCTCTT

3701   GCTGTTAGGA ACATTTCTAA TGTGGGTAAG GCTATTAAGT TGCTGTTCA AAACAAATAA AATTGAAACA TAAAGAATCA AAAAAAAAAA AAAAA
```

FIG. 1F

```
  1 GAATTCTCGA GTCGACGTTG GACTTGAAGG AATGCCAAGA GATGCTGCCC

51 CCACCCCCTT AGGCCCGAGG GATCAGGAGC TATGGGACCA GAGGCCCTGT
  1                                            MetGlyPro GluAlaLeuSer
                                                         * * * * * *

101 CATCTTTACT GCTGCTGCTC TTGGTGGCAA GTGGAGATGC TGACATGAAG
  8    SerLeuLe uLeuLeuLeu LeuValAlaS erGlyAspAl aAspMetLys
       * * * * * * * *  * * * * * * * * * *  * * * * * * * * * *  * * * *

151 GGACATTTTG ATCCTGCCAA GTGCCGCTAT GCCCTGGGCA TGCAGGACCG
 24   GlyHisPheA spProAlaLy sCysArgTyr AlaLeuGlyM etGlnAspArg

201 GACCATCCCA GACAGTGACA TCTCTGCTTC CAGCTCCTGG TCAGATTCCA
 41    ThrIlePro AspSerAspI leSerAlaSe rSerSerTrp SerAspSerThr

251 CTGCCGCCCG CCACAGCAGG TTGGAGAGCA GTGACGGGGA TGGGGCCTGG
 58    AlaAlaAr gHisSerArg LeuGluSerS erAspGlyAs pGlyAlaTrp

301 TGCCCCGCAG GGTCGGTGTT TCCCAAGGAG GAGGAGTACT TGCAGGTGGA
 74   CysProAlaG lySerValPh eProLysGlu GluGluTyrL euGlnValAsp

351 TCTACAACGA CTGCACCTGG TGGCTCTGGT GGGCACCCAG GGACGGCATG
 91    LeuGlnArg LeuHisLeuV alAlaLeuVa lGlyThrGln GlyArgHisAla

401 CCGGGGGCCT GGGCAAGGAG TTCTCCCGGA GCTACCGGCT GCGTTACTCC
108     GlyGlyLe uGlyLysGlu PheSerArgS erTyrArgLe uArgTyrSer

451 CGGGATGGTC GCCGCTGGAT GGGCTGGAAG GACCGCTGGG GTCAGGAGGT
124   ArgAspGlyA rgArgTrpMe tGlyTrpLys AspArgTrpG lyGlnGluVal

501 GATCTCAGGC AATGAGGACC CTGAGGGAGT GGTGCTGAAG GACCTTGGGC
141    IleSerGly AsnGluAspP roGluGlyVa lValLeuLys AspLeuGlyPro

551 CCCCCATGGT TGCCCGACTG GTTCGCTTCT ACCCCCGGGC TGACCGGGTC
158    ProMetVa lAlaArgLeu ValArgPheT yrProArgAl aAspArgVal

601 ATGAGCGTCT GTCTGCGGGT AGAGCTCTAT GGCTGCCTCT GGAGGGATGG
174   MetSerValC ysLeuArgVa lGluLeuTyr GlyCysLeuT rpArgAspGly

651 ACTCCTGTCT TACACCGCCC CTGTGGGGCA GACAATGTAT TTATCTGAGG
191    LeuLeuSer TyrThrAlaP roValGlyGl nThrMetTyr LeuSerGluAla

701 CCGTGTACCT CAACGACTCC ACCTATGACG GACATACCGT GGGCGGACTG
208    ValTyrLe uAsnAspSer ThrTyrAspG lyHisThrVa lGlyGlyLeu

751 CAGTATGGGG GTCTGGGCCA GCTGGCAGAT GGTGTGGTGG GGCTGGATGA
224   GlnTyrGlyG lyLeuGlyGl nLeuAlaAsp GlyValValG lyLeuAspAsp

801 CTTTAGGAAG AGTCAGGAGC TGCGGGTCTG GCCAGGCTAT GACTATGTGG
241    PheArgLys SerGlnGluL euArgValTr pProGlyTyr AspTyrValGly

851 GATGGAGCAA CCACAGCTTC TCCAGTGGCT ATGTGGAGAT GGAGTTTGAG
258    TrpSerAs nHisSerPhe SerSerGlyT yrValGluMe tGluPheGlu
```

FIG. 2A

```
 901 TTTGACCGGC TGAGGGCCTT CCAGGCTATG CAGGTCCACT GTAACAACAT
 274 PheAspArgL euArgAlaPh eGlnAlaMet GlnValHisC ysAsnAsnMet

951 GCACACGCTG GGAGCCCGTC TGCCTGGCGG GGTGGAATGT CGCTTCCGGC
 291  HisThrLeu GlyAlaArgL euProGlyGl yValGluCys ArgPheArgArg

1001 GTGGCCCTGC CATGGCCTGG GAGGGGAGC CCATGCGCCA CAACCTAGGG
 308   GlyProAl aMetAlaTrp GluGlyGluP roMetArgHi sAsnLeuGly

1051 GGCAACCTGG GGGACCCCAG AGCCCGGGCT GTCTCAGTGC CCCTTGGCGG
 324 GlyAsnLeuG lyAspProAr gAlaArgAla ValSerValP roLeuGlyGly

1101 CCGTGTGGCT CGCTTTCTGC AGTGCCGCTT CCTCTTTGCG GGGCCCTGGT
 341  ArgValAla ArgPheLeuG lnCysArgPh eLeuPheAla GlyProTrpLeu

1151 TACTCTTCAG CGAAATCTCC TTCATCTCTG ATGTGGTGAA CAATTCCTCT
 358   LeuPheSe rGluIleSer PheIleSerA spValValAs nAsnSerSer

1201 CCGGCACTGG GAGGCACCTT CCCGCCAGCC CCTGGTGGC CGCCTGGCCC
 374 ProAlaLeuG lyGlyThrPh eProProAla ProTrpTrpP roProGlyPro

1251 ACCTCCCACC AACTTCAGCA GCTTGGAGCT GGAGCCCAGA GGCCAGCAGC
 391   ProProThr AsnPheSerS erLeuGluLe uGluProArg GlyGlnGlnPro

1301 CCGTGGCCAA GCCCGAGGGG AGCCCGACCG CCATCCTCAT CGGCTGCCTG
 408   ValAlaLy sProGluGly SerProThrA laIleLeuIl eGlyCysLeu

1351 GTGGCCATCA TCCTGCTCCT GCTGCTCATC ATTGCCCTCA TGCTCTGGCG
 424  ValAlaIleI leLeuLeuLe uLeuLeuIle IleAlaLeuM etLeuTrpArg

1401 GCTGCACTGG CGCAGGCTCC TCAGCAAGGC TGAACGGAGG GTGTTGGAAG
 441   LeuHisTrp ArgArgLeuL euSerLysAl aGluArgArg ValLeuGluGlu

1451 AGGAGCTGAC GGTTCACCTC TCTGTCCCTG GGACACTAT CCTCATCAAC
 458   GluLeuTh rValHisLeu SerValProG lyAspThrIl eLeuIleAsn

1501 AACCGCCCAG GTCCTAGAGA GCCACCCCCG TACCAGGAGC CCCGGCCTCG
 474  AsnArgProG lyProArgGl uProProPro TyrGlnGluP roArgProArg

1551 TGGGAATCCG CCCCACTCCG CTCCCTGTGT CCCCAATGGC TCTGCGTTGC
 491   GlyAsnPro ProHisSerA laProCysVa lProAsnGly SerAlaLeuLeu

1601 TGCTCTCCAA TCCAGCCTAC CGCCTCCTTC TGGCCACTTA CGCCCGTCCC
 508   LeuSerAs nProAlaTyr ArgLeuLeuL euAlaThrTy rAlaArgPro

1651 CCTCGAGGCC CGGGCCCCCC CACACCCGCC TGGGCCAAAC CCACCAACAC
 524  ProArgGlyP roGlyProPr oThrProAla TrpAlaLysP roThrAsnThr

1701 CCAGGCCTAC AGTGGGGACT ATATGGAGCC TGAGAAGCCA GGCGCCCCGC
 541   GlnAlaTyr SerGlyAspT yrMetGluPr oGluLysPro GlyAlaProLeu

1751 TTCTGCCCCC ACCTCCCCAG AACAGCGTCC CCATTATGC CGAGGCTGAC
 558   LeuProPr oProProGln AsnSerValP roHisTyrAl aGluAlaAsp
```

FIG. 2B

```
1801 ATTGTTACCC TGCAGGGCGT CACCGGGGGC AACACCTATG CTGTGCCTGC
 574 IleValThrL euGlnGlyVa lThrGlyGly AsnThrTyrA laValProAla

1851 ACTGCCCCCA GGGGCAGTCG GGGATGGGCC CCCCAGAGTG GATTTCCCTC
 591   LeuProPro GlyAlaValG lyAspGlyPr oProArgVal AspPheProArg

1901 GATCTCGACT CCGCTTCAAG GAGAAGCTTG GCGAGGGCCA GTTTGGGGAG
 608   SerArgLe uArgPheLys GluLysLeuG lyGluGlyGl nPheGlyGlu
              << <                   . .......... .......

1951 GTGCACCTGT GTGAGGTCGA CAGCCCTCAA GATCTGGTCA GTCTTGATTT
 624 ValHisLeuC ysGluValAs pSerProGln AspLeuValS erLeuAspPhe

2001 CCCCCTTAAT GTGCGTAAGG GACACCCTTT GCTGGTAGCT GTCAAGATCT
 641   ProLeuAsn ValArgLysG lyHisProLe uLeuValAla ValLysIleLeu

2051 TACGGCCAGA TGCCACCAAG AATGCCAGGA ATGATTTCCT GAAAGAGGTG
 658    ArgProAs pAlaThrLys AsnAlaArgA snAspPheLe uLysGluVal

2101 AAGATCATGT CGAGGCTCAA GGACCCAAAC ATCATTCGGC TGCTGGGCGT
 674  LysIleMetS erArgLeuLy sAspProAsn IleIleArgL euLeuGlyVal

2151 GTGTGTGCAG GACGACCCCC TCTGCATGAT TACTGACTAC ATGGAGAACG
 691   CysValGln AspAspProL euCysMetIl eThrAspTyr MetGluAsnGly

2201 GCGACCTCAA CCAGTTCCTC AGTGCCCACC AGCTGGAGGA CAAGGCAGCC
 708    AspLeuAs nGlnPheLeu SerAlaHisG lnLeuGluAs pLysAlaAla

2251 GAGGGGGCCC CTGGGGACGG GCAGGCTGCG CAGGGGCCCA CCATCAGCTA
 724  GluGlyAlaP roGlyAspGl yGlnAlaAla GlnGlyProT hrIleSerTyr

2301 CCCAATGCTG CTGCATGTGG CAGCCCAGAT CGCCTCCGGC ATGCGCTATC
 741   ProMetLeu LeuHisValA laAlaGlnIl eAlaSerGly MetArgTyrLeu

2351 TGGCCACACT CAACTTTGTA CATCGGGACC TGGCCACGCG GAACTGCCTA
 758    AlaThrLe uAsnPheVal HisArgAspL euAlaThrAr gAsnCysLeu

2401 GTTGGGGAAA ATTTCACCAT CAAAATCGCA GACTTTGGCA TGAGCCGGAA
 774  ValGlyGluA snPheThrIl eLysIleAla AspPheGlyM etSerArgAsn

2451 CCTCTATGCT GGGGACTATT ACCGTGTGCA GGGCCGGGCA GTGCTGCCCA
 791    LeuTyrAla GlyAspTyrT yrArgValGl nGlyArgAla ValLeuProIle

2501 TCCGCTGGAT GGCCTGGGAG TGCATCCTCA TGGGGAAGTT CACGACTGCG
 808    ArgTrpMe tAlaTrpGlu CysIleLeuM etGlyLysPh eThrThrAla

2551 AGTGACGTGT GGGCCTTTGG TGTGACCCTG TGGGAGGTGC TGATGCTCTG
 824   SerAspValT rpAlaPheGl yValThrLeu TrpGluValL euMetLeuCys

2601 TAGGGCCCAG CCCTTTGGGC AGCTCACCGA CGAGCAGGTC ATCGAGAACG
 841   ArgAlaGln ProPheGlyG lnLeuThrAs pGluGlnVal IleGluAsnAla
```

FIG. 2C

2651 CGGGGGAGTT CTTCCGGGAC CAGGGCCGGC AGGTGTACCT GTCCCGGCCG
 858    GlyGluPh ePheArgAsp GlnGlyArgG lnValTyrLe uSerArgPro

2701 CCTGCCTGCC CGCAGGGCCT ATATGAGCTG ATGCTTCGGT GCTGGAGCCG
 874    ProAlaCysP roGlnGlyLe uTyrGluLeu MetLeuArgC ysTrpSerArg

2751 GGAGTCTGAG CAGCGACCAC CCTTTTCCCA GCTGCATCGG TTCCTGGCAG
 891    GluSerGlu GlnArgProP roPheSerGl nLeuHisArg PheLeuAlaGlu
                                                            >>>

2801 AGGATGCACT CAACACGGTG TGAATCACAC ATCCAGCTGC CCCTCCCTCA
 908    AspAlaLe uAsnThrVal

2851 GGGAGTGATC CAGGGGAAGC CAGTGACACT AAAACAAGAG GACACAATGG

2901 CACCTCTGCC CTTCCCCTCC CGACAGCCCA TCACCTCTAA TAGAGGCAGT

2951 GAGACTGCAG AAGCCCTGT CGCCCACCCA GCTGGTCCTG TGGATGGGAT

3001 CCTCTCCACC CTCCTCTAGC CATCCCTTGG GGAAGGGTGG GGAGAAATAT

3051 AGGATAGACA CTGGACATGG CCCATTGGAG CACCTGGGCC CCACTGGACA

3101 ACACTGATTC CTGGAGAGGT GGCTGCGCCC CCAGCTTCTC TCTCCCTGTC

3151 ACACACTGGA CCCCACTGGC TGAGAATCTG GGGGTGAGGA GGACAAGAAG

3201 GAGAGGAAAA TGTTTCCTTG TGCCTGCTCC TGTACTTGTC CTCAGCTTGG

3251 GCTTCTTCCT CCTCCATCAC CTGAAACACT GGACCTGGGG GTAGCCCCGC

3301 CCCAGCCCTC AGTCACCCCC ACTTCCCACC TGCAGTCTTG TAGCTAGAAC

3351 TTCTCTAAGC CTATACGTTT CTGTGGAGTA AATATTGGGA TTGGGGGGAA

3401 AGAGGGAGCA ACGGCCCATA GCCTTGGGGT TGGACATCTC TAGTGTAGCT

3451 GCCACATTGA TTTTTCTATA ATCACTTGGG GTTTGTACAT TTTTGGGGGG

3501 AGAGACACAG ATTTTTACAC TAATATATGG ACCTAGCTTG AGGCAATTTT

3551 AATCCCCTGC ACTAGGCAGG TAATAATAAA GGTTGAGTTT TCCACAAAAA

3601 AAAAAAAAAA AAAAAAAAAA AAAAAAAAAA AAAAAA

| | | III | | | | | | | | | IV | | | | | | | V | | | | | | | | | |
|---|---|---|---|---|---|---|---|---|---|---|---|---|---|---|---|---|---|---|---|---|---|---|---|---|---|---|---|
| hRSE | 565 | F | L | R | E | A | A | C | M | K | E | F | D | H | P | H | V | A | K | L | V | G | V | S | L | R | S | R | A | K | G | R | L | P | I | P | M | V | I | L | P | F | M | K | H | G | D | L | H | A | F |
| mRSE | 555 | F | L | R | E | A | A | C | M | K | E | F | D | H | P | H | V | A | K | L | V | G | V | S | L | R | S | R | A | K | G | R | L | P | I | P | M | V | I | L | P | F | M | K | H | G | D | L | H | A | F |
| hAXL | 582 | F | L | S | E | A | V | C | M | K | E | F | D | H | P | N | V | M | R | L | I | G | V | C | F | Q | G | S | E | R | E | S | F | P | A | P | V | V | I | L | P | F | M | K | H | G | D | L | H | S | F |
| mAXL | 576 | F | L | S | E | A | V | C | M | K | E | F | D | H | P | N | V | M | R | L | I | G | V | C | F | Q | G | S | D | R | E | G | F | P | E | P | V | V | I | L | P | F | M | K | H | G | D | L | H | S | F |

| | | | | | | | | | VIa | | | | | | | | | | | | | VIb | | | | | | | | | | |
|---|---|---|---|---|---|---|---|---|---|---|---|---|---|---|---|---|---|---|---|---|---|---|---|---|---|---|---|---|---|---|---|---|---|
| hRSE | 615 | L | L | A | S | R | I | G | E | N | P | F | N | L | P | L | Q | T | L | I | R | F | M | V | D | I | A | C | G | M | E | Y | L | S | S | R | N | F | I | H | R | D | L | A | A | R | N | C | M | L | A |
| mRSE | 605 | L | L | A | S | R | I | G | E | N | P | F | N | L | P | L | Q | T | L | V | R | F | M | V | D | I | A | C | G | M | E | Y | L | S | S | R | N | F | I | H | R | D | L | A | A | R | N | C | M | L | A |
| hAXL | 632 | L | L | Y | S | R | L | G | D | Q | P | V | Y | L | P | T | Q | M | L | V | K | F | M | A | D | I | A | S | G | M | E | Y | L | S | T | K | R | F | I | H | R | D | L | A | A | R | N | C | M | L | N |
| mAXL | 626 | L | L | Y | S | R | L | G | D | Q | P | V | F | L | P | T | Q | M | L | V | K | F | M | A | D | I | A | S | G | M | E | Y | L | S | T | K | R | F | I | H | R | D | L | A | A | R | N | C | M | L | N |

| | | VII | | | | | | | | | | | | | | | | VIII | | | | | | | | | | | | |
|---|---|---|---|---|---|---|---|---|---|---|---|---|---|---|---|---|---|---|---|---|---|---|---|---|---|---|---|---|---|---|---|
| hRSE | 665 | E | D | M | T | V | C | V | A | D | F | G | L | S | R | K | I | Y | S | G | D | Y | Y | R | Q | G | C | A | S | K | L | P | V | K | W | L | A | L | E | S | L | A | D | N | L | Y | T | V | Q | S | D |
| mRSE | 655 | E | D | M | T | V | C | V | A | D | F | G | L | S | R | K | I | Y | S | G | D | Y | Y | R | Q | G | C | A | S | K | L | P | V | K | W | L | A | L | E | S | L | A | D | N | L | Y | T | V | H | S | D |
| hAXL | 682 | E | N | M | S | V | C | V | A | D | F | G | L | S | K | K | I | Y | N | G | D | Y | Y | R | Q | G | R | I | A | K | M | P | V | K | W | I | A | I | E | S | L | A | D | R | V | Y | T | S | K | S | D |
| mAXL | 676 | E | N | M | S | V | C | V | A | D | F | G | L | S | K | K | I | Y | N | G | D | Y | Y | R | Q | G | R | I | A | K | M | P | V | K | W | I | A | I | E | S | L | A | D | R | V | Y | T | S | K | S | D |

| | | IX | | | | | | | | | | | | | | | | | X | | | | | | | | | | |
|---|---|---|---|---|---|---|---|---|---|---|---|---|---|---|---|---|---|---|---|---|---|---|---|---|---|---|---|---|---|
| hRSE | 715 | V | W | A | F | G | V | T | M | W | E | I | M | T | R | G | Q | T | P | Y | A | G | I | E | N | A | E | I | Y | N | Y | L | I | G | G | N | R | L | K | Q | P | P | E | C | M | E | D | Y | Y | D | L |
| mRSE | 705 | V | W | A | F | G | V | T | M | W | E | I | M | T | R | G | Q | T | P | Y | A | G | I | E | N | A | E | I | Y | N | Y | L | I | G | G | N | R | L | K | Q | P | P | E | C | M | E | E | Y | Y | D | L |
| hAXL | 732 | V | W | S | F | G | V | T | M | W | E | I | A | T | R | G | Q | T | P | Y | P | G | V | E | N | S | E | I | Y | D | Y | L | R | Q | G | N | R | L | K | Q | P | A | D | C | L | D | G | L | Y | A | L |
| mAXL | 726 | V | W | S | F | G | V | T | M | W | E | I | A | T | R | G | Q | T | P | Y | P | G | V | E | N | S | E | I | Y | D | Y | L | R | Q | G | N | R | L | K | Q | P | V | D | F | L | D | G | L | Y | S | L |

FIG. 4E

```
                                                                          XI
hRSE  765  M Y Q C W S A D P K Q R P S F T C L R M E L E N I L G Q L S V L S A S Q D P L Y I N I E R A E E P T
mRSE  755  M Y Q C W S A D P K Q R P S F T C L R M E L E N I L G H L S V L S T S Q D P L Y I N I E R A E Q P T
hAXL  782  M S R C W E L N P Q D R P S F T E L R E D L E N T L K A L P P A Q E P D E I L Y V N M D E G G Y P
mAXL  776  M S R C W E L N P R D R P S F A E L R E D L E N T L K A L P P A Q E P D E I L Y V N M D E G G S H L hRSE  815  A G G S L E L P G R D Q P Y S G A G D G S G M G A V G G T P S D C R Y I L T P G G L A E Q P G Q A E
mRSE  805  E S G S P E L H C G E R S S E A G D D G S G V G A V G G I P S D R Y I F S P G G L S E S P G Q L E
hAXL  832  E P P G A A G G A D D P P T Q P D D P S C S C L T A A A E V H P A G R Y V L C P S T - T P S P A Q P A
mAXL  826  E P R G A A G G A D D P P T Q P D D P K D S C S C L T A A A D V H S A G R Y V L C P S T - A P G P T L S A hRSE  865  H Q P E S P L N E T Q R L L L L Q Q G L L P H S S C
mRSE  855  Q Q P E S P L N E N Q R L L L L Q Q G L L P H S S C
hAXL  881  - D R G P A A P G Q - - - - - - E D G A - - - - - - - -
mAXL  875  - D R G C P A P P G Q - - - - - - E D G A - - - - - - - -
```

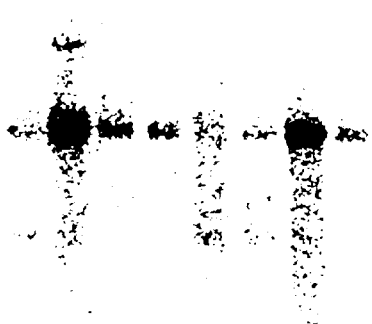
FIG. 7A
— actin FIG. 7B
FIG. 8A
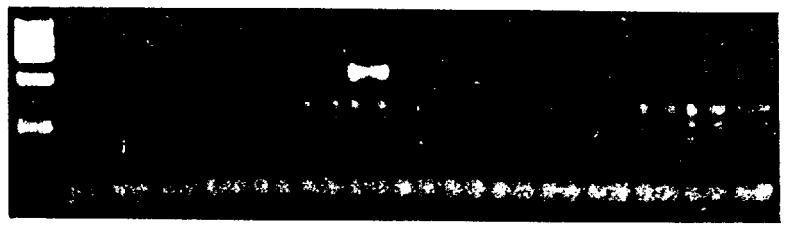
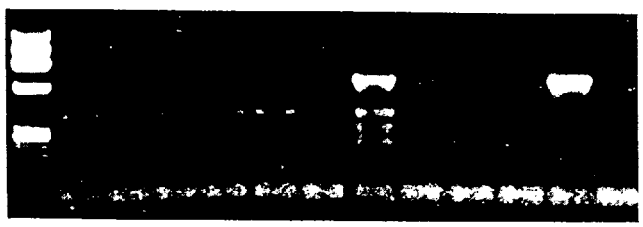

FIG. 8B

| LANE # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| CELL LINE | 212 | 324 | 423 | 507 | 683 | 734 | 750 | 756 | 803 | 811 | 852 | 860 | 862 | 867 | 904 | 909 | 937 | 940 | 967 | 968 | 983 | 1006 | 1049 | 1079 | 1099 |
| 1 |  |  |  |  |  |  |  |  |  |  |  |  |  |  |  |  |  |  |  |  |  |  |  |  |  |
| 2 |  |  |  |  |  |  |  |  |  |  |  |  |  |  |  |  |  |  |  |  |  |  |  |  | + |
| 3 |  |  | + |  |  |  |  |  |  |  + |  |  |  |  |  |  |  |  |  |  |  |  |  | + |  |
| 4 | + |  |  | + |  |  |  |  |  |  |  |  |  |  |  |  |  |  |  |  |  | + |  |  | + |
| 5 |  |  |  | + | + | + | + | + | + |  |  | + | + | + | + | + | + | + | + | + | + | + | + |  |  |
| 6 |  |  |  |  |  |  |  | + | + |  |  | + |  |  | + | + |  |  | + |  |  |  |  |  |  |
| 7 |  |  |  |  |  |  |  | + |  |  |  |  |  |  | + | + |  |  |  |  |  |  |  |  |  |
| 8 |  |  |  |  | + |  |  |  | + |  |  |  |  |  |  |  |  |  |  |  |  |  |  |  |  |
| 9 |  |  |  |  |  | + |  |  |  |  |  |  | + |  |  |  |  |  |  |  |  | + |  |  |  |
| 10 |  |  |  |  |  |  |  |  |  | + |  | + |  | + |  |  |  |  |  |  |  |  |  |  |  |
| 11 |  |  |  |  |  |  |  | + |  |  |  |  |  |  |  |  |  |  |  |  |  |  |  |  |  |
| 12 |  |  |  | + |  |  |  |  | + |  |  | + |  |  |  |  |  |  |  |  |  |  |  |  |  |
| 13 |  |  |  |  |  |  |  |  |  |  |  |  |  |  |  |  |  |  | + |  | + |  |  |  |  |
| 14 |  |  |  |  |  |  |  | + |  | + |  |  |  | + |  |  |  |  |  |  |  |  |  |  |  |
| 15 |  |  |  |  | + |  | + | + |  |  |  |  |  | + | + | + | + | + | + | + |  | + |  | + | + |
| 16 |  |  |  |  |  |  |  |  |  |  |  |  |  |  |  |  | + |  |  |  |  |  |  |  |  |
| 17 |  |  |  |  |  |  |  |  |  |  |  |  |  | + |  |  | + |  |  |  |  |  |  |  |  |
| 18 |  | + |  |  |  |  |  |  |  |  |  |  |  |  |  |  |  |  |  |  |  |  |  |  |  |
| 19 |  |  |  |  |  |  |  | + | + |  |  |  |  |  |  |  |  |  |  |  |  |  |  |  |  |
| 20 |  |  |  | + | + |  |  |  |  |  |  |  |  |  |  |  |  |  |  |  |  |  |  |  |  |
| 21 |  |  |  |  | + |  |  |  |  |  |  |  |  |  |  |  |  |  |  |  |  |  |  |  |  |
| 22 |  |  |  | + |  |  |  |  |  |  |  |  |  |  |  | + |  |  |  | + |  |  |  |  |  |
| X |  |  |  |  |  |  |  |  |  |  |  |  |  |  |  |  |  |  |  |  |  |  |  |  |  |
| Y | + |  |  | + |  |  | + |  |  |  |  |  |  |  | + |  |  |  |  |  |  |  |  |  |  |

HUMAN CHROMOSOME

MOUSE +ve STRAND

MOUSE -ve STRAND

HUMAN -ve STRAND

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 3611 bases
        (B) TYPE: nucleic acid
        (C) STRANDEDNESS: single
        (D) TOPOLOGY: linear (xi) SEQUENCE DESCRIPTION: SEQ ID NO:1:

```
CCGCCGATGG CGCTGAGGCG GAGCATGGGG CGGCCGGGGC TCCCGCCGCT          50

GCCGCTGCCG CCGCCACCGC GGCTCGGGCT GCTGCTGGCG GCTCTGGCTT         100

CTCTGCTGCT CCCGGAGTCC GCCGCCGCAG GTCTGAAGCT CATGGGAGCC         150

CCGGTGAAGC TGACAGTGTC TCAGGGGCAG CCGGTGAAGC TCAACTGCAG         200

TGTGGAGGGG ATGGAGGAGC CTGACATCCA GTGGGTGAAG GATGGGGCTG         250

TGGTCCAGAA CTTGGACCAG TTGTACATCC CAGTCAGCGA GCAGCACTGG         300

ATCGGCTTCC TCAGCCTGAA GTCAGTGGAG CGCTCTGACG CCGGCCGGTA         350

CTGGTGCCAG GTGGAGGATG GGGGTGAAAC CGAGATCTCC CAGCCAGTGT         400

GGCTCACGGT AGAAGGTGTG CCATTTTTCA CAGTGGAGCC AAAAGATCTG         450

GCAGTGCCAC CCAATGCCCC TTTCCAACTG TCTTGTGAGG CTGTGGGTCC         500

CCCTGAACCT GTTACCATTG TCTGGTGGAG AGGAACTACG AAGATCGGGG         550

GACCCGCTCC CTCTCCATCT GTTTTAAATG TAACAGGGGT GACCCAGAGC         600

ACCATGTTTT CCTGTGAAGC TCACAACCTA AAAGGCCTGG CCTCTTCTCG         650

CACAGCCACT GTTCACCTTC AAGCACTGCC TGCAGCCCCC TTCAACATCA         700

CCGTGACAAA GCTTTCCAGC AGCAACGCTA GTGTGGCCTG GATGCCAGGT         750
```

```
GCTGATGGCC GAGCTCTGCT ACAGTCCTGT ACAGTTCAGG TGACACAGGC      800

CCCAGGAGGC TGGGAAGTCC TGGCTGTTGT GGTCCCTGTG CCCCCCTTTA      850

CCTGCCTGCT CCGGGACCTG GTGCCTGCCA CCAACTACAG CCTCAGGGTG      900

CGCTGTGCCA ATGCCTTGGG GCCCTCTCCC TATGCTGACT GGGTGCCCTT      950

TCAGACCAAG GGTCTAGCCC CAGCCAGCGC TCCCCAAAAC CTCCATGCCA     1000

TCCGCACAGA TTCAGGCCTC ATCTTGGAGT GGGAAGAAGT GATCCCCGAG     1050

GCCCCTTTGG AAGGCCCCCT GGGACCCTAC AAACTGTCCT GGGTTCAAGA     1100

CAATGGAACC CAGGATGAGC TGACAGTGGA GGGGACCAGG GCCAATTTGA     1150

CAGGCTGGGA TCCCCAAAAG GACCTGATCG TACGTGTGTG CGTCTCCAAT     1200

GCAGTTGGCT GTGGACCCTG GAGTCAGCCA CTGGTGGTCT CTTCTCATGA     1250

CCGTGCAGGC CAGCAGGGCC CTCCTCACAG CCGCACATCC TGGGTACCTG     1300

TGGTCCTTGG TGTGCTAACG GCCCTGGTGA CGGCTGCTGC CCTGGCCCTC     1350

ATCCTGCTTC GAAAGAGACG GAAAGAGACG CGGTTTGGGC AAGCCTTTGA     1400

CAGTGTCATG GCCCGGGGAG AGCCAGCCGT TCACTTCCGG GCAGCCCGGT     1450

CCTTCAATCG AGAAAGGCCC GAGCGCATCG AGGCCACATT GGACAGCTTG     1500

GGCATCAGCG ATGAACTAAA GGAAAAACTG GAGGATGTGC TCATCCCAGA     1550

GCAGCAGTTC ACCCTGGGCC GGATGTTGGG CAAAGGAGAG TTTGGTTCAG     1600

TGCGGGAGGC CCAGCTGAAG CAAGAGGATG GCTCCTTTGT GAAAGTGGCT     1650

GTGAAGATGC TGAAAGCTGA CATCATTGCC TCAAGCGACA TTGAAGAGTT     1700

CCTCAGGGAA GCAGCTTGCA TGAAGGAGTT TGACCATCCA CACGTGGCCA     1750

AACTTGTTGG GGTAAGCCTC CGGAGCAGGG CTAAAGGCCG TCTCCCCATC     1800

CCCATGGTCA TCTTGCCCTT CATGAAGCAT GGGGACCTGC ATGCCTTCCT     1850

GCTCGCCTCC CGGATTGGGG AGAACCCCTT TAACCTACCC CTCCAGACCC     1900

TGATCCGGTT CATGGTGGAC ATTGCCTGCG GCATGGAGTA CCTGAGCTCT     1950

CGGAACTTCA TCCACCGAGA CCTGGCTGCT CGGAATTGCA TGCTGGCAGA     2000

GGACATGACA GTGTGTGTGG CTGACTTCGG ACTCTCCCGG AAGATCTACA     2050

GTGGGACTA CTATCGTCAA GGCTGTGCCT CCAAACTGCC TGTCAAGTGG     2100

CTGGCCCTGG AGAGCCTGGC CGACAACCTG TATACTGTGC AGAGTGACGT     2150

GTGGGCGTTC GGGGTGACCA TGTGGGAGAT CATGACACGT GGGCAGACGC     2200

CATATGCTGG CATCGAAAAC GCTGAGATTT ACAACTACCT CATTGGCGGG     2250

AACCGCCTGA AACAGCCTCC GGAGTGTATG GAGGACGTGT ATGATCTCAT     2300

GTACCAGTGC TGGAGTGCTG ACCCCAAGCA GCGCCCGAGC TTTACTTGTC     2350

TGCGAATGGA ACTGGAGAAC ATCTTGGGCC AGCTGTCTGT GCTATCTGCC     2400

AGCCAGGACC CCTTATACAT CAACATCGAG AGAGCTGAGG AGCCCACTGC     2450

GGGAGGCAGC CTGGAGCTAC CTGGCAGGGA TCAGCCCTAC AGTGGGGCTG     2500

GGGATGGCAG TGGCATGGGG GCAGTGGGTG GCACTCCCAG TGACTGTCGG     2550

TACATACTCA CCCCCGGAGG GCTGGCTGAG CAGCCAGGGC AGGCAGAGCA     2600

CCAGCCAGAG AGTCCCCTCA ATGAGACACA GAGGCTTTTG CTGCTGCAGC     2650

AAGGGCTACT GCCACACAGT AGCTGTTAGC CACAGGCAG AGGGCATCGG      2700

GGCCATTTGG CCGGCTCTGG TGGCCACTGA GCTGGCTGAC TAAGCCCCGT     2750
```

```
CTGACCCCAG CCCAGACAGC AAGGTGTGGA GGCTCCTGTG GTAGTCCTCC          2800

CAAGCTGTGC TGGGAAGCCC GGACTGACCA AATCACCCAA TCCCAGTTCT          2850

TCCTGCAACC ACTCTGTGGC CAGCCTGGCA TCAGTTTAGG CCTTGGCTTG          2900

ATGGAAGTGG GCCAGTCCTG GTTGTCTGAA CCCAGGCAGC TGGCAGGAGT          2950

GGGGTGGTTA TGTTTCCATG GTTACCATGG GTGTGGATGG CAGTGTGGGG          3000

AGGGCAGGTC CAGCTCTGTG GGCCCTACCC TCCTGCTGAG CTGCCCCTGC          3050

TGCTTAAGTG CATGCATTGA GCTGCCTCCA GCCTGGTGGC CCAGCTATTA          3100

CCACACTTGG GGTTTAAATA TCCAGGTGTG CCCCTCCAAG TCACAAAGAG          3150

ATGTCCTTGT AATATTCCCT TTTAGGTGAG GGTTGGTAAG GGGTTGGTAT          3200

CTCAGGTCTG AATCTTCACC ATCTTTCTGA TTCCGCACCC TGCCTACGCC          3250

AGGAGAAGTT GAGGGGAGCA TGCTTCCCTG CAGCTGACCG GGTCACACAA          3300

AGGCATGCTG GAGTACCCAG CCTATCAGGT GCCCCTCTTC CAAAGGCAGC          3350

GTGCCGAGCC AGCAAGAGGA AGGGGTGCTG TGAGGCTTGC CCAGGAGCAA          3400

GTGAGGCCGG AGAGGAGTTC AGGAACCCTT CTCCATACCC ACAATCTGAG          3450

CACGCTACCA AATCTCAAAA TATCCTAAGA CTAACAAAGG CAGCTGTGTC          3500

TGAGCCCAAC CCTTCTAAAC GGTGACCTTT AGTGCCAACT TCCCCTCTAA          3550

CTGGACAGCC TCTTCTGTCC CAAGTCTCCA GAGAGAAATC AGGCCTGATG          3600

AGGGGGAATT C                                                    3611

(2) INFORMATION FOR SEQ ID NO:2:

(i) SEQUENCE CHARACTERISTICS:
        (A) LENGTH: 890 amino acids
        (B) TYPE: amino acid
        (D) TOPOLOGY: linear (xi) SEQUENCE DESCRIPTION: SEQ ID NO:2:

Met Ala Leu Arg Arg Ser Met Gly Arg Pro Gly Leu Pro Pro Leu
 1               5                  10                  15

Pro Leu Pro Pro Pro Arg Leu Gly Leu Leu Leu Ala Ala Leu
                20                  25                  30

Ala Ser Leu Leu Leu Pro Glu Ser Ala Ala Ala Gly Leu Lys Leu
                35                  40                  45

Met Gly Ala Pro Val Lys Leu Thr Val Ser Gln Gly Gln Pro Val
                50                  55                  60

Lys Leu Asn Cys Ser Val Glu Gly Met Glu Glu Pro Asp Ile Gln
                65                  70                  75

Trp Val Lys Asp Gly Ala Val Val Gln Asn Leu Asp Gln Leu Tyr
                80                  85                  90

Ile Pro Val Ser Glu Gln His Trp Ile Gly Phe Leu Ser Leu Lys
                95                 100                 105

Ser Val Glu Arg Ser Asp Ala Gly Arg Tyr Trp Cys Gln Val Glu
               110                 115                 120

Asp Gly Gly Glu Thr Glu Ile Ser Gln Pro Val Trp Leu Thr Val
               125                 130                 135

Glu Gly Val Pro Phe Phe Thr Val Glu Pro Lys Asp Leu Ala Val
               140                 145                 150

Pro Pro Asn Ala Pro Phe Gln Leu Ser Cys Glu Ala Val Gly Pro
               155                 160                 165
```

-continued

```
Pro Glu Pro Val Thr Ile Val Trp Trp Arg Gly Thr Thr Lys Ile
            170                 175                 180

Gly Gly Pro Ala Pro Ser Pro Ser Val Leu Asn Val Thr Gly Val
            185                 190                 195

Thr Gln Ser Thr Met Phe Ser Cys Glu Ala His Asn Leu Lys Gly
            200                 205                 210

Leu Ala Ser Ser Arg Thr Ala Thr Val His Leu Gln Ala Leu Pro
            215                 220                 225

Ala Ala Pro Phe Asn Ile Thr Val Thr Lys Leu Ser Ser Ser Asn
            230                 235                 240

Ala Ser Val Ala Trp Met Pro Gly Ala Asp Gly Arg Ala Leu Leu
            245                 250                 255

Gln Ser Cys Thr Val Gln Val Thr Gln Ala Pro Gly Gly Trp Glu
            260                 265                 270

Val Leu Ala Val Val Pro Val Pro Pro Phe Thr Cys Leu Leu
            275                 280                 285

Arg Asp Leu Val Pro Ala Thr Asn Tyr Ser Leu Arg Val Arg Cys
            290                 295                 300

Ala Asn Ala Leu Gly Pro Ser Pro Tyr Ala Asp Trp Val Pro Phe
            305                 310                 315

Gln Thr Lys Gly Leu Ala Pro Ala Ser Ala Pro Gln Asn Leu His
            320                 325                 330

Ala Ile Arg Thr Asp Ser Gly Leu Ile Leu Glu Trp Glu Glu Val
            335                 340                 345

Ile Pro Glu Ala Pro Leu Glu Gly Pro Leu Gly Pro Tyr Lys Leu
            350                 355                 360

Ser Trp Val Gln Asp Asn Gly Thr Gln Asp Glu Leu Thr Val Glu
            365                 370                 375

Gly Thr Arg Ala Asn Leu Thr Gly Trp Asp Pro Gln Lys Asp Leu
            380                 385                 390

Ile Val Arg Val Cys Val Ser Asn Ala Val Gly Cys Gly Pro Trp
            395                 400                 405

Ser Gln Pro Leu Val Val Ser Ser His Asp Arg Ala Gly Gln Gln
            410                 415                 420

Gly Pro Pro His Ser Arg Thr Ser Trp Val Pro Val Val Leu Gly
            425                 430                 435

Val Leu Thr Ala Leu Val Thr Ala Ala Leu Ala Leu Ile Leu
            440                 445                 450

Leu Arg Lys Arg Arg Lys Glu Thr Arg Phe Gly Gln Ala Phe Asp
            455                 460                 465

Ser Val Met Ala Arg Gly Glu Pro Ala Val His Phe Arg Ala Ala
            470                 475                 480

Arg Ser Phe Asn Arg Glu Arg Pro Glu Arg Ile Glu Ala Thr Leu
            485                 490                 495

Asp Ser Leu Gly Ile Ser Asp Glu Leu Lys Glu Lys Leu Glu Asp
            500                 505                 510

Val Leu Ile Pro Glu Gln Gln Phe Thr Leu Gly Arg Met Leu Gly
            515                 520                 525

Lys Gly Glu Phe Gly Ser Val Arg Glu Ala Gln Leu Lys Gln Glu
            530                 535                 540

Asp Gly Ser Phe Val Lys Val Ala Val Lys Met Leu Lys Ala Asp
            545                 550                 555
```

```
Ile Ile Ala Ser Ser Asp Ile Glu Glu Phe Leu Arg Glu Ala Ala
            560                 565                 570

Cys Met Lys Glu Phe Asp His Pro His Val Ala Lys Leu Val Gly
            575                 580                 585

Val Ser Leu Arg Ser Arg Ala Lys Gly Arg Leu Pro Ile Pro Met
            590                 595                 600

Val Ile Leu Pro Phe Met Lys His Gly Asp Leu His Ala Phe Leu
            605                 610                 615

Leu Ala Ser Arg Ile Gly Glu Asn Pro Phe Asn Leu Pro Leu Gln
            620                 625                 630

Thr Leu Ile Arg Phe Met Val Asp Ile Ala Cys Gly Met Glu Tyr
            635                 640                 645

Leu Ser Ser Arg Asn Phe Ile His Arg Asp Leu Ala Ala Arg Asn
            650                 655                 660

Cys Met Leu Ala Glu Asp Met Thr Val Cys Val Ala Asp Phe Gly
            665                 670                 675

Leu Ser Arg Lys Ile Tyr Ser Gly Asp Tyr Tyr Arg Gln Gly Cys
            680                 685                 690

Ala Ser Lys Leu Pro Val Lys Trp Leu Ala Leu Glu Ser Leu Ala
            695                 700                 705

Asp Asn Leu Tyr Thr Val Gln Ser Asp Val Trp Ala Phe Gly Val
            710                 715                 720

Thr Met Trp Glu Ile Met Thr Arg Gly Gln Thr Pro Tyr Ala Gly
            725                 730                 735

Ile Glu Asn Ala Glu Ile Tyr Asn Tyr Leu Ile Gly Gly Asn Arg
            740                 745                 750

Leu Lys Gln Pro Pro Glu Cys Met Glu Asp Val Tyr Asp Leu Met
            755                 760                 765

Tyr Gln Cys Trp Ser Ala Asp Pro Lys Gln Arg Pro Ser Phe Thr
            770                 775                 780

Cys Leu Arg Met Glu Leu Glu Asn Ile Leu Gly Gln Leu Ser Val
            785                 790                 795

Leu Ser Ala Ser Gln Asp Pro Leu Tyr Ile Asn Ile Glu Arg Ala
            800                 805                 810

Glu Glu Pro Thr Ala Gly Gly Ser Leu Glu Leu Pro Gly Arg Asp
            815                 820                 825

Gln Pro Tyr Ser Gly Ala Gly Asp Gly Ser Gly Met Gly Ala Val
            830                 835                 840

Gly Gly Thr Pro Ser Asp Cys Arg Tyr Ile Leu Thr Pro Gly Gly
            845                 850                 855

Leu Ala Glu Gln Pro Gly Gln Ala Glu His Gln Pro Glu Ser Pro
            860                 865                 870

Leu Asn Glu Thr Gln Arg Leu Leu Leu Leu Gln Gln Gly Leu Leu
            875                 880                 885

Pro His Ser Ser Cys
            890

(2) INFORMATION FOR SEQ ID NO:3:

(i) SEQUENCE CHARACTERISTICS:
        (A) LENGTH: 3637 bases
        (B) TYPE: nucleic acid
        (C) STRANDEDNESS: single
        (D) TOPOLOGY: linear (xi) SEQUENCE DESCRIPTION: SEQ ID NO:3:
```

-continued

```
GAATTCTCGA GTCGACGTTG GACTTGAAGG AATGCCAAGA GATGCTGCCC          50
CCACCCCCTT AGGCCCGAGG GATCAGGAGC TATGGGACCA GAGGCCCTGT         100
CATCTTTACT GCTGCTGCTC TTGGTGGCAA GTGGAGATGC TGACATGAAG         150
GGACATTTTG ATCCTGCCAA GTGCCGCTAT GCCCTGGGCA TGCAGGACCG         200
GACCATCCCA GACAGTGACA TCTCTGCTTC CAGCTCCTGG TCAGATTCCA         250
CTGCCGCCCG CCACAGCAGG TTGGAGAGCA GTGACGGGGA TGGGGCCTGG         300
TGCCCCGCAG GGTCGGTGTT TCCCAAGGAG GAGGAGTACT TGCAGGTGGA         350
TCTACAACGA CTGCACCTGG TGGCTCTGGT GGGCACCCAG GGACGGCATG         400
CCGGGGGCCT GGGCAAGGAG TTCTCCCGGA GCTACCGGCT GCGTTACTCC         450
CGGGATGGTC GCCGCTGGAT GGGCTGGAAG GACCGCTGGG GTCAGGAGGT         500
GATCTCAGGC AATGAGGACC CTGAGGGAGT GGTGCTGAAG GACCTTGGGC         550
CCCCCATGGT TGCCCGACTG GTTCGCTTCT ACCCCCGGGC TGACCGGGTC         600
ATGAGCGTCT GTCTGCGGGT AGAGCTCTAT GGCTGCCTCT GGAGGGATGG         650
ACTCCTGTCT TACACCGCCC CTGTGGGGCA GACAATGTAT TTATCTGAGG         700
CCGTGTACCT CAACGACTCC ACCTATGACG GACATACCGT GGGCGGACTG         750
CAGTATGGGG GTCTGGGCCA GCTGGCAGAT GGTGTGGTGG GGCTGGATGA         800
CTTTAGGAAG AGTCAGGAGC TGCGGGTCTG GCCAGGCTAT GACTATGTGG         850
GATGGAGCAA CCACAGCTTC TCCAGTGGCT ATGTGGAGAT GGAGTTTGAG         900
TTTGACCGGC TGAGGGCCTT CCAGGCTATG CAGGTCCACT GTAACAACAT         950
GCACACGCTG GGAGCCCGTC TGCCTGGCGG GGTGGAATGT CGCTTCCGGC        1000
GTGGCCCTGC CATGGCCTGG GAGGGGGAGC CCATGCGCCA CAACCTAGGG        1050
GGCAACCTGG GGGACCCCAG AGCCCGGGCT GTCTCAGTGC CCCTTGGCGG        1100
CCGTGTGGCT CGCTTTCTGC AGTGCCGCTT CCTCTTTGCG GGCCCTGGT         1150
TACTCTTCAG CGAAATCTCC TTCATCTCTG ATGTGGTGAA CAATTCCTCT        1200
CCGGCACTGG GAGGCACCTT CCCGCCAGCC CCTGGTGGC CGCCTGGCCC         1250
ACCTCCCACC AACTTCAGCA GCTTGGAGCT GGAGCCCAGA GGCCAGCAGC        1300
CCGTGGCCAA GCCCGAGGGG AGCCCGACCG CCATCCTCAT CGGCTGCCTG        1350
GTGGCCATCA TCCTGCTCCT GCTGCTCATC ATTGCCCTCA TGCTCTGGCG        1400
GCTGCACTGG CGCAGGCTCC TCAGCAAGGC TGAACGGAGG GTGTTGGAAG        1450
AGGAGCTGAC GGTTCACCTC TCTGTCCCTG GGACACTAT CCTCATCAAC         1500
AACCGCCCAG GTCCTAGAGA GCCACCCCCG TACCAGGAGC CCCGGCCTCG        1550
TGGGAATCCG CCCCACTCCG CTCCCTGTGT CCCCAATGGC TCTGCGTTGC        1600
TGCTCTCCAA TCCAGCCTAC CGCCTCCTTC TGGCCACTTA CGCCCGTCCC        1650
CCTCGAGGCC CGGGCCCCCC CACACCCGCC TGGGCCAAAC CCACCAACAC        1700
CCAGGCCTAC AGTGGGGACT ATATGGAGCC TGAGAAGCCA GGCGCCCCGC        1750
TTCTGCCCCC ACCTCCCCAG AACAGCGTCC CCCATTATGC CGAGGCTGAC        1800
ATTGTTACCC TGCAGGGCGT CACCGGGGGC AACACCTATG CTGTGCCTGC        1850
ACTGCCCCCA GGGGCAGTCG GGGATGGGCC CCCAGAGTG GATTTCCCTC         1900
GATCTCGACT CCGCTTCAAG GAGAAGCTTG GCGAGGGCCA GTTTGGGGAG        1950
```

-continued

```
GTGCACCTGT GTGAGGTCGA CAGCCCTCAA GATCTGGTCA GTCTTGATTT      2000

CCCCCTTAAT GTGCGTAAGG GACACCCTTT GCTGGTAGCT GTCAAGATCT      2050

TACGGCCAGA TGCCACCAAG AATGCCAGGA ATGATTTCCT GAAAGAGGTG      2100

AAGATCATGT CGAGGCTCAA GGACCCAAAC ATCATTCGGC TGCTGGGCGT      2150

GTGTGTGCAG GACGACCCCC TCTGCATGAT TACTGACTAC ATGGAGAACG      2200

GCGACCTCAA CCAGTTCCTC AGTGCCCACC AGCTGGAGGA CAAGGCAGCC      2250

GAGGGGGCCC CTGGGGACGG GCAGGCTGCG CAGGGGCCCA CCATCAGCTA      2300

CCCAATGCTG CTGCATGTGG CAGCCCAGAT CGCCTCCGGC ATGCGCTATC      2350

TGGCCACACT CAACTTTGTA CATCGGGACC TGGCCACGCG GAACTGCCTA      2400

GTTGGGGAAA ATTTCACCAT CAAAATCGCA GACTTTGGCA TGAGCCGGAA      2450

CCTCTATGCT GGGGACTATT ACCGTGTGCA GGGCCGGGCA GTGCTGCCCA      2500

TCCGCTGGAT GGCCTGGGAG TGCATCCTCA TGGGGAAGTT CACGACTGCG      2550

AGTGACGTGT GGGCCTTTGG TGTGACCCTG TGGGAGGTGC TGATGCTCTG      2600

TAGGGCCCAG CCCTTTGGGC AGCTCACCGA CGAGCAGGTC ATCGAGAACG      2650

CGGGGGAGTT CTTCCGGGAC CAGGGCCGGC AGGTGTACCT GTCCCGGCCG      2700

CCTGCCTGCC CGCAGGGCCT ATATGAGCTG ATGCTTCGGT GCTGGAGCCG      2750

GGAGTCTGAG CAGCGACCAC CCTTTTCCCA GCTGCATCGG TTCCTGGCAG      2800

AGGATGCACT CAACACGGTG TGAATCACAC ATCCAGCTGC CCCTCCCTCA      2850

GGGAGTGATC CAGGGGAAGC CAGTGACACT AAAACAAGAG GACACAATGG      2900

CACCTCTGCC CTTCCCCTCC CGACAGCCCA TCACCTCTAA TAGAGGCAGT      2950

GAGACTGCAG AAGCCCCTGT CGCCCACCCA GCTGGTCCTG TGGATGGGAT      3000

CCTCTCCACC CTCCTCTAGC CATCCCTTGG GGAAGGGTGG GGAGAAATAT      3050

AGGATAGACA CTGGACATGG CCCATTGGAG CACCTGGGCC CCACTGGACA      3100

ACACTGATTC CTGGAGAGGT GGCTGCGCCC CCAGCTTCTC TCTCCCTGTC      3150

ACACACTGGA CCCCACTGGC TGAGAATCTG GGGGTGAGGA GGACAAGAAG      3200

GAGAGGAAAA TGTTTCCTTG TGCCTGCTCC TGTACTTGTC CTCAGCTTGG      3250

GCTTCTTCCT CCTCCATCAC CTGAAACACT GGACCTGGGG GTAGCCCCGC      3300

CCCAGCCCTC AGTCACCCCC ACTTCCCACC TGCAGTCTTG TAGCTAGAAC      3350

TTCTCTAAGC CTATACGTTT CTGTGGAGTA AATATTGGGA TTGGGGGAA      3400

AGAGGGAGCA ACGGCCCATA GCCTTGGGGT TGGACATCTC TAGTGTAGCT      3450

GCCACATTGA TTTTTCTATA ATCACTTGGG GTTTGTACAT TTTTGGGGGG      3500

AGAGACACAG ATTTTTACAC TAATATATGG ACCTAGCTTG AGGCAATTTT      3550

AATCCCCTGC ACTAGGCAGG TAATAATAAA GGTTGAGTTT TCCACAAAAA      3600

AAAAAAAAAA AAAAAAAAAA AAAAAAAAAA AAAAAA                    3637
```

(2) INFORMATION FOR SEQ ID NO:4:

(i) SEQUENCE CHARACTERISTICS:
    (A) LENGTH: 913 amino acids
    (B) TYPE: amino acid
    (D) TOPOLOGY: linear (xi) SEQUENCE DESCRIPTION: SEQ ID NO:4:

Met Gly Pro Glu Ala Leu Ser Ser Leu Leu Leu Leu Leu Val

-continued

```
  1               5                   10                  15
Ala Ser Gly Asp Ala Asp Met Lys Gly His Phe Asp Pro Ala Lys
                 20                  25                  30
Cys Arg Tyr Ala Leu Gly Met Gln Asp Arg Thr Ile Pro Asp Ser
                 35                  40                  45
Asp Ile Ser Ala Ser Ser Ser Trp Ser Asp Ser Thr Ala Ala Arg
                 50                  55                  60
His Ser Arg Leu Glu Ser Ser Asp Gly Asp Gly Ala Trp Cys Pro
                 65                  70                  75
Ala Gly Ser Val Phe Pro Lys Glu Glu Tyr Leu Gln Val Asp
                 80                  85                  90
Leu Gln Arg Leu His Leu Val Ala Leu Val Gly Thr Gln Gly Arg
                 95                  100                 105
His Ala Gly Gly Leu Gly Lys Glu Phe Ser Arg Ser Tyr Arg Leu
                 110                 115                 120
Arg Tyr Ser Arg Asp Gly Arg Arg Trp Met Gly Trp Lys Asp Arg
                 125                 130                 135
Trp Gly Gln Glu Val Ile Ser Gly Asn Glu Asp Pro Glu Gly Val
                 140                 145                 150
Val Leu Lys Asp Leu Gly Pro Pro Met Val Ala Arg Leu Val Arg
                 155                 160                 165
Phe Tyr Pro Arg Ala Asp Arg Val Met Ser Val Cys Leu Arg Val
                 170                 175                 180
Glu Leu Tyr Gly Cys Leu Trp Arg Asp Gly Leu Leu Ser Tyr Thr
                 185                 190                 195
Ala Pro Val Gly Gln Thr Met Tyr Leu Ser Glu Ala Val Tyr Leu
                 200                 205                 210
Asn Asp Ser Thr Tyr Asp Gly His Thr Val Gly Gly Leu Gln Tyr
                 215                 220                 225
Gly Gly Leu Gly Gln Leu Ala Asp Gly Val Val Gly Leu Asp Asp
                 230                 235                 240
Phe Arg Lys Ser Gln Glu Leu Arg Val Trp Pro Gly Tyr Asp Tyr
                 245                 250                 255
Val Gly Trp Ser Asn His Ser Phe Ser Gly Tyr Val Glu Met
                 260                 265                 270
Glu Phe Glu Phe Asp Arg Leu Arg Ala Phe Gln Ala Met Gln Val
                 275                 280                 285
His Cys Asn Asn Met His Thr Leu Gly Ala Arg Leu Pro Gly Gly
                 290                 295                 300
Val Glu Cys Arg Phe Arg Arg Gly Pro Ala Met Ala Trp Glu Gly
                 305                 310                 315
Glu Pro Met Arg His Asn Leu Gly Gly Asn Leu Gly Asp Pro Arg
                 320                 325                 330
Ala Arg Ala Val Ser Val Pro Leu Gly Gly Arg Val Ala Arg Phe
                 335                 340                 345
Leu Gln Cys Arg Phe Leu Phe Ala Gly Pro Trp Leu Leu Phe Ser
                 350                 355                 360
Glu Ile Ser Phe Ile Ser Asp Val Val Asn Asn Ser Ser Pro Ala
                 365                 370                 375
Leu Gly Gly Thr Phe Pro Pro Ala Pro Trp Trp Pro Pro Gly Pro
                 380                 385                 390
Pro Pro Thr Asn Phe Ser Ser Leu Glu Leu Glu Pro Arg Gly Gln
                 395                 400                 405
```

-continued

```
Gln Pro Val Ala Lys Pro Glu Gly Ser Pro Thr Ala Ile Leu Ile
                410                 415                 420
Gly Cys Leu Val Ala Ile Leu Leu Leu Leu Ile Ile Ala
            425                 430                 435
Leu Met Leu Trp Arg Leu His Trp Arg Arg Leu Leu Ser Lys Ala
                440                 445                 450
Glu Arg Arg Val Leu Glu Glu Leu Thr Val His Leu Ser Val
                455                 460                 465
Pro Gly Asp Thr Ile Leu Ile Asn Asn Arg Pro Gly Pro Arg Glu
                470                 475                 480
Pro Pro Pro Tyr Gln Glu Pro Arg Pro Arg Gly Asn Pro His
                485                 490                 495
Ser Ala Pro Cys Val Pro Asn Gly Ser Ala Leu Leu Leu Ser Asn
                500                 505                 510
Pro Ala Tyr Arg Leu Leu Leu Ala Thr Tyr Ala Arg Pro Pro Arg
                515                 520                 525
Gly Pro Gly Pro Pro Thr Pro Ala Trp Ala Lys Pro Thr Asn Thr
                530                 535                 540
Gln Ala Tyr Ser Gly Asp Tyr Met Glu Pro Glu Lys Pro Gly Ala
                545                 550                 555
Pro Leu Leu Pro Pro Pro Gln Asn Ser Val Pro His Tyr Ala
            560                 565                 570
Glu Ala Asp Ile Val Thr Leu Gln Gly Val Thr Gly Gly Asn Thr
                575                 580                 585
Tyr Ala Val Pro Ala Leu Pro Pro Gly Ala Val Gly Asp Gly Pro
                590                 595                 600
Pro Arg Val Asp Phe Pro Arg Ser Arg Leu Arg Phe Lys Glu Lys
                605                 610                 615
Leu Gly Glu Gly Gln Phe Gly Glu Val His Leu Cys Glu Val Asp
                620                 625                 630
Ser Pro Gln Asp Leu Val Ser Leu Asp Phe Pro Leu Asn Val Arg
                635                 640                 645
Lys Gly His Pro Leu Leu Val Ala Val Lys Ile Leu Arg Pro Asp
                650                 655                 660
Ala Thr Lys Asn Ala Arg Asn Asp Phe Leu Lys Glu Val Lys Ile
                665                 670                 675
Met Ser Arg Leu Lys Asp Pro Asn Ile Ile Arg Leu Leu Gly Val
                680                 685                 690
Cys Val Gln Asp Asp Pro Leu Cys Met Ile Thr Asp Tyr Met Glu
                695                 700                 705
Asn Gly Asp Leu Asn Gln Phe Leu Ser Ala His Gln Leu Glu Asp
                710                 715                 720
Lys Ala Ala Glu Gly Ala Pro Gly Asp Gly Gln Ala Ala Gln Gly
                725                 730                 735
Pro Thr Ile Ser Tyr Pro Met Leu Leu His Val Ala Ala Gln Ile
                740                 745                 750
Ala Ser Gly Met Arg Tyr Leu Ala Thr Leu Asn Phe Val His Arg
                755                 760                 765
Asp Leu Ala Thr Arg Asn Cys Leu Val Gly Glu Asn Phe Thr Ile
                770                 775                 780
Lys Ile Ala Asp Phe Gly Met Ser Arg Asn Leu Tyr Ala Gly Asp
                785                 790                 795
```

-continued

```
Tyr Tyr Arg Val Gln Gly Arg Ala Val Leu Pro Ile Arg Trp Met
            800                 805                 810

Ala Trp Glu Cys Ile Leu Met Gly Lys Phe Thr Thr Ala Ser Asp
            815                 820                 825

Val Trp Ala Phe Gly Val Thr Leu Trp Glu Val Leu Met Leu Cys
            830                 835                 840

Arg Ala Gln Pro Phe Gly Gln Leu Thr Asp Glu Gln Val Ile Glu
            845                 850                 855

Asn Ala Gly Glu Phe Phe Arg Asp Gln Gly Arg Gln Val Tyr Leu
            860                 865                 870

Ser Arg Pro Pro Ala Cys Pro Gln Gly Leu Tyr Glu Leu Met Leu
            875                 880                 885

Arg Cys Trp Ser Arg Glu Ser Glu Gln Arg Pro Pro Phe Ser Gln
            890                 895                 900

Leu His Arg Phe Leu Ala Glu Asp Ala Leu Asn Thr Val
            905                 910             913
```

(2) INFORMATION FOR SEQ ID NO:5:

(i) SEQUENCE CHARACTERISTICS:
        (A) LENGTH: 1164 bases
        (B) TYPE: nucleic acid
        (C) STRANDEDNESS: single
        (D) TOPOLOGY: linear (xi) SEQUENCE DESCRIPTION: SEQ ID NO:5:

```
GCAGGTCTGA AGCTCATGGG AGCCCCGGTG AAGCTGACAG TGTCTCAGGG           50

GCAGCCGGTG AAGCTCAACT GCAGTGTGGA GGGGATGGAG GAGCCTGACA          100

TCCAGTGGGT GAAGGATGGG GCTGTGGTCC AGAACTTGGA CCAGTTGTAC          150

ATCCCAGTCA GCGAGCAGCA CTGGATCGGC TTCCTCAGCC TGAAGTCAGT          200

GGAGCGCTCT GACGCCGGCC GGTACTGGTG CCAGGTGGAG GATGGGGGTG          250

AAACCGAGAT CTCCCAGCCA GTGTGGCTCA CGGTAGAAGG TGTGCCATTT          300

TTCACAGTGG AGCCAAAAGA TCTGGCAGTG CCACCCAATG CCCCTTTCCA          350

ACTGTCTTGT GAGGCTGTGG GTCCCCCTGA ACCTGTTACC ATTGTCTGGT          400

GGAGAGGAAC TACGAAGATC GGGGGACCCG CTCCCTCTCC ATCTGTTTTA          450

AATGTAACAG GGGTGACCCA GAGCACCATG TTTTCCTGTG AAGCTCACAA          500

CCTAAAAGGC CTGGCCTCTT CTCGCACAGC CACTGTTCAC CTTCAAGCAC          550

TGCCTGCAGC CCCCTTCAAC ATCACCGTGA CAAAGCTTTC CAGCAGCAAC          600

GCTAGTGTGG CCTGGATGCC AGGTGCTGAT GGCCGAGCTC TGCTACAGTC          650

CTGTACAGTT CAGGTGACAC AGGCCCCAGG AGGCTGGGAA GTCCTGGCTG          700

TTGTGGTCCC TGTGCCCCCC TTTACCTGCC TGCTCCGGGA CCTGGTGCCT          750

GCCACCAACT ACAGCCTCAG GGTGCGCTGT GCCAATGCCT TGGGGCCCTC          800

TCCCTATGCT GACTGGGTGC CCTTTCAGAC CAAGGGTCTA GCCCCAGCCA          850

GCGCTCCCCA AAACCTCCAT GCCATCCGCA CAGATTCAGG CCTCATCTTG          900

GAGTGGGAAG AAGTGATCCC CGAGGCCCCT TTGGAAGGCC CCTGGGACC           950

CTACAAACTG TCCTGGGTTC AAGACAATGG AACCCAGGAT GAGCTGACAG         1000

TGGAGGGGAC CAGGGCCAAT TTGACAGGCT GGGATCCCCA AAAGGACCTG         1050

ATCGTACGTG TGTGCGTCTC CAATGCAGTT GGCTGTGGAC CCTGGAGTCA         1100
```

```
GCCACTGGTG GTCTCTTCTC ATGACCGTGC AGGCCAGCAG GGCCCTCCTC          1150

ACAGCCGCAC ATCC                                                 1164
```

(2) INFORMATION FOR SEQ ID NO:6:

(i) SEQUENCE CHARACTERISTICS:
        (A) LENGTH: 388 amino acids
        (B) TYPE: amino acid
        (D) TOPOLOGY: linear (xi) SEQUENCE DESCRIPTION: SEQ ID NO:6:

```
Ala Gly Leu Lys Leu Met Gly Ala Pro Val Lys Leu Thr Val Ser
 1               5                  10                  15

Gln Gly Gln Pro Val Lys Leu Asn Cys Ser Val Glu Gly Met Glu
                20                  25                  30

Glu Pro Asp Ile Gln Trp Val Lys Asp Gly Ala Val Val Gln Asn
                35                  40                  45

Leu Asp Gln Leu Tyr Ile Pro Val Ser Glu Gln His Trp Ile Gly
                50                  55                  60

Phe Leu Ser Leu Lys Ser Val Glu Arg Ser Asp Ala Gly Arg Tyr
                65                  70                  75

Trp Cys Gln Val Glu Asp Gly Gly Glu Thr Glu Ile Ser Gln Pro
                80                  85                  90

Val Trp Leu Thr Val Glu Gly Val Pro Phe Phe Thr Val Glu Pro
                95                 100                 105

Lys Asp Leu Ala Val Pro Pro Asn Ala Pro Phe Gln Leu Ser Cys
               110                 115                 120

Glu Ala Val Gly Pro Pro Glu Pro Val Thr Ile Val Trp Trp Arg
               125                 130                 135

Gly Thr Thr Lys Ile Gly Gly Pro Ala Pro Ser Pro Ser Val Leu
               140                 145                 150

Asn Val Thr Gly Val Thr Gln Ser Thr Met Phe Ser Cys Glu Ala
               155                 160                 165

His Asn Leu Lys Gly Leu Ala Ser Ser Arg Thr Ala Thr Val His
               170                 175                 180

Leu Gln Ala Leu Pro Ala Ala Pro Phe Asn Ile Thr Val Thr Lys
               185                 190                 195

Leu Ser Ser Ser Asn Ala Ser Val Ala Trp Met Pro Gly Ala Asp
               200                 205                 210

Gly Arg Ala Leu Leu Gln Ser Cys Thr Val Gln Val Thr Gln Ala
               215                 220                 225

Pro Gly Gly Trp Glu Val Leu Ala Val Val Pro Val Pro Val Pro
               230                 235                 240

Phe Thr Cys Leu Leu Arg Asp Leu Val Pro Ala Thr Asn Tyr Ser
               245                 250                 255

Leu Arg Val Arg Cys Ala Asn Ala Leu Gly Pro Ser Pro Tyr Ala
               260                 265                 270

Asp Trp Val Pro Phe Gln Thr Lys Gly Leu Ala Pro Ala Ser Ala
               275                 280                 285

Pro Gln Asn Leu His Ala Ile Arg Thr Asp Ser Gly Leu Ile Leu
               290                 295                 300

Glu Trp Glu Glu Val Ile Pro Glu Ala Pro Leu Glu Gly Pro Leu
               305                 310                 315

Gly Pro Tyr Lys Leu Ser Trp Val Gln Asp Asn Gly Thr Gln Asp
               320                 325                 330
```

```
Glu Leu Thr Val Glu Gly Thr Arg Ala Asn Leu Thr Gly Trp Asp
                335                 340                 345

Pro Gln Lys Asp Leu Ile Val Arg Val Cys Val Ser Asn Ala Val
                350                 355                 360

Gly Cys Gly Pro Trp Ser Gln Pro Leu Val Val Ser Ser His Asp
                365                 370                 375

Arg Ala Gly Gln Gln Gly Pro Pro His Ser Arg Thr Ser
                380                 385         388
```

(2) INFORMATION FOR SEQ ID NO:7:

(i) SEQUENCE CHARACTERISTICS:
        (A) LENGTH: 1197 bases
        (B) TYPE: nucleic acid
        (C) STRANDEDNESS: single
        (D) TOPOLOGY: linear (xi) SEQUENCE DESCRIPTION: SEQ ID NO:7:

```
GATGCTGACA TGAAGGGACA TTTTGATCCT GCCAAGTGCC GCTATGCCCT          50

GGGCATGCAG GACCGGACCA TCCCAGACAG TGACATCTCT GCTTCCAGCT         100

CCTGGTCAGA TTCCACTGCC GCCCGCCACA GCAGGTTGGA GAGCAGTGAC         150

GGGGATGGGG CCTGGTGCCC CGCAGGGTCG GTGTTTCCCA AGGAGGAGGA         200

GTACTTGCAG GTGGATCTAC AACGACTGCA CCTGGTGGCT CTGGTGGGCA         250

CCCAGGGACG GCATGCCGGG GGCCTGGGCA AGGAGTTCTC CCGGAGCTAC         300

CGGCTGCGTT ACTCCCGGGA TGGTCGCCGC TGGATGGGCT GGAAGGACCG         350

CTGGGGTCAG GAGGTGATCT CAGGCAATGA GGACCCTGAG GGAGTGGTGC         400

TGAAGGACCT TGGGCCCCCC ATGGTTGCCC GACTGGTTCG CTTCTACCCC         450

CGGGCTGACC GGGTCATGAG CGTCTGTCTG CGGGTAGAGC TCTATGGCTG         500

CCTCTGGAGG GATGGACTCC TGTCTTACAC CGCCCCTGTG GGGCAGACAA         550

TGTATTTATC TGAGGCCGTG TACCTCAACG ACTCCACCTA TGACGGACAT         600

ACCGTGGGCG GACTGCAGTA TGGGGGTCTG GGCCAGCTGG CAGATGGTGT         650

GGTGGGGCTG GATGACTTTA GGAAGAGTCA GGAGCTGCGG GTCTGGCCAG         700

GCTATGACTA TGTGGGATGG AGCAACCACA GCTTCTCCAG TGGCTATGTG         750

GAGATGGAGT TTGAGTTTGA CCGGCTGAGG GCCTTCCAGG CTATGCAGGT         800

CCACTGTAAC AACATGCACA CGCTGGGAGC CCGTCTGCCT GGCGGGGTGG         850

AATGTCGCTT CCGGCGTGGC CCTGCCATGG CCTGGGAGGG GGAGCCCATG         900

CGCCACAACC TAGGGGGCAA CCTGGGGGAC CCCAGAGCCC GGGCTGTCTC         950

AGTGCCCCTT GGCGGCCGTG TGGCTCGCTT TCTGCAGTGC CGCTTCCTCT        1000

TTGCGGGGCC CTGGTTACTC TTCAGCGAAA TCTCCTTCAT CTCTGATGTG        1050

GTGAACAATT CCTCTCCGGC ACTGGGAGGC ACCTTCCCGC CAGCCCCCTG        1100

GTGGCCGCCT GGCCCACCTC CCACCAACTT CAGCAGCTTG GAGCTGGAGC        1150

CCAGAGGCCA GCAGCCCGTG GCCAAGCCCG AGGGAGCCC GACCGCC           1197
```

(2) INFORMATION FOR SEQ ID NO:8:

(i) SEQUENCE CHARACTERISTICS:
        (A) LENGTH: 399 amino acids
        (B) TYPE: amino acid
        (D) TOPOLOGY: linear (xi) SEQUENCE DESCRIPTION: SEQ ID NO:8:

```
Asp Ala Asp Met Lys Gly His Phe Asp Pro Ala Lys Cys Arg Tyr
 1               5                  10                  15

Ala Leu Gly Met Gln Asp Arg Thr Ile Pro Asp Ser Asp Ile Ser
                20                  25                  30

Ala Ser Ser Ser Trp Ser Asp Ser Thr Ala Ala Arg His Ser Arg
                35                  40                  45

Leu Glu Ser Ser Asp Gly Asp Gly Ala Trp Cys Pro Ala Gly Ser
                50                  55                  60

Val Phe Pro Lys Glu Glu Tyr Leu Gln Val Asp Leu Gln Arg
                65                  70                  75

Leu His Leu Val Ala Leu Val Gly Thr Gln Gly Arg His Ala Gly
                80                  85                  90

Gly Leu Gly Lys Glu Phe Ser Arg Ser Tyr Arg Leu Arg Tyr Ser
                95                 100                 105

Arg Asp Gly Arg Arg Trp Met Gly Trp Lys Asp Arg Trp Gly Gln
               110                 115                 120

Glu Val Ile Ser Gly Asn Glu Asp Pro Glu Gly Val Val Leu Lys
               125                 130                 135

Asp Leu Gly Pro Pro Met Val Ala Arg Leu Val Arg Phe Tyr Pro
               140                 145                 150

Arg Ala Asp Arg Val Met Ser Val Cys Leu Arg Val Glu Leu Tyr
               155                 160                 165

Gly Cys Leu Trp Arg Asp Gly Leu Leu Ser Tyr Thr Ala Pro Val
               170                 175                 180

Gly Gln Thr Met Tyr Leu Ser Glu Ala Val Tyr Leu Asn Asp Ser
               185                 190                 195

Thr Tyr Asp Gly His Thr Val Gly Gly Leu Gln Tyr Gly Gly Leu
               200                 205                 210

Gly Gln Leu Ala Asp Gly Val Val Gly Leu Asp Asp Phe Arg Lys
               215                 220                 225

Ser Gln Glu Leu Arg Val Trp Pro Gly Tyr Asp Tyr Val Gly Trp
               230                 235                 240

Ser Asn His Ser Phe Ser Ser Gly Tyr Val Glu Met Glu Phe Glu
               245                 250                 255

Phe Asp Arg Leu Arg Ala Phe Gln Ala Met Gln Val His Cys Asn
               260                 265                 270

Asn Met His Thr Leu Gly Ala Arg Leu Pro Gly Gly Val Glu Cys
               275                 280                 285

Arg Phe Arg Arg Gly Pro Ala Met Ala Trp Glu Gly Glu Pro Met
               290                 295                 300

Arg His Asn Leu Gly Gly Asn Leu Gly Asp Pro Arg Ala Arg Ala
               305                 310                 315

Val Ser Val Pro Leu Gly Gly Arg Val Ala Arg Phe Leu Gln Cys
               320                 325                 330

Arg Phe Leu Phe Ala Gly Pro Trp Leu Leu Phe Ser Glu Ile Ser
               335                 340                 345

Phe Ile Ser Asp Val Val Asn Asn Ser Pro Ala Leu Gly Gly
               350                 355                 360

Thr Phe Pro Pro Ala Pro Trp Trp Pro Pro Gly Pro Pro Thr
               365                 370                 375

Asn Phe Ser Ser Leu Glu Leu Glu Pro Arg Gly Gln Gln Pro Val
```

```
                     380             385            390
Ala Lys Pro Glu Gly Ser Pro Thr Ala
                     395             399

(2) INFORMATION FOR SEQ ID NO:9:

(i) SEQUENCE CHARACTERISTICS:
        (A) LENGTH: 3785 bases
        (B) TYPE: nucleic acid
        (C) STRANDEDNESS: single
        (D) TOPOLOGY: linear (xi) SEQUENCE DESCRIPTION: SEQ ID NO:9:

CCTCCGCCAC CCTCCTCTCA GCGCTCGCGG GCCGGGCCCG GCATGGTGCG           50

CGTCGCCGCC GATGGCGCTG AGGCGGAGCA TGGGGTGGCC GGGGCTCCGG          100

CCGCTGCTGC TGGCGGGACT GGCTTCTCTG CTGCTCCCCG GGTCTGCGGC          150

CGCAGGCCTG AAGCTCATGG GCGCCCCAGT GAAGATGACC GTGTCTCAGG          200

GGCAGCCAGT GAAGCTCAAC TGCAGCGTGG AGGGGATGGA GGACCCTGAC          250

ATCCACTGGA TGAAGGATGG CACCGTGGTC CAGAATGCAA GCCAGGTGTC          300

CATCTCCATC AGCGAGCACA GCTGGATTGG CTTACTCAGC CTAAAGTCAG          350

TGGAGCGGTC TGATGCTGGC CTGTACTGGT GCCAGGTGAA GGATGGGGAG          400

GAAACCAAGA TCTCTCAGTC AGTATGGCTC ACTGTCGAAG GTGTGCCATT          450

CTTCACAGTG GAACCAAAAG ATCTGGCGGT GCCACCCAAT GCCCCTTTTC          500

AGCTGTCTTG TGAGGCTGTG GGTCCTCCAG AACCCGTAAC CATTTACTGG          550

TGGAGAGGAC TCACTAAGGT TGGGGGACCT GCTCCCTCTC CCTCTGTTTT          600

AAATGTGACA GGAGTGACCC AGCGCACAGA GTTTTCTTGT GAAGCCCGCA          650

ACATAAAAGG CCTGGCCACT TCCCGACCAG CCATTGTTCG CCTTCAAGCA          700

CCGCCTGCAG CTCCTTTCAA CACCACAGTA ACAACGATCT CCAGCTACAA          750

CGCTAGCGTG GCCTGGGTGC CAGGTGCTGA CGGCCTAGCT CTGCTGCATT          800

CCTGTACTGT ACAGGTGGCA CACGCCCCAG GAGAATGGGA GGCCCTTGCT          850

GTTGTGGTTC CTGTGCCACC TTTTACCTGC CTGCTTCGGA ACTTGGCCCC          900

TGCCACCAAC TACAGCCTTA GGGTGCGCTG TGCCAATGCC TTGGGCCCTT          950

CTCCCTACGG CGACTGGGTG CCCTTTCAGA CAAAGGGCCT AGCGCCAGCC         1000

AGAGCTCCTC AGAATTTCCA TGCCATTCGT ACCGACTCAG GCCTTATCCT         1050

GGAATGGGAA GAAGTGATTC CTGAAGACCC TGGGGAAGGC CCCCTAGGAC         1100

CTTATAAGCT GTCCTGGGTC AAGAAAAATG GAACCCAGGA TGAGCTGATG         1150

GTGGAAGGGA CCAGGGCCAA TCTGACCGAC TGGGATCCCC AGAAGGACCT         1200

GATTTTGCGT GTGTGTGCCT CCAATGCAAT TGGTGATGGG CCCTGGAGTC         1250

AGCCACTGGT GGTGTCTTCT CATGACCATG CAGGGAGGCA GGGCCCTCCC         1300

CACAGCCGCA CATCCTGGGT GCCTGTGGTC CTGGGCGTGC TCACCGCCCT         1350

GATCACAGCT GCTGCCTTGG CCCTCATCCT GCTTCGGAAG AGACGCAAGG         1400

AGACGCGTTT CGGGCAAGCC TTTGACAGTG TCATGGCCCG AGGGGAGCCA         1450

GCTGTACACT TCCGGGCAGC CCGATCTTTC AATCGAGAAA GGCCTGAACG         1500

CATTGAGGCC ACATTGGATA GCCTGGGCAT CAGCGATGAA TTGAAGGAAA         1550

AGCTGGAGGA TGTCCTCATT CCAGAGCAGC AGTTCACCCT CGGTCGGATG         1600
```

```
TTGGGCAAAG GAGAGTTTGG ATCAGTGCGG GAAGCCCAGC TAAAGCAGGA          1650

AGATGGCTCC TTCGTGAAAG TGGCAGTGAA GATGCTGAAA GCTGACATCA          1700

TTGCCTCAAG CGACATAGAA GAGTTCCTCC GGGAAGCAGC TTGCATGAAG          1750

GAGTTTGACC ATCCACACGT GGCCAAGCTT GTTGGGGTGA GCCTCCGGAG          1800

CAGGGCTAAA GGTCGTCTCC CCATTCCCAT GGTCATCCTG CCCTTCATGA          1850

AACATGGAGA CTTGCACGCC TTTCTGCTCG CCTCCCGAAT CGGGGAGAAC          1900

CCTTTTAACC TGCCCCTGCA GACCCTGGTC CGGTTCATGG TGGACATTGC          1950

CTGTGGCATG GAGTACCTGA GCTCCCGGAA CTTCATCCAC CGAGACCTAG          2000

CAGCTCGGAA TTGCATGCTG GCCGAGGACA TGACAGTGTG TGTGGCTGAT          2050

TTTGGACTCT CTCGGAAAAT CTATAGCGGG GACTATTATC GTCAGGGCTG          2100

TGCCTCCAAA TTGCCCGTCA AGTGGCTGGC CCTGGAGAGC TTGGCTGACA          2150

ACTTGTATAC TGTACACAGT GATGTGTGGG CCTTCGGGGT GACCATGTGG          2200

GAGATCATGA CTCGTGGGCA GACGCCATAT GCTGGCATTG AAAATGCTGA          2250

GATTTACAAC TACCTCATCG GCGGGAACCG CCTGAAGCAG CCTCCGGAGT          2300

GCATGGAGGA AGTGTATGAT CTCATGTACC AGTGCTGGAG CGCCGACCCC          2350

AAGCAGCGCC CAAGCTTCAC GTGTCTGCGA ATGGAACTGG AGAACATTCT          2400

GGGCCACCTG TCTGTGCTGT CCACCAGCCA GGACCCCTTG TACATCAACA          2450

TTGAGAGAGC TGAGCAGCCT ACTGAGAGTG GCAGCCCTGA GCTGCACTGT          2500

GGAGAGCGAT CCAGCAGCGA GGCAGGGGAC GGCAGTGGCG TGGGGGCAGT          2550

AGGTGGCATC CCCAGTGACT CTCGGTACAT CTTCAGCCCC GGAGGGCTAT          2600

CCGAGTCACC AGGGCAGCTG GAGCAGCAGC CAGAAAGCCC CCTCAATGAG          2650

AACCAGAGGC TGTTGTTGCT GCAGCAAGGG CTACTGCCTC ACAGTAGCTG          2700

TTAACCCTCA GGCAGAGGAA AGTTGGGGCC CCTGGCTCTG CTGACCGCTG          2750

CGCTGCCTGA CTAGGCCCAG TCTGATCACA GCCCAGGCAG CAAGGTATGG          2800

AGGCTCCTGT GGTAGCCCTC CCAAGCTGTG TGGCGCCTGG ACGGACCAAA          2850

TTGCCCAATC CCAGTTCTTC CTGCAGCCGC TCTGGCCAGC CTGGCATCAG          2900

TTCAGGCCTT GGCTTAGAGG AGGTGAGCCA GAGCTGGTTG CCTGAATGCA          2950

GGCAGCTGGC AGGAGGGGAG GGTGGCTATG TTTCCATGGG TACCATGGGT          3000

GTGGATGGCA GTAAGGGAGG GTAGCAACAG CCTGTGGGCC CCTACCCTCC          3050

TGGCTGAGCT GCTCCTACTT TAGTGCATGC TTGGAGCCGC CTGCAGCCTG          3100

GAACTCAGCA CTGCCCACCA CACTTGGGCC GAAATGCCAG GTTTGCCCCT          3150

CTTAAGTCAC AAAGAGATGT CCATGTATTG TTCCCTTTTA GGTGATGATT          3200

AGGAAGGGAT TGGCACACTT GGGTCCCTAA GCCCTATGGC AGGAAATGGT          3250

GGGATATTCT CAGGTCTGAA TCCTCATCAT CTTCCTGATT CCCCACCCTG          3300

CAAAGGCCTG GAACTGGCTG TGGGGCTCTG ACGCATGCTG AAGGACAAAA          3350

GGTTACAGAG ATCCGACTTC AAAAGGCAGG GTCTGAGTCT GGCAGGTGGA          3400

GAGGTGCTAA GGGGCTGGCC CAGGAGTCAG GCATTTCAGG ACCCCTCCAA          3450

GCTTCTACAG TCTGTCTGAG CATGCTACCA AGCCCCCAGA TACCCCAAAA          3500

CTAACAGAGG CAGTTTTGTC TGAGCCCAGC CCTCCCACAT GATGACCCTT          3550
```

```
AGGTCTACCC TCCTCTCTAA ATGGACATCC TCGTTTGTCC CAAGTCTCCA          3600

GAGAGACTAC TGATGGCTGA TGTGGGTAAG AAAAGTTCCA GGAACCAGGG          3650

CTGGGGTGGA ACCAGGGCTG GGGTCGAGGC AGGCTCTTGG GCAGGCTCTT          3700

GCTGTTAGGA ACATTTCTAA GCTATTAAGT TGCTGTTTCA AAACAAATAA          3750

AATTGAAACA TAAAGAATCA AAAAAAAAAA AAAAA                          3785
```

(2) INFORMATION FOR SEQ ID NO:10:

(i) SEQUENCE CHARACTERISTICS:
        (A) LENGTH: 880 amino acids
        (B) TYPE: amino acid
        (D) TOPOLOGY: linear (xi) SEQUENCE DESCRIPTION: SEQ ID NO:10:

```
Met Ala Leu Arg Arg Ser Met Gly Trp Pro Gly Leu Arg Pro Leu
 1               5                  10                  15

Leu Leu Ala Gly Leu Ala Ser Leu Leu Pro Gly Ser Ala Ala
                20                  25                  30

Ala Gly Leu Lys Leu Met Gly Ala Pro Val Lys Met Thr Val Ser
                35                  40                  45

Gln Gly Gln Pro Val Lys Leu Asn Cys Ser Val Glu Gly Met Glu
                50                  55                  60

Asp Pro Asp Ile His Trp Met Lys Asp Gly Thr Val Val Gln Asn
                65                  70                  75

Ala Ser Gln Val Ser Ile Ser Ile Ser Glu His Ser Trp Ile Gly
                80                  85                  90

Leu Leu Ser Leu Lys Ser Val Glu Arg Ser Asp Ala Gly Leu Tyr
                95                  100                 105

Trp Cys Gln Val Lys Asp Gly Glu Glu Thr Lys Ile Ser Gln Ser
                110                 115                 120

Val Trp Leu Thr Val Glu Gly Val Pro Phe Phe Thr Val Glu Pro
                125                 130                 135

Lys Asp Leu Ala Val Pro Pro Asn Ala Pro Phe Gln Leu Ser Cys
                140                 145                 150

Glu Ala Val Gly Pro Pro Glu Pro Val Thr Ile Tyr Trp Trp Arg
                155                 160                 165

Gly Leu Thr Lys Val Gly Gly Pro Ala Pro Ser Pro Ser Val Leu
                170                 175                 180

Asn Val Thr Gly Val Thr Gln Arg Thr Glu Phe Ser Cys Glu Ala
                185                 190                 195

Arg Asn Ile Lys Gly Leu Ala Thr Ser Arg Pro Ala Ile Val Arg
                200                 205                 210

Leu Gln Ala Pro Pro Ala Ala Pro Phe Asn Thr Thr Val Thr Thr
                215                 220                 225

Ile Ser Ser Tyr Asn Ala Ser Val Ala Trp Val Pro Gly Ala Asp
                230                 235                 240

Gly Leu Ala Leu Leu His Ser Cys Thr Val Gln Val Ala His Ala
                245                 250                 255

Pro Gly Glu Trp Glu Ala Leu Ala Val Val Val Pro Val Pro Pro
                260                 265                 270

Phe Thr Cys Leu Leu Arg Asn Leu Ala Pro Ala Thr Asn Tyr Ser
                275                 280                 285

Leu Arg Val Arg Cys Ala Asn Ala Leu Gly Pro Ser Pro Tyr Gly
                290                 295                 300
```

-continued

```
Asp Trp Val Pro Phe Gln Thr Lys Gly Leu Ala Pro Ala Arg Ala
        305                 310                 315
Pro Gln Asn Phe His Ala Ile Arg Thr Asp Ser Gly Leu Ile Leu
        320                 325                 330
Glu Trp Glu Glu Val Ile Pro Glu Asp Pro Gly Glu Gly Pro Leu
        335                 340                 345
Gly Pro Tyr Lys Leu Ser Trp Val Gln Glu Asn Gly Thr Gln Asp
        350                 355                 360
Glu Leu Met Val Glu Gly Thr Arg Ala Asn Leu Thr Asp Trp Asp
        365                 370                 375
Pro Gln Lys Asp Leu Ile Leu Arg Val Cys Ala Ser Asn Ala Ile
        380                 385                 390
Gly Asp Gly Pro Trp Ser Gln Pro Leu Val Val Ser Ser His Asp
        395                 400                 405
His Ala Gly Arg Gln Gly Pro Pro His Ser Arg Thr Ser Trp Val
        410                 415                 420
Pro Val Val Leu Gly Val Leu Thr Ala Leu Ile Thr Ala Ala Ala
        425                 430                 435
Leu Ala Leu Ile Leu Leu Arg Lys Arg Lys Glu Thr Arg Phe
        440                 445                 450
Gly Gln Ala Phe Asp Ser Val Met Ala Arg Gly Glu Pro Ala Val
        455                 460                 465
His Phe Arg Ala Ala Arg Ser Phe Asn Arg Glu Arg Pro Glu Arg
        470                 475                 480
Ile Glu Ala Thr Leu Asp Ser Leu Gly Ile Ser Asp Glu Leu Lys
        485                 490                 495
Glu Lys Leu Glu Asp Val Leu Ile Pro Glu Gln Gln Phe Thr Leu
        500                 505                 510
Gly Arg Met Leu Gly Lys Gly Glu Phe Gly Ser Val Arg Glu Ala
        515                 520                 525
Gln Leu Lys Gln Glu Asp Gly Ser Phe Val Lys Val Ala Val Lys
        530                 535                 540
Met Leu Lys Ala Asp Ile Ile Ala Ser Ser Asp Ile Glu Glu Phe
        545                 550                 555
Leu Arg Glu Ala Ala Cys Met Lys Glu Phe Asp His Pro His Val
        560                 565                 570
Ala Lys Leu Val Gly Val Ser Leu Arg Ser Arg Ala Lys Gly Arg
        575                 580                 585
Leu Pro Ile Pro Met Val Ile Leu Pro Phe Met Lys His Gly Asp
        590                 595                 600
Leu His Ala Phe Leu Leu Ala Ser Arg Ile Gly Glu Asn Pro Phe
        605                 610                 615
Asn Leu Pro Leu Gln Thr Leu Val Arg Phe Met Val Asp Ile Ala
        620                 625                 630
Cys Gly Met Glu Tyr Leu Ser Ser Arg Asn Phe Ile His Arg Asp
        635                 640                 645
Leu Ala Ala Arg Asn Cys Met Leu Ala Glu Asp Met Thr Val Cys
        650                 655                 660
Val Ala Asp Phe Gly Leu Ser Arg Lys Ile Tyr Ser Gly Asp Tyr
        665                 670                 675
Tyr Arg Gln Gly Cys Ala Ser Lys Leu Pro Val Lys Trp Leu Ala
        680                 685                 690
```

```
Leu Glu Ser Leu Ala Asp Asn Leu Tyr Thr Val His Ser Asp Val
            695                 700                 705

Trp Ala Phe Gly Val Thr Met Trp Glu Ile Met Thr Arg Gly Gln
            710                 715                 720

Thr Pro Tyr Ala Gly Ile Glu Asn Ala Glu Ile Tyr Asn Tyr Leu
            725                 730                 735

Ile Gly Gly Asn Arg Leu Lys Gln Pro Pro Glu Cys Met Glu Glu
            740                 745                 750

Val Tyr Asp Leu Met Tyr Gln Cys Trp Ser Ala Asp Pro Lys Gln
            755                 760                 765

Arg Pro Ser Phe Thr Cys Leu Arg Met Glu Leu Glu Asn Ile Leu
            770                 775                 780

Gly His Leu Ser Val Leu Ser Thr Ser Gln Asp Pro Leu Tyr Ile
            785                 790                 795

Asn Ile Glu Arg Ala Glu Gln Pro Thr Glu Ser Gly Ser Pro Glu
            800                 805                 810

Leu His Cys Gly Glu Arg Ser Ser Ser Glu Ala Gly Asp Gly Ser
            815                 820                 825

Gly Val Gly Ala Val Gly Gly Ile Pro Ser Asp Ser Arg Tyr Ile
            830                 835                 840

Phe Ser Pro Gly Gly Leu Ser Glu Ser Pro Gly Gln Leu Glu Gln
            845                 850                 855

Gln Pro Glu Ser Pro Leu Asn Glu Asn Gln Arg Leu Leu Leu Leu
            860                 865                 870

Gln Gln Gly Leu Leu Pro His Ser Ser Cys
            875                 880
```

(2) INFORMATION FOR SEQ ID NO:11:

(i) SEQUENCE CHARACTERISTICS:
        (A) LENGTH: 1164 bases
        (B) TYPE: nucleic acid
        (C) STRANDEDNESS: single
        (D) TOPOLOGY: linear (xi) SEQUENCE DESCRIPTION: SEQ ID NO:11:

```
GCAGGCCTGA AGCTCATGGG CGCCCCAGTG AAGATGACCG TGTCTCAGGG            50

GCAGCCAGTG AAGCTCAACT GCAGCGTGGA GGGGATGGAG GACCCTGACA           100

TCCACTGGAT GAAGGATGGC ACCGTGGTCC AGAATGCAAG CCAGGTGTCC           150

ATCTCCATCA GCGAGCACAG CTGGATTGGC TTACTCAGCC TAAAGTCAGT           200

GGAGCGGTCT GATGCTGGCC TGTACTGGTG CCAGGTGAAG GATGGGGAGG           250

AAACCAAGAT CTCTCAGTCA GTATGGCTCA CTGTCGAAGG TGTGCCATTC           300

TTCACAGTGG AACCAAAAGA TCTGGCGGTG CCACCCAATG CCCCTTTTCA           350

GCTGTCTTGT GAGGCTGTGG GTCCTCCAGA ACCCGTAACC ATTTACTGGT           400

GGAGAGGACT CACTAAGGTT GGGGGACCTG CTCCCTCTCC CTCTGTTTTA           450

AATGTGACAG GAGTGACCCA GCGCACAGAG TTTTCTTGTG AAGCCCGCAA           500

CATAAAAGGC CTGGCCACTT CCCGACCAGC CATTGTTCGC CTTCAAGCAC           550

CGCCTGCAGC TCCTTTCAAC ACCACAGTAA CAACGATCTC CAGCTACAAC           600

GCTAGCGTGG CCTGGGTGCC AGGTGCTGAC GGCCTAGCTC TGCTGCATTC           650

CTGTACTGTA CAGGTGGCAC ACGCCCAGG AGAATGGGAG GCCCTTGCTG            700

TTGTGGTTCC TGTGCCACCT TTTACCTGCC TGCTTCGGAA CTTGGCCCCT           750
```

```
GCCACCAACT ACAGCCTTAG GGTGCGCTGT GCCAATGCCT TGGGCCCTTC         800

TCCCTACGGC GACTGGGTGC CCTTTCAGAC AAAGGGCCTA GCGCCAGCCA         850

GAGCTCCTCA GAATTTCCAT GCCATTCGTA CCGACTCAGG CCTTATCCTG         900

GAATGGGAAG AAGTGATTCC TGAAGACCCT GGGGAAGGCC CCCTAGGACC         950

TTATAAGCTG TCCTGGGTCC AAGAAAATGG AACCCAGGAT GAGCTGATGG        1000

TGGAAGGGAC CAGGGCCAAT CTGACCGACT GGGATCCCCA GAAGGACCTG        1050

ATTTTGCGTG TGTGTGCCTC CAATGCAATT GGTGATGGGC CCTGGAGTCA        1100

GCCACTGGTG GTGTCTTCTC ATGACCATGC AGGGAGGCAG GGCCCTCCCC        1150

ACAGCCGCAC ATCC                                               1164
```

(2) INFORMATION FOR SEQ ID NO:12:

(i) SEQUENCE CHARACTERISTICS:
        (A) LENGTH: 388 amino acids
        (B) TYPE: amino acid
        (D) TOPOLOGY: linear (xi) SEQUENCE DESCRIPTION: SEQ ID NO:12:

```
Ala Gly Leu Lys Leu Met Gly Ala Pro Val Lys Met Thr Val Ser
 1               5                  10                  15

Gln Gly Gln Pro Val Lys Leu Asn Cys Ser Val Glu Gly Met Glu
                20                  25                  30

Asp Pro Asp Ile His Trp Met Lys Asp Gly Thr Val Val Gln Asn
                35                  40                  45

Ala Ser Gln Val Ser Ile Ser Ile Ser Glu His Ser Trp Ile Gly
                50                  55                  60

Leu Leu Ser Leu Lys Ser Val Glu Arg Ser Asp Ala Gly Leu Tyr
                65                  70                  75

Trp Cys Gln Val Lys Asp Gly Glu Glu Thr Lys Ile Ser Gln Ser
                80                  85                  90

Val Trp Leu Thr Val Glu Gly Val Pro Phe Phe Thr Val Glu Pro
                95                 100                 105

Lys Asp Leu Ala Val Pro Pro Asn Ala Pro Phe Gln Leu Ser Cys
               110                 115                 120

Glu Ala Val Gly Pro Pro Glu Pro Val Thr Ile Tyr Trp Trp Arg
               125                 130                 135

Gly Leu Thr Lys Val Gly Gly Pro Ala Pro Ser Pro Ser Val Leu
               140                 145                 150

Asn Val Thr Gly Val Thr Gln Arg Thr Glu Phe Ser Cys Glu Ala
               155                 160                 165

Arg Asn Ile Lys Gly Leu Ala Thr Ser Arg Pro Ala Ile Val Arg
               170                 175                 180

Leu Gln Ala Pro Pro Ala Ala Pro Phe Asn Thr Val Thr Thr
               185                 190                 195

Ile Ser Ser Tyr Asn Ala Ser Val Ala Trp Val Pro Gly Ala Asp
               200                 205                 210

Gly Leu Ala Leu Leu His Ser Cys Thr Val Gln Val Ala His Ala
               215                 220                 225

Pro Gly Glu Trp Glu Ala Leu Ala Val Val Pro Val Pro Pro
               230                 235                 240

Phe Thr Cys Leu Leu Arg Asn Leu Ala Pro Ala Thr Asn Tyr Ser
               245                 250                 255
```

```
Leu Arg Val Arg Cys Ala Asn Ala Leu Gly Pro Ser Pro Tyr Gly
            260                 265                 270

Asp Trp Val Pro Phe Gln Thr Lys Gly Leu Ala Pro Ala Arg Ala
            275                 280                 285

Pro Gln Asn Phe His Ala Ile Arg Thr Asp Ser Gly Leu Ile Leu
            290                 295                 300

Glu Trp Glu Glu Val Ile Pro Glu Asp Pro Gly Glu Gly Pro Leu
            305                 310                 315

Gly Pro Tyr Lys Leu Ser Trp Val Gln Glu Asn Gly Thr Gln Asp
            320                 325                 330

Glu Leu Met Val Glu Gly Thr Arg Ala Asn Leu Thr Asp Trp Asp
            335                 340                 345

Pro Gln Lys Asp Leu Ile Leu Arg Val Cys Ala Ser Asn Ala Ile
            350                 355                 360

Gly Asp Gly Pro Trp Ser Gln Pro Leu Val Val Ser Ser His Asp
            365                 370                 375

His Ala Gly Arg Gln Gly Pro Pro His Ser Arg Thr Ser
            380                 385     388
```

(2) INFORMATION FOR SEQ ID NO:13:

(i) SEQUENCE CHARACTERISTICS:
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:13:

CGGATCCACA CGATGCGACT CTT                            23

(2) INFORMATION FOR SEQ ID NO:14:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:14:

GGAATTCCTC TCATGGAGCT AGTCCATCTC T                    31

(2) INFORMATION FOR SEQ ID NO:15:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:15:

CGGATCCATC CACAGAGATG T                              21

(2) INFORMATION FOR SEQ ID NO:16:

(i) SEQUENCE CHARACTERISTICS:
        (A) LENGTH: 25 bases
        (B) TYPE: nucleic acid
        (C) STRANDEDNESS: single
        (D) TOPOLOGY: linear (xi) SEQUENCE DESCRIPTION: SEQ ID NO:16:

GGAATTCCAA AGGACCAGCA CGATC                        25

(2) INFORMATION FOR SEQ ID NO:17:

(i) SEQUENCE CHARACTERISTICS:
        (A) LENGTH: 40 bases
        (B) TYPE: nucleic acid
        (C) STRANDEDNESS: single
        (D) TOPOLOGY: linear (xi) SEQUENCE DESCRIPTION: SEQ ID NO:17:

```
GACCGTGTGT GTGGCTGACT TTGGACTCTC CTGGAAGATC                    40
```

(2) INFORMATION FOR SEQ ID NO:18:

(i) SEQUENCE CHARACTERISTICS:
        (A) LENGTH: 40 bases
        (B) TYPE: nucleic acid
        (C) STRANDEDNESS: single
        (D) TOPOLOGY: linear (xi) SEQUENCE DESCRIPTION: SEQ ID NO:18:

```
GGCTGTGCCT CCAAATTGCC CGTCAAGTGG CTGGCCCTGG                    40
```

(2) INFORMATION FOR SEQ ID NO:19:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO:19:

```
AGCCGGTGAA GCTGAACTGC AGTGTGGAGG GGATGGAGGA GCCTGACATC         50
```

(2) INFORMATION FOR SEQ ID NO:20:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO:20:

```
TCCAGCTACA ACGCTAGCGT GGCCTGGGTG CCAGGTGCTG ACGGCCTAGC         50
```

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:21:

```
Ile His Arg Asp Leu Ala Ala Arg Asn
 1               5               9
```

(2) INFORMATION FOR SEQ ID NO:22:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:22:

```
Lys Trp Ile Ala Ile Glu
 1               5   6
```

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:23:

Lys Thr Trp Thr Met Ala Pro Glu
 1           5          8

(2) INFORMATION FOR SEQ ID NO:24:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:24:

Lys Trp Leu Ala Leu Glu
 1         5  6

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:25:

Lys Trp Met Ala Leu Glu
 1         5  6

(2) INFORMATION FOR SEQ ID NO:26:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:26:

CAGCTGCTCG AGGCAGGTCT GAAGCTCATG                      30

(2) INFORMATION FOR SEQ ID NO:27:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:27:

GCATGAATTC ATGGCACACC TTCTACCGTG                      30

(2) INFORMATION FOR SEQ ID NO:28:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:28:

CACTGAGCTG GCTGACTAAG                                   20

(2) INFORMATION FOR SEQ ID NO:29:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:29:

CCTGATAGGC TGGGTACTCC                                                          20

(2) INFORMATION FOR SEQ ID NO:30:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:30:

AAGCCCGGAC TGACCAAA                                                            18

(2) INFORMATION FOR SEQ ID NO:31:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:31:

GTGCGGAATC AGAAAGATGG                                                      20

(2) INFORMATION FOR SEQ ID NO:32:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:32:

TCAAGACAAT GGAACCCA                                                           18

(2) INFORMATION FOR SEQ ID NO:33:

(i) SEQUENCE CHARACTERISTICS:
        (A) LENGTH: 36 bases
        (B) TYPE: nucleic acid
        (C) STRANDEDNESS: single
        (D) TOPOLOGY: linear (xi) SEQUENCE DESCRIPTION: SEQ ID NO:33:

CATGGAATTC GGTGACCGAT GTGCGGCTGT GAGGAG                            36

(2) INFORMATION FOR SEQ ID NO:34:

(i) SEQUENCE CHARACTERISTICS:
        (A) LENGTH: 894 amino acids
        (B) TYPE: amino acid
        (D) TOPOLOGY: linear (xi) SEQUENCE DESCRIPTION: SEQ ID NO:34:

Met Ala Trp Arg Cys Pro Arg Met Gly Arg Val Pro Leu Ala Trp
 1            5                 10              15

Cys Leu Ala Leu Cys Gly Trp Ala Cys Met Ala Pro Arg Gly Thr
            20                25              30

-continued

```
Gln Ala Glu Glu Ser Pro Phe Val Gly Asn Pro Gly Asn Ile Thr
                 35                  40                  45

Gly Ala Arg Gly Leu Thr Gly Thr Leu Arg Cys Gln Leu Gln Val
             50                  55                  60

Gln Gly Glu Pro Pro Glu Val His Trp Leu Arg Asp Gly Gln Ile
             65                  70                  75

Leu Glu Leu Ala Asp Ser Thr Gln Thr Gln Val Pro Leu Gly Glu
             80                  85                  90

Asp Glu Gln Asp Asp Trp Ile Val Val Ser Gln Leu Arg Ile Thr
             95                 100                 105

Ser Leu Gln Leu Ser Asp Thr Gly Gln Tyr Gln Cys Leu Val Phe
            110                 115                 120

Leu Gly His Gln Thr Phe Val Ser Gln Pro Gly Tyr Val Gly Leu
            125                 130                 135

Glu Gly Leu Pro Tyr Phe Leu Glu Gly Pro Glu Asp Arg Thr Val
            140                 145                 150

Ala Ala Asn Thr Pro Phe Asn Leu Ser Cys Gln Ala Gln Gly Pro
            155                 160                 165

Pro Glu Pro Val Asp Leu Leu Trp Leu Gln Asp Ala Val Pro Leu
            170                 175                 180

Ala Thr Ala Pro Gly His Gly Pro Gln Arg Ser Leu His Val Pro
            185                 190                 195

Gly Leu Asn Lys Thr Ser Ser Phe Ser Cys Glu Ala His Asn Ala
            200                 205                 210

Lys Gly Val Thr Thr Ser Arg Thr Ala Thr Ile Thr Val Leu Pro
            215                 220                 225

Gln Gln Pro Arg Asn Leu His Leu Val Ser Arg Gln Pro Thr Glu
            230                 235                 240

Leu Glu Val Ala Trp Thr Pro Gly Leu Ser Gly Ile Tyr Pro Leu
            245                 250                 255

Thr His Cys Thr Leu Gln Ala Val Leu Ser Asp Asp Gly Met Gly
            260                 265                 270

Ile Gln Ala Gly Glu Pro Asp Pro Glu Glu Pro Leu Thr Ser
            275                 280                 285

Gln Ala Ser Val Pro Pro His Gln Leu Arg Leu Gly Ser Leu His
            290                 295                 300

Pro His Thr Pro Tyr His Ile Arg Val Ala Cys Thr Ser Ser Gln
            305                 310                 315

Gly Pro Ser Ser Trp Thr His Trp Leu Pro Val Glu Thr Pro Glu
            320                 325                 330

Gly Val Pro Leu Gly Pro Pro Glu Asn Ile Ser Ala Thr Arg Asn
            335                 340                 345

Gly Ser Gln Ala Phe Val His Trp Gln Glu Pro Arg Ala Pro Leu
            350                 355                 360

Gln Gly Thr Leu Leu Gly Tyr Arg Leu Ala Tyr Gln Gly Gln Asp
            365                 370                 375

Thr Pro Glu Val Leu Met Asp Ile Gly Leu Arg Gln Glu Val Thr
            380                 385                 390

Leu Glu Leu Gln Gly Asp Gly Ser Val Ser Asn Leu Thr Val Cys
            395                 400                 405

Val Ala Ala Tyr Thr Ala Ala Gly Asp Gly Pro Trp Ser Leu Pro
            410                 415                 420
```

-continued

Val Pro Leu Glu Ala Trp Arg Pro Gly Gln Ala Gln Pro Val His
            425                 430                 435

Gln Leu Val Lys Glu Pro Ser Thr Pro Ala Phe Ser Trp Pro Trp
            440                 445                 450

Trp Tyr Val Leu Leu Gly Ala Val Ala Ala Cys Val Leu
            455                 460                 465

Ile Leu Ala Leu Phe Leu Val His Arg Lys Lys Glu Thr Arg
            470                 475                 480

Tyr Gly Glu Val Phe Glu Pro Thr Val Glu Arg Gly Glu Leu Val
            485                 490                 495

Val Arg Tyr Arg Val Arg Lys Ser Tyr Ser Arg Arg Thr Thr Glu
            500                 505                 510

Ala Thr Leu Asn Ser Leu Gly Ile Ser Glu Glu Leu Lys Glu Lys
            515                 520                 525

Leu Arg Asp Val Met Val Asp Arg His Lys Val Ala Leu Gly Lys
            530                 535                 540

Thr Leu Gly Glu Gly Glu Phe Gly Ala Val Met Glu Gly Gln Leu
            545                 550                 555

Asn Gln Asp Asp Ser Ile Leu Lys Val Ala Val Lys Thr Met Lys
            560                 565                 570

Ile Ala Ile Cys Thr Arg Ser Glu Leu Glu Asp Phe Leu Ser Glu
            575                 580                 585

Ala Val Cys Met Lys Glu Phe Asp His Pro Asn Val Met Arg Leu
            590                 595                 600

Ile Gly Val Cys Phe Gln Gly Ser Glu Arg Glu Ser Phe Pro Ala
            605                 610                 615

Pro Val Val Ile Leu Pro Phe Met Lys His Gly Asp Leu His Ser
            620                 625                 630

Phe Leu Leu Tyr Ser Arg Leu Gly Asp Gln Pro Val Tyr Leu Pro
            635                 640                 645

Thr Gln Met Leu Val Lys Phe Met Ala Asp Ile Ala Ser Gly Met
            650                 655                 660

Glu Tyr Leu Ser Thr Lys Arg Phe Ile His Arg Asp Leu Ala Ala
            665                 670                 675

Arg Asn Cys Met Leu Asn Glu Asn Met Ser Val Cys Val Ala Asp
            680                 685                 690

Phe Gly Leu Ser Lys Lys Ile Tyr Asn Gly Asp Tyr Tyr Arg Gln
            695                 700                 705

Gly Arg Ile Ala Lys Met Pro Val Lys Trp Ile Ala Ile Glu Ser
            710                 715                 720

Leu Ala Asp Arg Val Tyr Thr Ser Lys Ser Asp Val Trp Ser Phe
            725                 730                 735

Gly Val Thr Met Trp Glu Ile Ala Thr Arg Gly Gln Thr Pro Tyr
            740                 745                 750

Pro Gly Val Glu Asn Ser Glu Ile Tyr Asp Tyr Leu Arg Gln Gly
            755                 760                 765

Asn Arg Leu Lys Gln Pro Ala Asp Cys Leu Asp Gly Leu Tyr Ala
            770                 775                 780

Leu Met Ser Arg Cys Trp Glu Leu Asn Pro Gln Asp Arg Pro Ser
            785                 790                 795

Phe Thr Glu Leu Arg Glu Asp Leu Glu Asn Thr Leu Lys Ala Leu
            800                 805                 810

Pro Pro Ala Gln Glu Pro Asp Glu Ile Leu Tyr Val Asn Met Asp

-continued

```
                815                 820                 825

Glu Gly Gly Gly Tyr Pro Glu Pro Pro Gly Ala Ala Gly Gly Ala
                830                 835                 840

Asp Pro Pro Thr Gln Pro Asp Pro Lys Asp Ser Cys Ser Cys Leu
                845                 850                 855

Thr Ala Ala Glu Val His Pro Ala Gly Arg Tyr Val Leu Cys Pro
                860                 865                 870

Ser Thr Thr Pro Ser Pro Ala Gln Pro Ala Asp Arg Gly Ser Pro
                875                 880                 885

Ala Ala Pro Gly Gln Glu Asp Gly Ala
                890                 894

(2) INFORMATION FOR SEQ ID NO:35:

(i) SEQUENCE CHARACTERISTICS:
        (A) LENGTH: 888 amino acids
        (B) TYPE: amino acid
        (D) TOPOLOGY: linear (xi) SEQUENCE DESCRIPTION: SEQ ID NO:35:

Met Gly Arg Val Pro Leu Ala Trp Trp Leu Ala Leu Cys Cys Trp
 1               5                  10                  15

Gly Cys Ala Ala His Lys Asp Thr Gln Thr Glu Ala Gly Ser Pro
                20                  25                  30

Phe Val Gly Asn Pro Gly Asn Ile Thr Gly Ala Arg Gly Leu Thr
                35                  40                  45

Gly Thr Leu Arg Cys Glu Leu Gln Val Gln Gly Glu Pro Pro Glu
                50                  55                  60

Val Val Trp Leu Arg Asp Gly Gln Ile Leu Glu Leu Ala Asp Asn
                65                  70                  75

Thr Gln Thr Gln Val Pro Leu Gly Glu Asp Trp Gln Asp Glu Trp
                80                  85                  90

Lys Val Val Ser Gln Leu Arg Ile Ser Ala Leu Gln Leu Ser Asp
                95                  100                 105

Ala Gly Glu Tyr Gln Cys Met Val His Leu Glu Gly Arg Thr Phe
                110                 115                 120

Val Ser Gln Pro Gly Phe Val Gly Leu Glu Gly Leu Pro Tyr Phe
                125                 130                 135

Leu Glu Glu Pro Glu Asp Lys Ala Val Pro Ala Asn Thr Pro Phe
                140                 145                 150

Asn Leu Ser Cys Gln Ala Gln Gly Pro Pro Glu Pro Val Thr Leu
                155                 160                 165

Leu Trp Leu Gln Asp Ala Val Pro Leu Ala Pro Val Thr Gly His
                170                 175                 180

Ser Ser Gln His Ser Leu Gln Thr Pro Gly Leu Asn Lys Thr Ser
                185                 190                 195

Ser Phe Ser Cys Glu Ala His Asn Ala Lys Gly Val Thr Thr Ser
                200                 205                 210

Arg Thr Ala Thr Ile Thr Val Leu Pro Gln Arg Pro His His Leu
                215                 220                 225

His Val Val Ser Arg Gln Pro Thr Glu Leu Glu Val Ala Trp Thr
                230                 235                 240

Pro Gly Leu Ser Gly Ile Tyr Pro Leu Thr His Cys Asn Leu Gln
                245                 250                 255

Ala Val Leu Ser Asp Asp Gly Val Gly Ile Trp Leu Gly Lys Ser
```

-continued

```
                260                 265                 270
Asp Pro Pro Glu Asp Pro Leu Thr Leu Gln Val Ser Val Pro Pro
                275                 280                 285
His Gln Leu Arg Leu Glu Lys Leu Leu Pro His Thr Pro Tyr His
                290                 295                 300
Ile Arg Ile Ser Cys Ser Ser Ser Gln Gly Pro Ser Pro Trp Thr
                305                 310                 315
His Trp Leu Pro Val Glu Thr Thr Glu Gly Val Pro Leu Gly Pro
                320                 325                 330
Pro Glu Asn Val Ser Ala Met Arg Asn Gly Ser Gln Val Leu Val
                335                 340                 345
Arg Trp Gln Glu Pro Arg Val Pro Leu Gln Gly Thr Leu Leu Gly
                350                 355                 360
Tyr Arg Leu Ala Tyr Arg Gly Gln Asp Thr Pro Glu Val Leu Met
                365                 370                 375
Asp Ile Gly Leu Thr Arg Glu Val Thr Leu Glu Leu Arg Gly Asp
                380                 385                 390
Arg Pro Val Ala Asn Leu Thr Val Ser Val Thr Ala Tyr Thr Ser
                395                 400                 405
Ala Gly Asp Gly Pro Trp Ser Leu Pro Val Pro Leu Glu Pro Trp
                410                 415                 420
Arg Pro Gly Gln Gly Gln Pro Leu His His Leu Val Ser Glu Pro
                425                 430                 435
Pro Pro Arg Ala Phe Ser Trp Pro Trp Trp Tyr Val Leu Leu Gly
                440                 445                 450
Ala Leu Val Ala Ala Ala Cys Val Leu Ile Leu Ala Leu Phe Leu
                455                 460                 465
Val His Arg Arg Lys Lys Glu Thr Arg Tyr Gly Glu Val Phe Glu
                470                 475                 480
Pro Thr Val Glu Arg Gly Glu Leu Val Val Arg Tyr Arg Val Arg
                485                 490                 495
Lys Ser Tyr Ser Arg Arg Thr Thr Glu Ala Thr Leu Asn Ser Leu
                500                 505                 510
Gly Ile Ser Glu Glu Leu Lys Glu Lys Leu Arg Asp Val Met Val
                515                 520                 525
Asp Arg His Lys Val Ala Leu Gly Lys Thr Leu Gly Glu Gly Glu
                530                 535                 540
Phe Gly Ala Val Met Glu Gly Gln Leu Asn Gln Asp Asp Ser Ile
                545                 550                 555
Leu Lys Val Ala Val Lys Thr Met Lys Ile Ala Ile Cys Thr Arg
                560                 565                 570
Ser Glu Leu Glu Asp Phe Leu Ser Glu Ala Val Cys Met Lys Glu
                575                 580                 585
Phe Asp His Pro Asn Val Met Arg Leu Ile Gly Val Cys Phe Gln
                590                 595                 600
Gly Ser Asp Arg Glu Gly Phe Pro Glu Pro Val Val Ile Leu Pro
                605                 610                 615
Phe Met Lys His Gly Asp Leu His Ser Phe Leu Leu Tyr Ser Arg
                620                 625                 630
Leu Gly Asp Gln Pro Val Phe Leu Pro Thr Gln Met Leu Val Lys
                635                 640                 645
Phe Met Ala Asp Ile Ala Ser Gly Met Glu Tyr Leu Ser Thr Lys
                650                 655                 660
```

```
Arg Phe Ile His Arg Asp Leu Ala Ala Arg Asn Cys Met Leu Asn
                665                 670                 675

Glu Asn Met Ser Val Cys Val Ala Asp Phe Gly Leu Ser Lys Lys
                680                 685                 690

Ile Tyr Asn Gly Asp Tyr Tyr Arg Gln Gly Arg Ile Ala Lys Met
                695                 700                 705

Pro Val Lys Trp Ile Ala Ile Glu Ser Leu Ala Asp Arg Val Tyr
                710                 715                 720

Thr Ser Lys Ser Asp Val Trp Ser Phe Gly Val Thr Met Trp Glu
                725                 730                 735

Ile Ala Thr Arg Gly Gln Thr Pro Tyr Pro Gly Val Glu Asn Ser
                740                 745                 750

Glu Ile Tyr Asp Tyr Leu Arg Gln Gly Asn Arg Leu Lys Gln Pro
                755                 760                 765

Val Asp Phe Leu Asp Gly Leu Tyr Ser Leu Met Ser Arg Cys Trp
                770                 775                 780

Glu Leu Asn Pro Arg Asp Arg Pro Ser Phe Ala Glu Leu Arg Glu
                785                 790                 795

Asp Leu Glu Asn Thr Leu Lys Ala Leu Pro Pro Ala Gln Glu Pro
                800                 805                 810

Asp Glu Ile Leu Tyr Val Asn Met Asp Glu Gly Gly Ser His Leu
                815                 820                 825

Glu Pro Arg Gly Ala Ala Gly Gly Ala Asp Pro Pro Thr Gln Pro
                830                 835                 840

Asp Pro Lys Asp Ser Cys Ser Cys Leu Thr Ala Ala Asp Val His
                845                 850                 855

Ser Ala Gly Arg Tyr Val Leu Cys Pro Ser Thr Ala Pro Gly Pro
                860                 865                 870

Thr Leu Ser Ala Asp Arg Gly Cys Pro Ala Pro Pro Gly Gln Glu
                875                 880                 885

Asp Gly Ala
        888
```

PROTEIN TYROSINE KINASES

CROSS REFERENCES

This application is a divisional of co-pending U.S. application Ser. No. 08/170,558 filed Dec. 20, 1993, which application is a continuation of U.S. application Ser. No. 08/157,563 filed Nov. 23, 1993 (abandoned), which applications are incorporated herein by reference and to which applications priority is claimed under 35 USC §120.

BACKGROUND OF THE INVENTION

1. Field of the Invention

This application relates to novel protein tyrosine kinases, the nucleic acid sequences encoding these proteins, the extracellular domains of the proteins, ligands to the protein tyrosine kinases, antibodies specific for the encoded proteins and methods of use therefor. In particular, this application relates to the novel receptor protein tyrosine kinases designated Rse and HPTK6.

2. Description of Related Art

Intracellular signals which control cell growth and differentiation are often mediated by tyrosine kinase proteins. Tyrosine kinases catalyze protein phosphorylation using tyrosine as a substrate for phosphorylation. Members of the tyrosine kinase family can be recognized by the presence of several conserved amino acid regions in the tyrosine kinase catalytic domain (Hanks et al., *Science*: 241: 42–52 [1988]). The tyrosine kinase domain is crucial for the signal transduction pathways required for mitogenesis, transformation and cell differentiation. Certain tyrosine kinases predominantly stimulate cell growth and differentiation, whereas other tyrosine kinases arrest growth and promote differentiation. Furthermore, depending on the cellular environment in which it is expressed, the same tyrosine kinase may either stimulate, or inhibit, cell proliferation (Schlessinger et al., *Neuron*, 9: 383–391 [1992]).

Tyrosine kinase proteins can be classified as either receptor tyrosine kinases or intracellular tyrosine kinases. Receptor tyrosine kinases (rPTKs) convey extracellular signals to intracellular signaling pathways thereby controlling cell proliferation and differentiation. These rPTKs share a similar architecture, with an intracellular catalytic portion, a transmembrane domain and an extracellular ligand-binding domain. (Schesslinger et al., supra). The extracellular domains (ECDs), which are responsible for ligand binding and transmission of biological signals, have been shown to be composed of a number of distinct structural motifs. The intracellular domain comprises a catalytic protein tyrosine kinase. The binding of ligand to the extracellular portion is believed to promote dimerization of the rPTK resulting in transphosphorylation and activation of the intracellular tyrosine kinase domain. In addition to their catalytic function, the intracellular domains (ICDs) of rPTKs may also serve as binding sites for other components of the signal transduction pathway. In particular, some proteins containing src-homology 2 (SH2) domains have been shown to interact in a phosphorylation-dependent and sequence specific manner to specific tyrosine residues within the ICD (Cantley et al., *Cell*, 64: 281–302 [1991]).

A large number of protein tyrosine kinases have been characterized on the basis of their amino acid and nucleic acid sequences. For a review of these proteins see Hanks et al., supra.

WO 93/15201 discloses isolation of several novel rPTK genes found in human megakaryocytic and lymphocytic cells using degenerate oligonucleotide probes as primers in a polymerase chain reaction (PCR) to amplify tyrosine kinase DNA segments.

The recent publication by Johnson et al., *Proc. Natl. Acad. Sci.*, 90: 5677–5681 (1993) discusses the characterization of a receptor tyrosine kinase called discoidin domain receptor (i.e., DDR) which is abundantly expressed in breast carcinoma cell lines. DDR is considered to have two features not found in other receptor tyrosine kinases. First, a region of the amino acid sequence near the N terminus of DDR contains a "discoidin I-like domain". This determination was based on the sequence identity between this region and the protein, discoidin I (see FIG. 5 of Johnson et al.). Discoidin I-like domains are present as tandem repeats at the C terminus of the light chains of factor V (Kane, W. H. & Davie, E. W., *Proc. Natl. Acad. Sci.*, 83: 6800–6804 [1986]), factor VIII (Toole et al., *Nature(London)*, 312: 342–347 [1984]) and Vehar et al., *Nature(London)*, 312: 337–342 [1984]), and two milk fat globule membrane proteins, MFG.E8 (see Stubbs et al., *Proc. Natl. Acad. Sci.*, 87: 8417–8421 [1991]) and BA46 (see Larocca et al., *Cancer Res.*, 51: 4994–4998 [1991]). Second, the DDR protein has an extensive proline/glycine-rich region between the discoidin I-like domain and the transmembrane domain and another such region between the transmembrane domain and the C-terminal tyrosine kinase domain. These proline/glycine-rich regions are not found in other receptor protein tyrosine kinases. The catalytic domain of DDR shares 45% sequence identity with the trk protein catalytic domain disclosed in Martin-Zanca et al., *Mol. Cell. Biol.*, 9:24–33 (1989). Zerlin et al. disclose isolation of the murine equivalent of the DDR rPTK found by Johnson et al., which they call NEP (*Oncogene*,8: 2731–2939 [1993]).

WO 92/14748 discloses a receptor, designated KDR, which is classified as a type III receptor tyrosine kinase and binds to vascular endothelial cell growth factor. The type III group of rPTKs includes the c-kit proto-oncogene and the receptors for platelet derived growth factor (PDGF) and colony stimulating factor-1 (CSF-1).

Matthews et al., *Proc. Natl. Acad. Sci.*, 88: 9026–9030 (1991) refer to the isolation of rPTK clone from a population of hematopoietic murine cells which, like KDR, exhibits a close sequence identity to c-kit. This receptor is called flk-1. The flk-1 receptor was isolated using an anti-sense oligonucleotide primer and anchored PCR. Chromosomal mapping indicated that the flk-1, kit and pdgfra genes are closely linked. Matthews et al., *Cell*, 65: 1143–1152 (1991) discuss isolation of a rPTK called flk-2, from stem cell-enriched murine hematopoietic tissue. U.S. Pat. No. 5,185,438 also refers to the rPTKs, flk-1 and flk-2, which are said to be expressed in primitive hematopoietic cells but not in mature hematopoietic cells.

Lai et al., *Neuron*, 6: 691–704 (1991) used PCR to identify several cDNAs encoding part of the tyrosine kinase domains of various rat rPTKs. The newly isolated sequences were designated tyro-1 to tyro-13. Because preferential expression of several of the sequences in the developing vertebrate nervous system was evidenced, Lai et al. concluded that protein-tyrosine kinases appear to play a central role in neural development.

Holtrich et al., *Proc. Natl. Acad. Sci.*, 88:10411–10415 (1991) studied the expression of protein-tyrosine kinases in normal human lung and tumor cells by PCR followed by molecular cloning and sequence analysis. Six known PTKs (yes, fgr, lyn, hck, pdgfb-r and csfl-r) were detected as well as two new PTKs. One of the proteins detected appeared to be cytosolic. The other PTK, designated TKF, was found to be related to fibroblast growth factor receptor and was only found.expressed in the lung.

WO 93/14124 discloses the cloning, sequencing and expression of a human rPTK termed tie which is expressed in cultured endothelial cells as well as tumor cell lines. The extracellular domain (ECD) of tie was found to contain stretches of amino acid sequence having features of the immunoglobulin, epidermal growth factor and fibronectin type III repeat protein families.

Partanen et al., *Proc. Natl. Acad. Sci.*, 87: 8913–8917 (1990) analyzed PCR amplified cDNA clones which lead to the identification of 14 different tyrosine kinase-related sequences, designated JTK1-14. Based on the pattern of expression of the clones, it was suggested that the tyrosine kinases encoded by the complete sequences most probably play a role in the differentiation of megakaryoblasts or in the physiology of platelets.

While Partanen et al. discuss isolation of the partial JTK11 cDNA clone, the later publication by Janssen et al., *Oncogene*, 6: 2113–2120 (1991), reports the cDNA cloning of the entire oncogene (designated UFO) encoding a 894 amino acid polypeptide. Janssen et al. identified the UFO tyrosine kinase receptor by DNA transfection analysis of bone marrow cells from a patient suffering from a chronic myeloproliferative disorder. It is noted in this publication that several oncogene products are rPTKs, e.g. colony-stimulating factor-1 and TRK. Around the same time that Janssen et al. isolated the rPTK they call UFO, O'Bryan et al. isolated the same rPTK (which they designate Axl) from human myeloid leukemia cells (O'Bryan et al., *Mol. Cell. Biol.*, 11: 5016–5031 [1991]). Axl is a transforming gene which encodes a rPTK having two fibronectin type III repeats and two immunoglobulin-like repeats in the extracellular domain thereof. These motifs are also found in the extracellular domain of the receptor-like protein tyrosine phosphatase, PTPμ (Brady-Kalnay et al., *J. Cell Biol.*, 122: 961–972 [1993]). The immunoglobulin domain and four fibronectin type-III repeats of PTPμ are similar to the motifs found in cell-cell adhesion molecules. Brady-Kalnay et al. propose that the ligand for the PTPμ may be another PTPμ on an adjacent cell.

Faust et al., *Oncogene*, 7: 1287–1293 (1992) disclose cloning of the mouse homologue of the UFO oncogene identified in the publication by Janssen et al. This murine tyrosine kinase has an overall sequence identity of 87.6% with the human sequence. The extracellular domain of the UFO receptor is characterized by the existence of two immunoglobulin-like (IgL) and two fibronectin type III (FNIII) repeats. As discussed in Faust et al., a combination of IgL and FNIII domains are also found in several neural cell adhesion molecules and receptor tyrosine phosphatases suggesting that these structures are important for intercellular communication.

Wilks et al., *Gene*, 85: 67–74 (1989) used degenerate oligodeoxyribonucleotide (oligo) primers derived from amino acid sequence motifs held in common between all members of the PTK family to prime the amplification of PTK sequences. It was found that the most effective type of primer for identification of PTK sequences is a short, moderately degenerate, oligo primer. Using the techniques disclosed, Wilks and his co-workers isolated a new mammalian PTK sequence as well as other known PTK sequences.

Bräuninger et al., *Gene*, 110(2): 205–211 (1992) disclose isolation of a human gene encoding an intracellular protein belonging to a new subclass of protein tyrosine kinases. The clone, designated csk, was found to be expressed in human lung and macrophages. The csk gene was distinguished from the src family of proto-oncogenes by the lack of certain tyrosine autophosphorylation sites in the amino acid sequence and the lack of a N-terminal myristylation site.

It is evident that a number of rPTKs are involved in cell growth and differentiation, many of which have been characterized to date.

Additional rPTKs are needed in order to further study growth and differentiation of cells, for use as therapeutic agents and for diagnostic use.

Accordingly, it is an object of this invention to identify and purify one or more novel protein tyrosine kinase receptors. It is yet another object to provide derivatives and modified forms of such new polypeptides, including amino acid sequence variants and covalent derivatives thereof.

It is another object to provide nucleic acid encoding such novel rPTKs and to use this nucleic acid to produce rPTKs in recombinant cell culture. The rPTK protein thus produced can be used for investigational, therapeutic or diagnostic use. Nucleic acid sequences which hybridize with the DNA or RNA encoding the proteins described herein can also be used as anti-sense oligonucleotides to inhibit protein tyrosine kinase activity either in vivo or in vitro.

It is a further object to provide amino acid sequences encoding the ECDs of the novel rPTKs, which sequences are useful for in vitro assays or for use as therapeutic agents. The ECDs, or variants thereof, can also be used as immunogens for raising antibodies, including agonist antibodies to the rPTKs. Nucleic acid sequences encoding the novel rPTK ECDs are needed in order to make these polypeptides recombinantly.

Ligands to the novel rPTKs are also desirable for use as therapeutic agents to stimulate the receptor and thereby stimulate cell growth and/or differentiation. Such ligands are useful for determining the function and biological activity of the receptors.

These and other objects will be apparent to the ordinary artisan upon consideration of the specification as a whole.

SUMMARY OF THE INVENTION

These objects are accomplished, in one aspect, by providing isolated Rse or HPTK6 rPTKs that may be antigenically or biologically active.

In another aspect, the invention provides a composition comprising biologically active Rse or HPTK6 and a pharmaceutically acceptable carrier.

According to another object of the invention, the isolated extracellular domains of each of the novel rPTKs are provided which can be used to raise antibodies against each of the novel rPTKs.

In another aspect, the invention provides isolated ligands which bind to the extracellular domain of the rPTKs. Such ligands can act as antagonists or agonists and thereby either stimulate, or inhibit, tyrosine kinase activity of the rPTKs.

The invention also provides isolated nucleic acid sequences encoding the entire rPTK amino acid sequence or the extracellular domain thereof, as well as nucleic acid sequences encoding protein ligands to the novel rPTK proteins.

In still further aspects, the nucleic acid is provided in a replicable vector comprising the nucleic acid encoding the proteins disclosed. The invention also provides host cells transformed with the vector. A method of using the nucleic acid encoding the proteins to effect the production of the novel proteins is also provided which comprises expressing the nucleic acid in a culture of the transformed host cells and recovering the protein from the host cell culture.

In further embodiments, the invention provides a method of enhancing cell growth or differentiation comprising administering to a mammalian patient in need of such treatment an exogenous compound selected from the group consisting of: Rse rPTK; HPTK6 rPTK; agonist ligand to Rse rPTK; and agonist ligand to HPTK6 rPTK, in an amount effective in inducing cell growth or differentiation.

BRIEF DESCRIPTION OF THE DRAWINGS

Figure 1C:
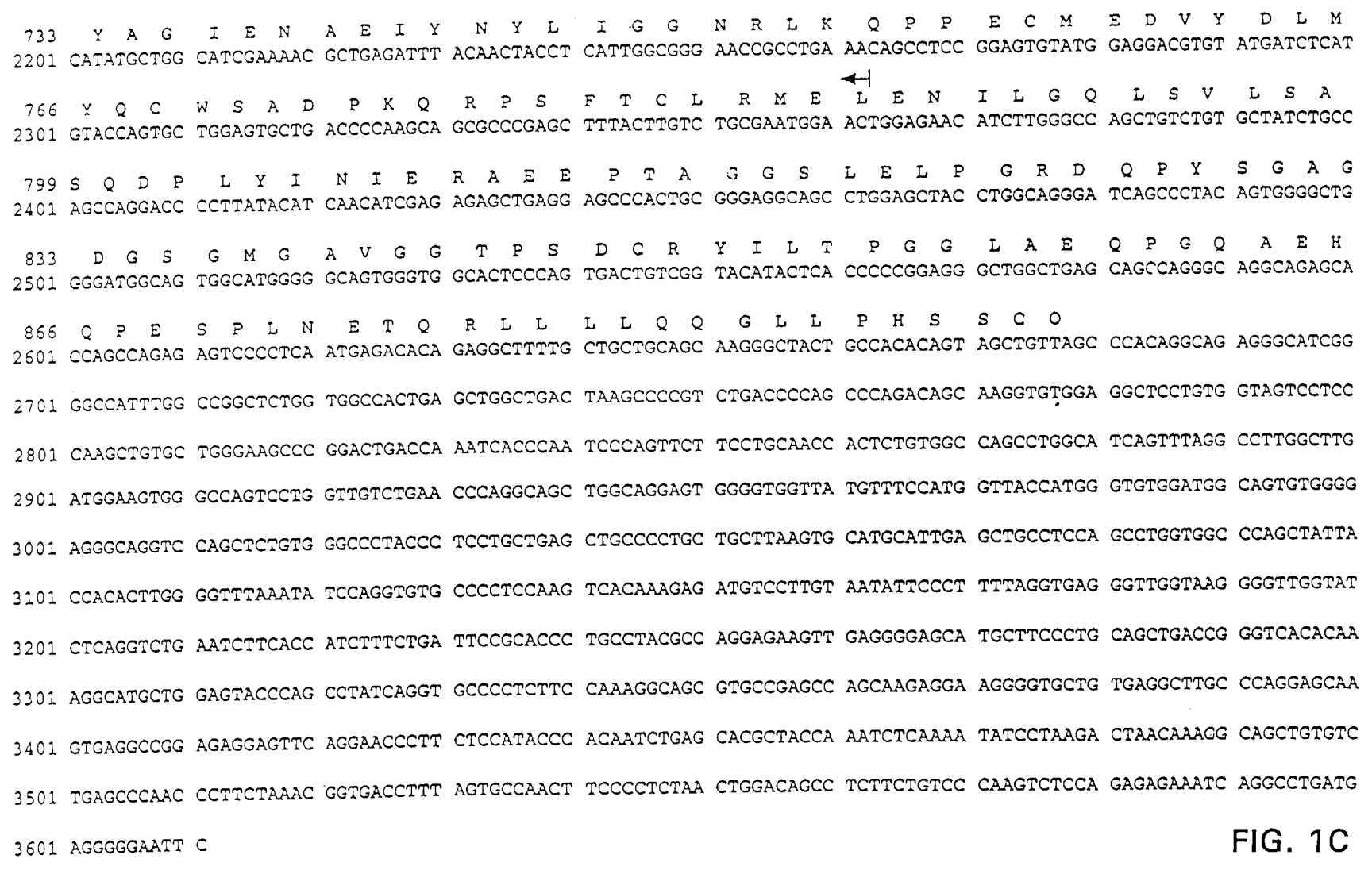
Figure 1D:
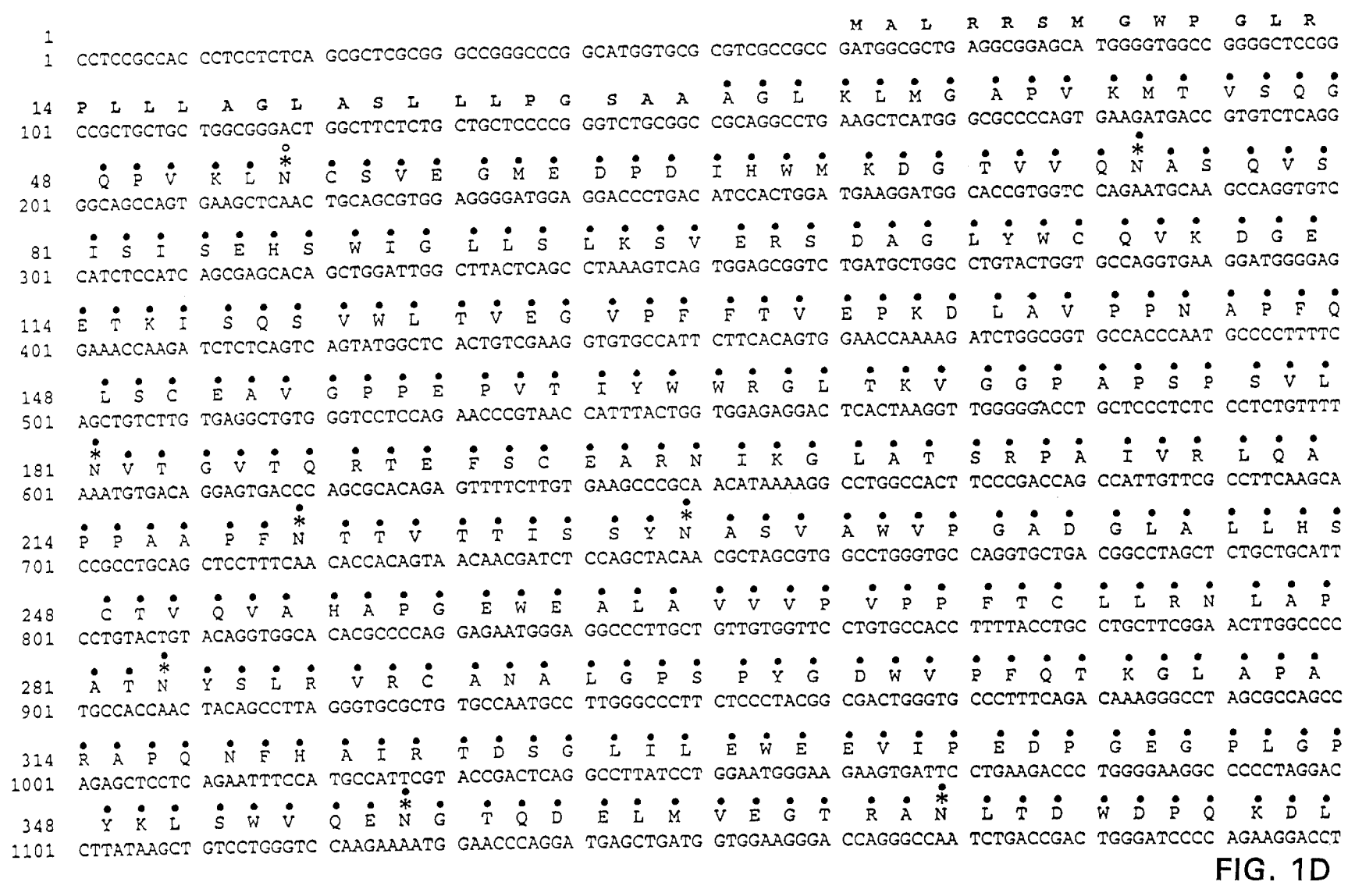
Figure 1E:
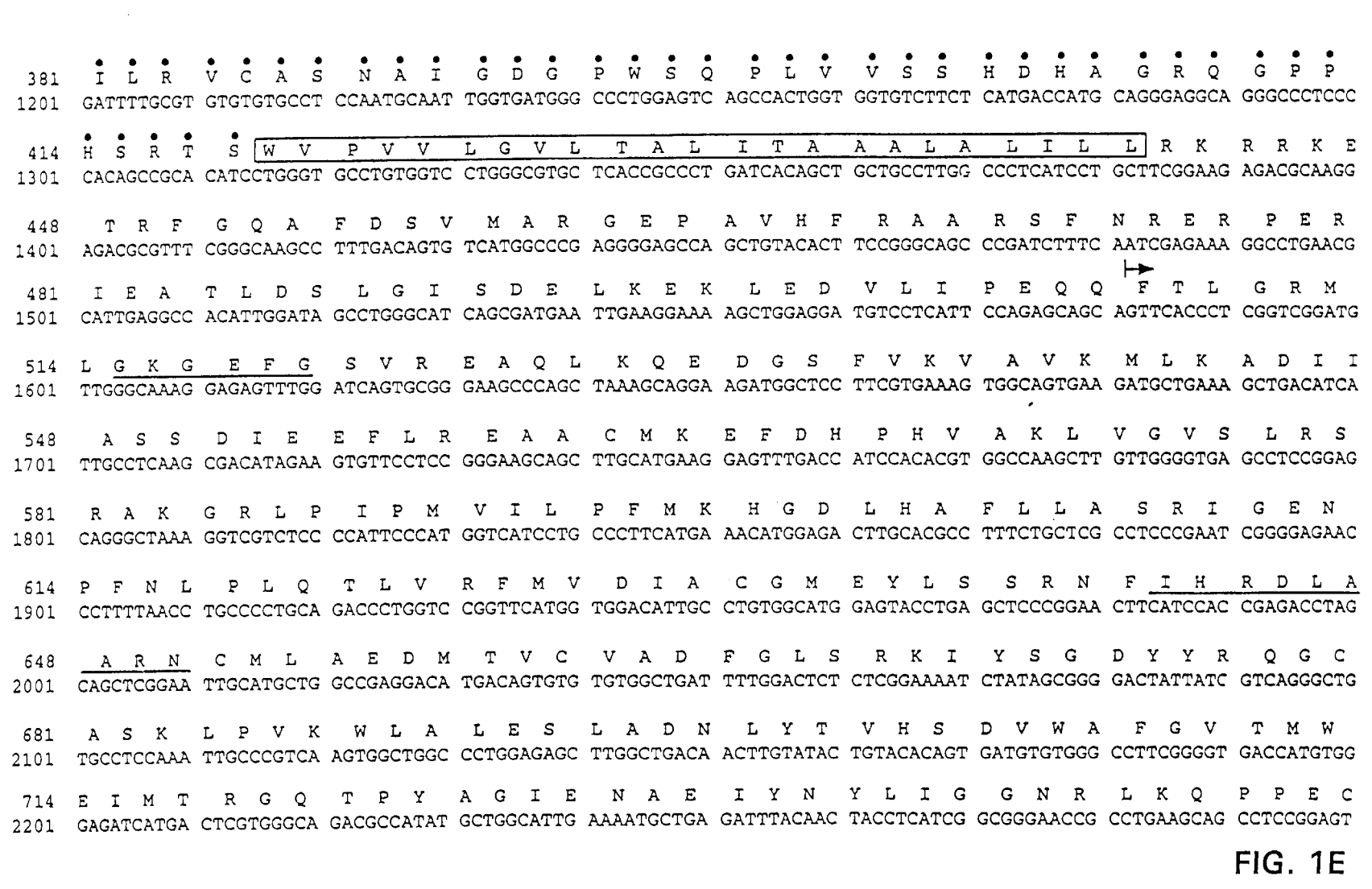

FIG. 1A depicts the nucleic acid sequence for human Rse (SEQ ID NO: 1) and the deduced amino acid sequence thereof (SEQ ID NO: 2). The nucleic acid sequence of the extracellular domain of Rse (SEQ ID NO: 5) and the amino acid sequence of the extracellular domain of Rse (SEQ ID NO: 6) are indicated by dots. FIG. 1B depicts the nucleic acid sequence for murine Rse (SEQ ID NO: 9) and the deduced amino acid sequence thereof (SEQ ID NO: 10). The nucleic acid sequence of the extracellular domain (SEQ ID NO: 11) and the amino acid sequence of the extracellular domain thereof (SEQ ID NO: 12) are indicated by dots.

In FIGS. 1A–1F, the composite nucleic acid sequence determined from overlapping cDNA clones is shown on the bottom line. The translated sequence, in single-letter amino acid code, is shown on the top line. The predicted signal sequences are printed in bold-type, and the potential sites for N-linked glycosylation are indicated with an (*). The putative transmembrane domains are boxed. The arrows delineate the start and end of the putative tyrosine kinase domain, and within that domain, the consensus sites for $Mg^{2+}$-ATP binding (beginning at amino acids 525 and 515 of the human and murine Rse proteins, respectively) and the region often used to predict substrate specificity (beginning at amino acids 652 and 642 of the human and murine Rse proteins, respectively) are underlined. Human and murine Rse sequences represent a total of 3,611 and 3,785 nucleotides, respectively, determined from overlapping clones sequenced in both directions. The human Rse cDNA sequence ends at an internal EcoRI site in the 3' untranslated region; the murine Rse cDNA includes the polyadenylation sequence.

FIGS. 2A–2D depicts the nucleic acid sequence for human HPTK6 (SEQ ID NO: 3) and the deduced amino acid sequence thereof (SEQ ID NO: 4). The nucleic acid sequence of the extracellular domain of HPTK6 (SEQ ID NO: 7) and the amino acid sequence of the extracellular domain of HPTK6 (SEQ ID NO: 8) are in bold, the putative transmembrane domain is boxed, the amino acid residues forming the signal sequence are indicated with an (*) and the putative ATP binding site in the kinase domain is indicated by dots. The arrows delineate the start and end of the putative tyrosine kinase domain.

FIG. 3 is a diagrammatic representation of the structural domains and hydrophobicity plot of human and murine Rse. A schematic representation of the immunoglobulin-like (IgL) domains, fibronectin type III domains (FNIII), transmembrane domain (TM) and tyrosine kinase (Kinase) domains of Rse is shown on the top line. Below, the hydrophobicity profile of human Rse FIG. 3B and murine Rse

FIGS. 4A–4E depicts a comparison of the amino acid sequences of human and murine Rse (i.e., hRSE and mRSE, SEQ ID NOS: 2 and 10, respectively), and Axl (i.e., hAXL and mAXL, SEQ ID NOS: 34 and 35, respectively). Sequences were aligned using the ALIGN program. Gaps introduced for optimal alignment are indicated by dots. The amino acid positions are numbered from the initiation methionine. Conserved residues are boxed. Immunoglobulin-like domains 1 and 2 (IgL-1 and IgL-2), fibronectin type III-like domains 1 and 2 (FN-1 and FN-2), and the tyrosine kinase homology region are indicated. The highly conserved amino acids in the IgL domains are indicated by (*), and the eleven highly conserved domains (Hanks et al., supra) within the tyrosine kinase region are marked.

FIGS. 7A and 7B show a Northern blot analysis of Rse mRNA expression in adult human tissues. In FIG. 7A, a Northern blot containing 2 μg of poly(A) RNA isolated from human tissues was hybridized to a $^{32}$P-labeled probe corresponding to human Rse nucleotides 195–680 (FIG. 1A). Positions of markers are indicated on the right in Kb. Lane 1: heart, lane 2: brain, lane 3: placenta, lane 4: lung, lane 5: liver, lane 6: skeletal muscle, lane 7: kidney, lane 8: pancreas. In FIG. 7B, the blot shown in FIG. 7A was washed and then hybridized with a $^{32}$P-labeled beta-actin probe to confirm the integrity of the RNA samples.

FIGS. 8A and 8B depict the chromosomal localization of the human Rse gene. FIG. 8A depicts the ethidium-stained PCR product of one of two amplifications using independent primer sets (Btk 3-1$^{2724}$, Btk 3-4), corresponding to unique 3'-untranslated sequences in Rse amplifying genomic DNA derived from a panel of human-CHO hybrid cell lines (lanes 1–25), human control (lane 26) or hamster control (lane 27). In FIG. 8B, the matrix of hybrid cell line number and corresponding human chromosome is highlighted to indicate the match of the PCR product with human chromosome 15.

In FIG. 11A, a Northern blot containing 2 μg of poly(A) RNA isolated from murine tissues was hybridized to a $^{32}$P-labeled probe corresponding to human HPTK6 nucleotides 11–622 (FIG. 2). Positions of markers are indicated on the left in Kb. For FIG. 11B, the blot shown in FIG. 11A was washed and then hybridized with a $^{32}$P-labeled beta-actin probe to confirm the integrity of the RNA samples.

For the purposes of convenience alone, in the following Specifications, FIGS. 1A–1C are referred to as "1A", FIGS. 1D–1F are referred to as "FIG. 1B", and FIGS. 2A–2D are referred to as "FIG. 2", FIGS. 3A–3C are referred to as "FIG. 3", and FIGS. 4A–4E are referred to as "FIG. 4".

DETAILED DESCRIPTION OF THE PREFERRED EMBODIMENTS

I. Definitions

Figure 3A:
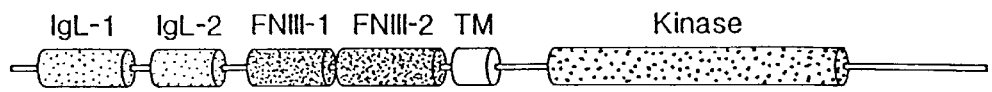

In general, the following words or phrases have the indicated definition when used in the description, examples, and claims:

"Receptor Protein Tyrosine Kinases" (rPTKs), when used throughout the detailed description of the invention, refers to Rse and HPTK6 proteins. It also refers to both full-sequence and ECD unless specifically stated otherwise.

Figure 1A:
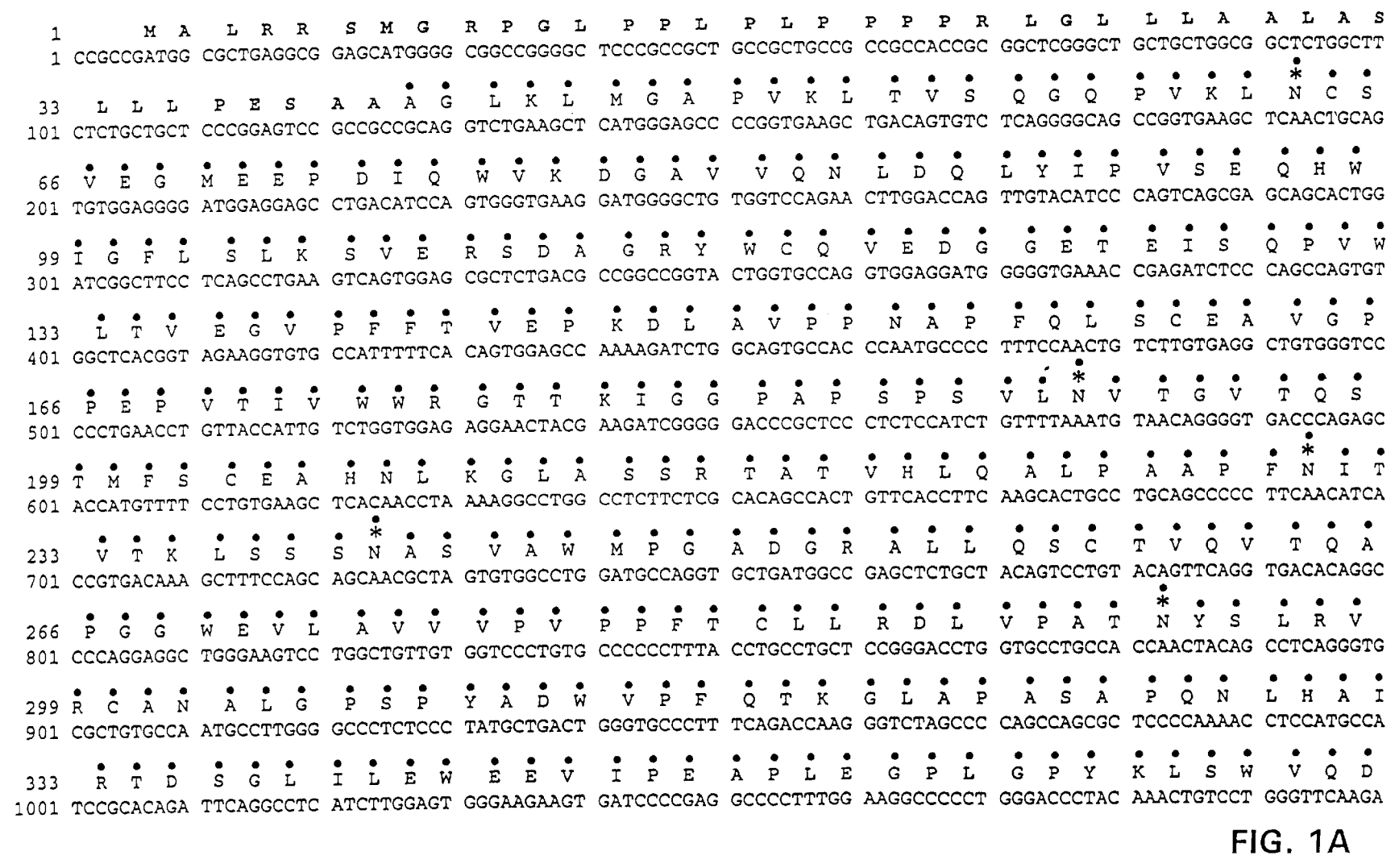
Figure 1B:
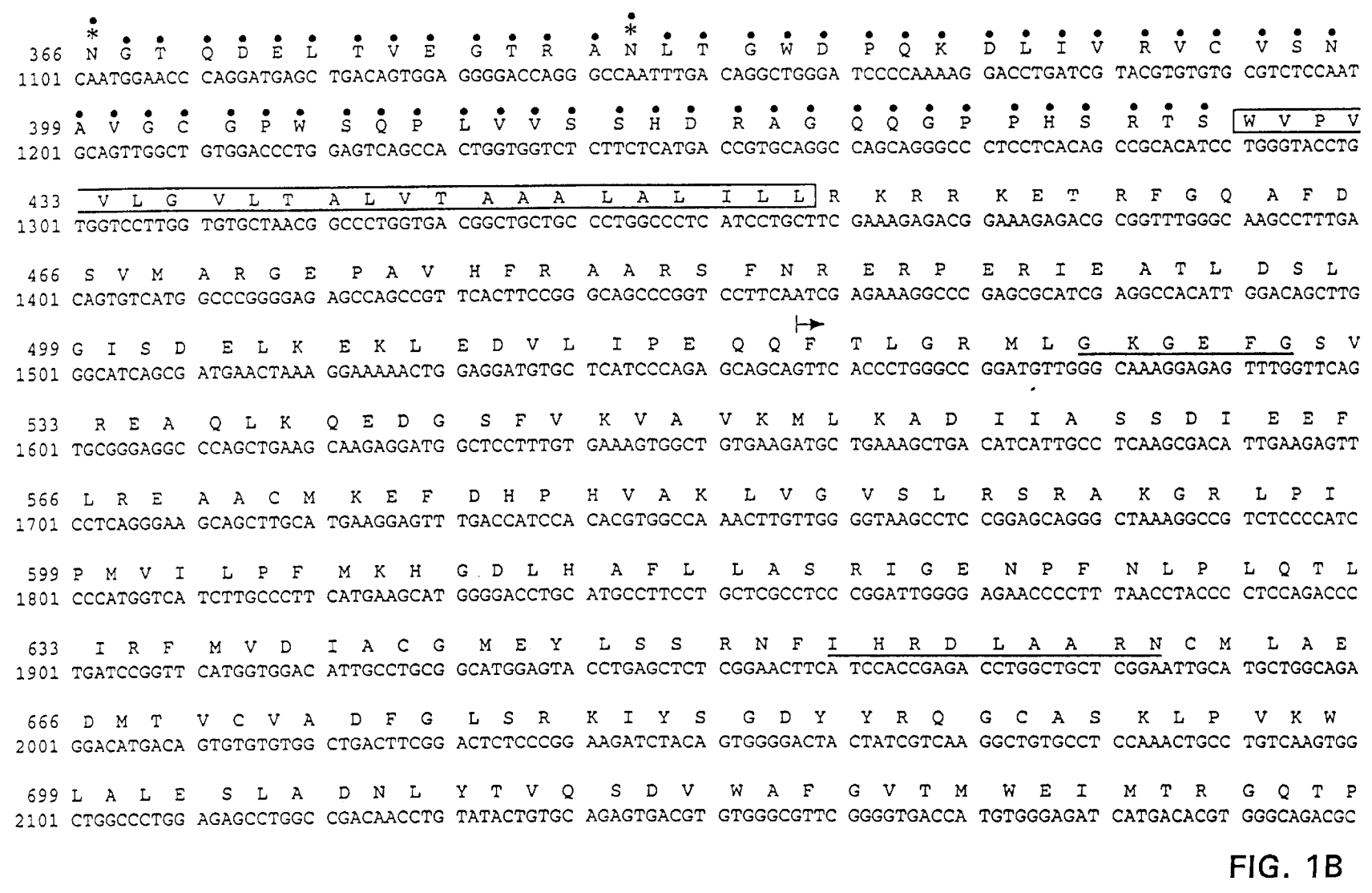

"Rse" is defined herein to be any polypeptide sequence that possesses a biological property of a naturally occurring polypeptide comprising the polypeptide sequence of FIGS. 1A or 1B.

"HPTK6" is defined herein to be any polypeptide sequence that possesses a biological property of a naturally occurring polypeptide comprising the polypeptide sequence of FIG. 2.

"Biological property" for the purposes herein means an in vivo effector or antigenic function or activity that is directly or indirectly performed by Rse or HPTK6 (whether in its native or denatured conformation). Effector functions include receptor function, ligand binding, signal transduction, phosphorylation using tyrosine as a substrate for phosphorylation, dimerization of the rPTK resulting in transphosphorylation and activation of the catalytic kinase domain, any enzyme activity or enzyme modulatory activity (e.g., tyrosine kinase activity), stimulation of cell growth and/or differentiation, inhibition of cell growth or proliferation, or any structural role. However, effector functions do not include possession of an epitope or antigenic site that is capable of cross-reacting with antibodies raised against Rse or HPTK6. An antigenic function means possession of an epitope or antigenic site that is capable of cross-reacting with antibodies raised against the polypeptide sequence of a naturally occurring polypeptide comprising the polypeptide sequence of FIGS. 1A, 1B or FIG. 2.

"Biologically active" rPTK is defined herein as a polypeptide that shares an effector function of rPTK and that may (but need not) in addition possess an antigenic function. A principal known effector function of rPTK is its ability to catalyze protein phosphorylation using tyrosine as a substrate for phosphorylation. The biological activity of rPTK may be further characterized by its ability to stimulate cell growth or differentiation in vivo or in vitro.

"Antigenically active" rPTK is defined as a polypeptide that possesses an antigenic function of rPTK and that may (but need not) in addition possess an effector function.

In preferred embodiments, antigenically active rPTK is a polypeptide that binds with an affinity of at least about $10^6$ l/mole to an antibody capable of binding rPTK. Ordinarily, the polypeptide binds with an affinity of at least about $10^7$ l/mole. Isolated antibody capable of binding rPTK is an antibody that is identified and separated from a component of the natural environment in which it may be present. Most preferably, the antigenically active rPTK is a polypeptide that binds to an antibody capable of binding rPTK in its native conformation. rPTK in its native conformation is rPTK as found in nature that has not been denatured by chaotropic agents, heat, or other treatment that substantially modifies the three-dimensional structure of rPTK as determined, for example, by migration on non-reducing, non-denaturing sizing gels. Antibody used in this determination is rabbit polyclonal antibody raised by formulating native rPTK from a non-rabbit species in Freund's complete adjuvant, subcutaneously injecting the formulation, and boosting the immune response by intraperitoneal injection of the formulation until the titer of anti-rPTK antibody plateaus.

Ordinarily, biologically or antigenically active rPTK will have an amino acid sequence having at least 75% amino acid sequence identity with the mature rPTK amino acid sequence shown in either FIGS. 1A, 1B or FIG. 2, more preferably at least 80%, more preferably at least 85%, more preferably at least 90%, and most preferably at least 95%. Identity or homology with respect to this sequence is defined herein as the percentage of amino acid residues in the candidate sequence that are identical with the rPTK residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the rPTK sequence shall be construed as affecting sequence identity or homology.

Thus, the biologically active and antigenically active rPTK polypeptides that are the subject of this invention include the polypeptide represented by the entire translated nucleotide sequence of rPTK; mature rPTK; fragments thereof having a consecutive sequence of at least 5, 10, 15, 20, 25, 30, or 40 amino acid residues from rPTK; amino acid sequence variants of rPTK wherein an amino acid residue has been inserted N- or C-terminal to, or within, rPTK or its fragment as defined above; amino acid sequence variants of rPTK or its fragment as defined above wherein an amino acid residue of rPTK or its fragment as defined above has been substituted by another residue, including predetermined mutations by, e.g., site-directed or PCR mutagenesis, rPTK of various animal species such as rabbit, rat, porcine, non-human primate, equine, murine, and ovine rPTK and alleles or other naturally occurring variants of the foregoing and human rPTK; derivatives of rPTK or its fragments as defined above wherein rPTK or its fragments have been covalent modified, by substitution, chemical, enzymatic, or other appropriate means, with a moiety other than a naturally occurring amino acid; and glycosylation variants of rPTK (insertion of a glycosylation site or alteration of any glycosylation site by deletion, insertion, or substitution of suitable residues). Such fragments and variants exclude any polypeptide heretofore identified, including any known rPTK of any animal species or any known polypeptide fragment, which is anticipatory under 35 USC §102 as well as polypeptides obvious thereover under 35 USC §103. The preferred rPTK is human mature rPTK.

An "exogenous" therapeutic compound is defined herein to mean a therapeutic compound that is foreign to the mammalian patient, or homologous to a compound found in the mammalian patient but produced outside the mammalian patient.

"Extracellular domain" (ECD) of rPTK is defined herein to be any polypeptide sequence that shares a ligand binding function of the ECD of the naturally occurring Rse polypeptide shown in FIGS. 1A or 1B; or the ECD of the naturally occurring HPTK6 polypeptide shown in FIG. 2 and that may (but need not) in addition possess an antigenic function of the native extracellular domain of Rse or HPTK6. Ligand binding function of the ECD refers to the ability of the polypeptide to bind at least one Rse ligand or at least one HPTK6 ligand. An antigenic function of the ECD means possession of an epitope or antigenic site that is capable of cross-reacting with antibodies raised against the polypeptide sequence of a naturally occurring polypeptide comprising the polypeptide sequence of the ECD of Rse or HPTK6 shown in FIGS. 1A, 1B or FIG. 2. The ECD is essentially free of the transmembrane and intracellular domains of native Rse or. HPTK6, i.e., has less than 1% of such domains, preferably 0.5 to 0% of such domains, and more preferably 0.1 to 0% of such domains.

Ordinarily, the rPTK ECD will have an amino acid sequence having at least 75% amino acid sequence identity with the amino acid sequence of the ECD of Rse indicated in FIGS. 1A or 1B, or the ECD of HPTK6 indicated in FIG. 2, more preferably at least 80%, more preferably at least 85%, more preferably at least 90%, and most preferably at least 95%.

Thus, the ECDs of Rse or HPTK6 that are the subject of this invention include the polypeptide represented by the entire translated nucleotide sequence of the ECD of Rse or HPTK6; amino acid sequence variants of the ECD of Rse or HPTK6 wherein an amino acid residue has been inserted N- or C-terminal to, or within the ECD; amino acid sequence variants of the ECD wherein an amino acid residue of the native ECD of Rse or HPTK6 has been substituted by another residue, including predetermined mutations by, e.g., site-directed or PCR mutagenesis, the ECD of Rse or HPTK6 of various animal species such as rabbit, rat, porcine, non-human primate, equine, murine, and ovine rPTK ECD and alleles or other naturally occurring variants of the foregoing and human ECDs; derivatives of the ECD wherein the ECD has been covalently modified, by substitution, chemical, enzymatic, or other appropriate means, with a moiety other than a naturally occurring amino acid; any glycosylation variants of the ECD. Such variants exclude any polypeptide heretofore identified, which is anticipatory under 35 USC §102 as well as polypeptides obvious thereover under 35 USC §103. The preferred rPTK ECD is the ECD of human Rse or HPTK6.

"Ligand", when used herein, is defined to encompass any molecule, protein or non-protein, which is able to bind to the ECD of Rse or HPTK6. The ligand may be an agonist or an antagonist to Rse or HPTK6. Generally, the ligand will activate one of the effector functions of the rPTK. For example, upon binding the ECD of the rPTK, the ligand may stimulate tyrosine kinase activity. Stimulation of tyrosine kinase activity may, for example, be caused by dimerization of the rPTK which results in transphosphorylation of the kinase domain. Consequently, binding of the ligand to the receptor may result in an enhancement of cell growth and/or differentiation in vivo or in vitro or, conversely, cell growth may be arrested and cell differentiation may be stimulated upon binding of the ligand to the receptor. The ligand may be the endogenous ligand for the receptor and will generally be a polypeptide. In one embodiment disclosed herein, the ligand is an antibody against the ECD of the rPTK. The preferred antibody is a humanized monoclonal antibody against the ECD of rPTK. A "humanized" antibody is a chimeric antibody wherein substantially less than an intact human variable domain has been substituted by the corresponding sequence from a non-human species. Such ligands exclude any molecule heretofore identified, which is anticipatory under 35 USC §102 as well as any molecule obvious thereover under 35 USC §103. The preferred ligand is the endogenous ligand to the ECD of Rse or HPTK6.

"Isolated", when used to describe the various proteins disclosed herein, means protein that has been identified and separated and/or recovered from a component of its natural environment. Contaminant components of its natural environment are materials that would interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the rPTK natural environment will not be present. Ordinarily, however, isolated protein will be prepared by at least one purification step.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

In accordance with this invention, rPTK nucleic acid or a rPTK nucleic acid molecule is RNA or DNA containing greater than ten bases that encodes a biologically active or antigenically active rPTK, is complementary to nucleic acid sequence encoding such rPTK, or hybridizes to nucleic acid sequence encoding such rPTK and remains stably bound to it under stringent conditions. The nucleic acid encoding the rPTKs, comprises nucleic acid residue nos 7-2676 of FIG. 1A (i.e., hRse nucleic acid); nucleic acid residue nos 62-2701 of FIG. 1B (i.e., mRse nucleic acid); or nucleic acid residue nos 82-2820 of FIG. 2 (i.e., HPTK6 nucleic acid). In one embodiment, the nucleic acid sequence is selected from (a) the nucleic acid sequences of FIGS. 1A, 1B or FIG. 2, (b) a sequence corresponding to the sequences of (a) within the scope of degeneracy of the genetic code or (c) a sequence which hybridizes with a sequence defined in (a) or (b) above under stringent conditions.

Preferably, the rPTK nucleic acid molecule encodes a polypeptide sharing at least 75% sequence identity, more preferably at least 80%, still more preferably at least 85%, even more preferably at least 90%, and most preferably 95%, with the rPTK amino acid sequence shown in FIGS. 1A, 1B or FIG. 2. Preferably, the rPTK nucleic acid molecule that hybridizes to nucleic acid sequence encoding rPTK contains at least 20, more preferably 40, and most preferably 90 bases. Such hybridizing or complementary nucleic acid molecule, however, is further defined as being novel under 35 USC §102 and unobvious under 35 USC §103 over any prior art nucleic acid molecules.

Stringent conditions are those that (1) employ low ionic strength and high temperature for washing, for example, 0.015 M NaCl/0.0015 M sodium citrate/0.1 NaDodSO$_4$ at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

An isolated rPTK nucleic acid molecule is a nucleic acid molecule that is identified and separated from at least one contaminant nucleic acid molecule with which it is ordinarily associated in the natural source of the rPTK nucleic acid. An isolated rPTK nucleic acid molecule is other than in the form or setting in which it is found in nature. Isolated rPTK nucleic acid molecules therefore are distinguished from the rPTK nucleic acid molecule as it exists in natural cells. However, an isolated rPTK nucleic acid molecule includes rPTK nucleic acid molecules contained in cells that ordinarily express rPTK where, for example, the nucleic acid molecule is in a chromosomal location different from that of natural cells.

In accordance with this invention, rPTK ECD nucleic acid or a rPTK nucleic acid molecule encoding the ECD of rPTK is RNA or DNA containing greater than ten bases that encodes a polypeptide that shares a ligand binding function of Rse ECD or HPTK6 ECD and that may (but need not) in addition possess an antigenic function, is complementary to nucleic acid sequence encoding such ECD, or hybridizes to nucleic acid sequence encoding such ECD and remains stably bound to it under stringent conditions. In one embodiment, the nucleic acid sequence is selected from (a) the nucleic acid sequences of SEQ ID NO: 5, SEQ ID NO: 7 or SEQ ID NO: 11, (b) a sequence corresponding to the sequences defined in (a) within the scope of degeneracy of the genetic code or (c) a sequence which hybridizes with a sequence defined in (a) or (b) above under stringent conditions.

Preferably, the rPTK ECD nucleic acid molecule encodes a polypeptide sharing at least 75% sequence identity, more preferably at least 80%, still more preferably at least 85%, even more preferably at least 90%, and most preferably 95%, with the amino acid sequences of SEQ ID NO: 5, SEQ ID NO: 7 or SEQ ID NO: 11. Such hybridizing or complementary nucleic acid molecule, however, is further defined as being novel under 35 USC §102 and unobvious under 35 USC §103 over any prior art nucleic acid molecules.

The isolated rPTK polypeptide or rPTK nucleic acid may be labeled for diagnostic and probe purposes, using a label as described and defined further below in the discussion of diagnostic assays.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction enzyme digestion" of DNA refers to catalytic cleavage of the DNA with an enzyme that acts only at certain locations in the DNA. Such enzymes are called restriction endonucleases, and the site for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., *Molecular Cloning: A Laboratory Manual* (New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103–6114 (1981), and Goeddel et al., *Nucleic Acids Res.* 8: 4057 (1980).

"Southern analysis" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" refers to the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 $\mu g$ of DNA. If the DNA is to be ligated into a vector, the vector is first linearized by digestion with the appropriate restriction endonuclease (s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published May. 4, 1988, or via deoxynucleoside H-phosphonate intermediates as described by Froehler et al., *Nucl. Acids Res.*, 14: 5399–5407 (1986). Further methods include the polymerase chain reaction defined below and other autoprimer methods and oligonucleotide syntheses on solid supports. All of these methods are described in Engels et al., *Agnew. Chem. Int. Ed. Engl.*, 28: 716–734 (1989). These methods may be used if the entire nucleic acid sequence of the gene is known, or if the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Ouant. Biol.*, 51: 263 (1987); Erlich, ed., *PCR Technology*, (Stockton Press, NY, 1989). For a recent review on PCR advances, see Erlich et al., *Science*, 252: 1643–1650 (1991).

As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

II. Modes for Practicing the Invention

Section 1 which follows, provides methodologies for preparing full sequence rPTK, rPTK ECD, polypeptide ligands and variants thereof. The techniques disclosed in this section can be utilized for the manufacture of polypeptide ligands to the Rse and HPTK6 receptors.

1. Preparation of Natural Sequence rPTK and Variants thereof

Most of the discussion below pertains to production of rPTK by culturing cells transformed with a vector containing rPTK nucleic acid and recovering the polypeptide from the cell culture. It is further envisioned that the rPTK of this invention may be produced by homologous recombination, as provided for in WO 91/06667 published May 16, 1991. Briefly, this method involves transforming primary mammalian cells containing endogenous rPTK gene (e.g., human cells if the desired rPTK is human) with a construct (i.e., vector) comprising an amplifiable gene [such as dihydrofolate reductase (DHFR) or others discussed below] and at least one flanking region of a length of at least about 150 bp that is homologous with a DNA sequence at the locus of the coding region of the rPTK gene to provide amplification of the rPTK gene. The amplifiable gene must be at a site that does not interfere with expression of the rPTK gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing rPTK are grown so as to express the gene and produce the protein.

A. Isolation of DNA Encoding rPTK

The DNA encoding rPTK may be obtained from any cDNA library prepared from tissue believed to possess the rPTK mRNA and to express it at a detectable level. Accordingly, Rse can be conveniently obtained from a cDNA library prepared from human brain or kidney tissue and HPTK6 can be obtained from a cDNA library is prepared from human adult kidney tissue. The rPTK gene may also be obtained from a genomic library or by oligonucleotide synthesis as defined above assuming the complete nucleotide or amino acid sequence is known.

Libraries are screened with probes designed to identify the gene of interest or the protein encoded by it. For cDNA expression libraries, suitable probes include monoclonal or polyclonal antibodies that recognize and specifically bind to the rPTK; oligonucleotides of about 20–80 bases in length that encode known or suspected portions of the rPTK cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding rPTK is to use PCR methodology as described in section 14 of Sambrook et al., supra. This method requires the use of oligonucleotide probes that will hybridize to the rPTK. Strategies for selection of oligonucleotides are described below.

A preferred method of practicing this invention is to use carefully selected oligonucleotide sequences to screen cDNA libraries from various tissues, preferably mammalian brain and kidney cell lines, more preferably, human brain and human kidney cell lines.

The oligonucleotide sequences selected as probes should be of sufficient length and sufficiently unambiguous that false positives are minimized. The actual nucleotide sequence(s) is usually based on conserved or highly homologous nucleotide sequences or regions of other protein tyrosine kinase molecules. The oligonucleotides may be degenerate at one or more positions. The use of degenerate oligonucleotides may be of particular importance where a library is screened from a species in which preferential codon usage is not known.

The oligonucleotide must be labeled such that it can be detected upon hybridization to DNA in the library being screened. The preferred method of labeling is to use $^{32}P$ labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the rPTK nucleic acid that encodes a full-length polypeptide. In some preferred embodiments, the nucleic acid sequence includes the native rPTK signal sequence. Nucleic acid having all the protein coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of Native rPTK

Amino acid sequence variants of rPTK are prepared by introducing appropriate nucleotide changes into the rPTK DNA, or by synthesis of the desired rPTK polypeptide. Such variants include, for example, deletions from, or insertions or substitutions of, residues within the amino acid sequences shown for the rPTKs in FIGS. 1A, 1B & 2. Any combination of deletion, insertion, and substitution is made to arrive at the final construct, provided that the final construct possesses the desired characteristics. Excluded from the scope of this invention are rPTK variants or polypeptide sequences that are not novel and unobvious over the prior art. The amino acid changes also may alter post-translational processes of the rPTK, such as changing the number or position of glycosylation sites, altering the membrane anchoring characteristics, and/or altering the intracellular location of the rPTK by inserting, deleting, or otherwise affecting the leader sequence of the rPTK.

For the design of amino acid sequence variants of rPTK, the location of the mutation site and the nature of the mutation will depend on the rPTK characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the rPTK polypeptide that are preferred locations for mutagenesis is called "alanine scanning mutagenesis," as described by Cunningham and Wells, *Science*, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed rPTK variants are screened for the optimal combination of desired activity.

There are two principal variables in the construction of amino acid sequence variants: the location of the mutation site and the nature of the mutation. These are variants of the sequences of FIGS. 1A, 1B & 2, and may represent naturally occurring alleles (which will not require manipulation of the rPTK DNA) or predetermined mutant forms made by mutating the DNA, either to arrive at an allele or a variant not found in nature. In general, the location and nature of the mutation chosen will depend upon the rPTK characteristic to be modified. Obviously, such variations that, for example, convert rPTK into a known receptor protein tyrosine kinase are not included within the scope of this invention, nor are any other rPTK variants or polypeptide sequences that are not novel and unobvious over the prior art.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among rPTK and known rPTKs (which share the most sequence identity to the human rPTK amino acid sequence) to modify the activity of rPTK. Deletions from rPTK in areas of substantial homology with homologous rPTK proteins will be more likely to modify the biological activity of rPTK more significantly. The number of consecutive deletions will be selected so as to preserve the tertiary structure of rPTK in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature rPTK sequence) may range generally from about 1 to 10 residues, more preferably 1 to 5, most preferably 1 to 3. Insertions are preferably made in even numbers of residues, but this is not required. Examples of terminal insertions include mature rPTK with an N-terminal methionyl residue, an artifact of the direct expression of mature rPTK in recombinant cell culture, and fusion of a heterologous N-terminal signal sequence to the N-terminus of the mature rPTK molecule to facilitate the secretion of mature rPTK from recombinant hosts. Such signal sequences generally will be obtained from, and thus homologous to, the intended host cell species. Suitable sequences include STII or lpp for *E. coli*, alpha factor for yeast, and viral signals such as herpes gD for mammalian cells.

Other insertional variants of the rPTK molecule include the fusion to-the N- or C-terminus of rPTK of immunogenic polypeptides, e.g., bacterial polypeptides such as beta-lactamase or an enzyme encoded by the *E. coli* tpr locus, or yeast protein, and C-terminal fusions with proteins having a long half-life such as immunoglobulin constant regions (or other immunoglobulin regions), albumin, or ferritin, as described in WO 89/02922 published Apr. 6, 1989.

A third group of variants are amino acid substitution variants. These variants have at least one amino acid residue in the rPTK molecule removed and a different residue inserted in its place. The sites of greatest interest for substitutional mutagenesis include sites identified as the active site(s) of rPTK and sites where the amino acids found in the known analogues are substantially different in terms of side-chain bulk, charge, or hydrophobicity, but where there is also a high degree of sequence identity at the selected site within various animal rPTK species.

Other sites of interest are those in which particular residues of the rPTK obtained from various species are identical. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the rPTK are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Substantial modifications in enzymatic function are accomplished by deletions, or replacement of, tyrosine residues in the catalytic domain of the native rPTK as these modifications may well disrupt the tyrosine kinase activity of the receptor.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of rPTK also may be substituted, generally with serine, to improve the oxidative stability of the molecule and prevent aberrant crosslinking.

Nucleic acid molecules encoding amino acid sequence variants of rPTK are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of rPTK.

Oligonucleotide-mediated mutagenesis is a preferred method for preparing substitution, deletion, and insertion variants of rPTK DNA. This technique is well known in the art as described by Adelman et al., *DNA*, 2: 183 (1983). Briefly, rPTK DNA is altered by hybridizing an oligonucleotide encoding the desired mutation to a DNA template, where the template is the single-stranded form of a plasmid or bacteriophage containing the unaltered or native DNA sequence of rPTK. After hybridization, a DNA polymerase is used to synthesize an entire second complementary strand of the template that will thus incorporate the oligonucleotide primer, and will code for the selected alteration in the rPTK DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, NY 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of rPTK, and the other strand (the original template) encodes the native, unaltered sequence of rPTK. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$P to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (DATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding rPTK mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of rPTK. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 $\mu$l. The reaction mixture is overlaid with 35 $\mu$l mineral oil. The reaction mixture is denatured for five minutes at 100° C., placed briefly on ice, and then 1 $\mu$l *Thermus aquaticus* (Taq) DNA polymerase (5 units/$\mu$l, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.
30 sec. 72° C., then 19 cycles of the following:
  30 sec. 94° C.
  30 sec. 55° C., and
  30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34: 315 (1985). The starting material is the plasmid (or other vector) comprising the rPTK DNA to be mutated. The codon(s) in the rPTK DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the rPTK DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated rPTK DNA sequence.

C. Insertion of Nucleic Acid into Replicable Vector

The nucleic acid (e.g., cDNA or genomic DNA) encoding native or variant rPTK is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The rPTKs of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the rPTK DNA that is inserted into the vector. The heterologous signal sequence selected should be one that is recognized and processed (i.e., cleaved by a signal peptidase) by the host cell. For prokaryotic host cells that do not recognize and process the native rPTK signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, alpha factor leader (including Saccharomyces and Kluyveromyces α-factor leaders, the latter described in U.S. Pat. No. 5,010,182 issued Apr. 23, 1991), or acid phosphatase leader, the C. albicans glucoamylase leader (EP 362,179 published Apr. 4, 1990), or the signal described in WO 90/13646 published Nov. 15, 1990. In mammalian cell expression the native signal sequence (i.e., the rPTK presequence that normally directs secretion of rPTK from human cells in vivo) is satisfactory, although other mammalian signal sequences may be suitable, such as signal sequences from other animal rPTKs, and signal sequences from secreted polypeptides of the same or related species, as well as viral secretory leaders, for example, the herpes simplex gD signal.

The DNA for such precursor region is ligated in reading frame to DNA encoding the mature rPTK.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in E. coli and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of rPTK DNA. However, the recovery of genomic DNA encoding rPTK is more complex than that of an exogenously replicated vector because restriction enzyme digestion is required to excise the rPTK DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., J. Molec. Appl. Genet., 1: 327 [1982]), mycophenolic acid (Mulligan et al., Science, 209: 1422 [1980]) or hygromycin (Sugden et al., Mol. Cell. Biol., 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the rPTK nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes rPTK. Amplification is the process by which genes in greater demand for the production of a protein critical for growth are reiterated in tandem within the chromosomes of successive generations of recombinant cells. Increased quantities of rPTK are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, Proc. Natl. Acad. Sci. USA, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding rPTK. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells [particularly wild-type hosts that contain endogenous DHFR] transformed or co-transformed with DNA sequences encoding rPTK, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 [1979]; Kingsman et al., Gene, 7: 141 [1979]; or Tschemper et al., Gene, 10: 157 [1980]). The trp1 gene provides a selection marker for a mutant strain of yeast lacking the ability to grow in tryptophan, for example, ATCC No. 44076 or PEP4-1 (Jones, Genetics, 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveroznyces yeasts. Bianchi et al., *Curr. Genet.*, 12: 185 (1987). More recently, an expression system for large-scale production of recombinant calf chymosin was reported for K. lactis. Van den Berg, *Bio/Technology*, 8: 135 (1990). Stable multi-copy expression vectors for secretion of mature recombinant human serum albumin by industrial strains of Kluyveromyces have also been disclosed. Fleer et al., *Bio/Technology*, 9: 968–975 (1991).

(iv) Promoter Component

Expression and cloning vectors usually contain a promoter that is recognized by the host organism and is operably linked to the rPTK nucleic acid. Promoters are untranslated sequences located upstream (5') to the start codon of a structural gene (generally within about 100 to 1000 bp) that control the transcription and translation of particular nucleic acid sequence, such as the rPTK nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to rPTK-encoding DNA by removing the promoter from the source DNA by restriction enzyme digestion and inserting the isolated promoter sequence into the vector. Both the native rPTK promoter sequence and many heterologous promoters may be used to direct amplification and/or expression of the rPTK DNA. However, heterologous promoters are preferred, as they generally permit greater transcription and higher yields of rPTK as compared to the native rPTK promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding rPTK (Siebenlist et al., *Cell*, 20: 269 [1980]) using linkers or adaptors to supply any required restriction sites. Promoters for use in bacterial systems also will contain a Shine-Dalgarno (S.D.) sequence operably linked to the DNA encoding rPTK.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

rPTK transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the rPTK sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus; Canaani and Berg, *Proc. Natl. Acad. Sci. USA*, 79: 5166–5170 (1982) on expression of the human interferon β1 gene in cultured mouse and rabbit cells; and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the rPTK of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]), as well as within the coding sequence itself (Osborne et al., *Mol. Cell Bio.*, 4: 1293 [1984]). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the rPTK-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding rPTK.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

(viii) Transient Expression Vectors

Particularly useful in the practice of this invention are expression vectors that provide for the transient expression in mammalian cells of DNA encoding rPTK. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of rPTK that are biologically active rPTK.

(ix) Suitable Exemplary Vertebrate Cell Vectors

Other methods, vectors, and host cells suitable for adaptation to the synthesis of rPTK in recombinant vertebrate cell culture are described in Gething et al., *Nature*, 293: 620–625 (1981); Mantei et al., *Nature*, 281: 40–46 (1979); Levinson et al.; EP 117,060; and EP 117,058. A particularly useful plasmid for mammalian cell culture expression of rPTK is pRK5 (EP pub. no. 307,247) or pSVI6B (PCT pub. no. WO 91/08291 published Jun. 13, 1991).

D. Selection and Transformation of Host Cells

Suitable host cells for cloning or expressing the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonA$\Delta$ ptr3 phoA$\Delta$E15 $\Delta$(argF-lac)169 ompT$\Delta$ degP41kan$^r$. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively, methods of cloning, e.g., PCR or other nucleic acid polymerase reactions, are suitable.

In addition to prokaryotes, eukaryotic microbes such as filamentous fungi or yeast are suitable cloning or expression hosts for rPTK-encoding vectors. *Saccharomyces cerevisiae*, or common baker's yeast, is the most commonly used among lower eukaryotic host microorganisms. However, a number of other genera, species, and strains are commonly available and useful herein, such as Schizosaccharomyces pombe (Beach and Nurse, *Nature*, 290: 140 [1981]; EP 139,383 published May 2, 1985); Kluyveromyces hosts (U.S. Pat. No. 4,943,529; Fleer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia [EP 402,226]; *Pichia pastoris* (EP 183,070; Sreekrishna et al., *J. Basic Microbiol.*, 28: 265–278 [1988]); Candida; *Trichoderma reesia* [EP 244,234]; *Neurospora crassa* (Case et al., *Proc. Natl. Acad. Sci. USA*, 76: 5259–5263 [1979]); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112: 284–289 [1983]; Tilburn et al., *Gene*, 26: 205–221 [1983]; Yelton et al., *Proc. Natl. Acad. Sci. USA*, 81: 1470–1474 [1984]) and *A. niger* (Kelly and Hynes, *EMBO J.*, 4: 475–479 [1985]).

Suitable host cells for the expression of glycosylated rPTK are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the rPTK DNA. During incubation of the plant cell culture with *A. tumefaciens*, the DNA encoding the rPTK is transferred to the plant cell host such that it is transfected, and will, under appropriate conditions, express the rPTK DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology*, 185: 527–537 (1990), and Mansour et al., *Nature*, 336: 348–352 (1988).

E. Culturing the Host Cells

Prokaryotic cells used to produce the rPTK polypeptide of this invention are cultured in suitable media as described generally in Sambrook et al., supra.

The mammalian host cells used to produce the rPTK of this invention may be cultured in a variety of media. Commercially available media such as Ham's P10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. No. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnolog: a Practical Approach*, M. Butler, ed., IRL Press, 1991.

The host cells referred to in this disclosure encompass cells in culture as well as cells that are within a host animal.

F. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native rPTK polypeptide or against a synthetic peptide based on the DNA sequences provided herein as described further in Section 3 below.

G. Purification of rPTK Polypeptide rPTK preferably is recovered from the culture medium as a secreted polypeptide, although it also may be recovered from host cell lysates when directly expressed without a secretory signal.

When rPTK is expressed in a recombinant cell other than one of human origin, the rPTK is completely free of proteins or polypeptides of human origin. However, it is necessary to purify rPTK from recombinant cell proteins or polypeptides to obtain preparations that are substantially homogeneous as to rPTK. As a first step, the culture medium or lysate is centrifuged to remove particulate cell debris. rPTK thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

rPTK variants in which residues have been deleted, inserted, or substituted are recovered in the same fashion as native rPTK, taking account of any substantial changes in properties occasioned by the variation. For example, preparation of a rPTK fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-rPTK column can be employed to absorb the rPTK variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native rPTK may require modification to account for changes in the character of rPTK or its variants upon expression in recombinant cell culture.

H. Covalent Modifications of rPTK Polypeptides

Covalent modifications of rPTK polypeptides are included within the scope of this invention. Both native rPTK and amino acid sequence variants of the rPTK may be covalently modified. One type of covalent modification included within the scope of this invention is a rPTK fragment. Variant rPTK fragments having up to about 40 amino acid residues may be conveniently prepared by chemical synthesis or by enzymatic or chemical cleavage of the full-length or variant rPTK polypeptide. Other types of covalent modifications of the rPTK or fragments thereof are introduced into the molecule by reacting targeted amino acid residues of the rPTK or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking rPTK to a water-insoluble support matrix or surface for use in the method for purifying anti-rPTK antibodies, and vice-versa. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. No. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 [1983]), acetylation of the N-terminal amine, and amidation of any C-terminal carboxyl group.

Another type of covalent modification of the rPTK polypeptide is included within the scope of this invention comprises altering the native glycosylation pattern of the polypeptide. By altering is meant deleting one or more carbohydrate moieties found in native rPTK, and/or adding one or more glycosylation sites that are not present in the native rPTK.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the rPTK polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native rPTK sequence (for O-linked glycosylation sites). For ease, the rPTK amino acid sequence is preferably altered through changes at the DNA level, particularly by mutating the DNA encoding the rPTK polypeptide at preselected bases such that codons are generated that will translate into the desired amino acids. The DNA mutation(s) may be made using methods described above under the heading of "Amino Acid Sequence Variants of rPTK Polypeptide."

Another means of increasing the number of carbohydrate moieties on the rPTK polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crit. Rev. Biochem.*, pp. 259–306 (1981).

Removal of carbohydrate moieties present on the rPTK polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259: 52 (1987) and by Edge et al., *Anal. Biochem.*, 118: 131 (1981). Enzymatic cleavage of carbohydrate moieties on polypeptides can be achieved by the use of a variety of endo- and exo-glycosidases as described by Thotakura et al., *Meth. Enzymol.*, 138: 350 (1987).

Glycosylation at potential glycosylation sites may be prevented by the use of the compound tunicamycin as described by Duskin et al., *J. Biol. Chem.*, 257: 3105 (1982). Tunicamycin blocks the formation of protein-N-glycoside linkages.

Another type of covalent modification of rPTK comprises linking the rPTK polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

rPTK also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

rPTK preparations are also useful in generating antibodies, as standards in assays for rPTK (e.g., by labeling rPTK for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant rPTK, it will be appreciated that some screening of the recovered variant will be needed to select the optimal variant. For example, one can screen for protein kinase activity using the techniques set forth in Lokker et al., *EMBO*, 11, 2503–2510 (1992). A change in the immunological character of the rPTK molecule, such as affinity for a given antibody, is also able to be measured by a competitive-type immunoassay. The variant is assayed for changes in the suppression or enhancement of its enzymatic activity by comparison to the activity observed for native rPTK in the same assay. Other potential modifications of protein or polypeptide properties such as redox or thermal stability, hydrophobicity, susceptibility to proteolytic degradation, or the tendency to aggregate with carriers or into multimers are assayed by methods well known in the art.

2. Uses, Therapeutic Compositions and Administration of rPTK rPTK is believed to find therapeutic use for treating mammals via stimulation of cell growth and/or differentiation. For example, Rse or HPTK6 may be used to treat neuro-degenerative diseases (e.g. senile dementia of the Alzheimer's type, peripheral neuropathies, Parkinson's disease and Huntington's disease) or diseases of the kidney (e.g., glomerulus sclerosis, which is associated with diabetes). Rse may similarly be used to generate the production of platelets from megakaryocytes. Hence, the Rse may find utility for use in relation to bone marrow transplants, for example.

The nucleic acid encoding the rPTK may be used as a diagnostic for tissue-specific typing. For example, such procedures as in situ hybridization, Northern and Southern blotting, and PCR analysis may be used to determine whether DNA and/or RNA encoding rPTK is present in the cell type(s) being evaluated.

Isolated rPTK polypeptide may also be used in quantitative diagnostic assays as a standard or control against which samples containing unknown quantities of rPTK may be prepared.

Therapeutic formulations of rPTK for treating neuro-degenerative or kidney diseases are prepared for storage by mixing rPTK having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as is Tween, Pluronics or polyethylene glycol (PEG). rPTK to be used for in vivo administration must be sterile.

This is readily accomplished by filtration through sterile filtration membranes, prior to or following lyophilization and reconstitution. rPTK ordinarily will be stored in lyophilized form or in solution.

Therapeutic rPTK compositions generally are placed into a container having a sterile access port, for example, an intravenous solution bag or vial having a stopper pierceable by a hypodermic injection needle.

The route of rPTK, or rPTK antibody administration is in accord with known methods, e.g., injection or infusion by intravenous, intraperitoneal, intracerebral, intramuscular, intraocular, intraarterial, or intralesional routes, or by sustained release systems as noted below. rPTK is administered continuously by infusion or by bolus injection. rPTK antibody is administered in the same fashion, or by administration into the blood stream or lymph.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethylmethacrylate) as described by Langer et al., *J. Biomed. Mater. Res.*, 15: 167–277 (1981) and Langer, Chem. Tech., 12: 98–105 (1982) or poly (vinylalcohol)], polylactides (U.S. Pat. No. 3,773,919, EP 58,481), copolymers of L-glutamic acid and gamma ethyl-L-glutamate (Sidman et al., *Biopolymers*, 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release rPTK compositions also include liposomally entrapped rPTK. Liposomes containing rPTK are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83–118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal rPTK therapy.

An effective amount of rPTK to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer rPTK until a dosage is reached that achieves the desired effect. The progress of this therapy is easily monitored by conventional assays.

3. rPTK Antibody Preparation

The antibodies of this invention are obtained by routine screening. Polyclonal antibodies to the rPTK generally are raised in animals by multiple subcutaneous (sc) or intraperitoneal (ip) injections of the rPTK and an adjuvant. It may be useful to conjugate the rPTK or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=$C$=$NR$, where R and $R^1$ are different alkyl groups.

The route and schedule of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 $\mu$g of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. 7 to 14 days later animals are bled and the serum is assayed for anti-rPTK titer. Animals are boosted until the titer plateaus. Preferably, the animal is boosted with the conjugate of the same rPTK, but conjugated to a different protein and/or through a different cross-linking agent. Conjugates also can be made in recombinant cell culture as protein fusions. Also, aggregating agents such as alum are used to enhance the immune response.

After immunization, monoclonal antibodies are prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.*, 6: 511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the rPTK in test samples.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 [1985]). In fact, according to the invention, techniques developed for the production of chimeric antibodies (Morrison et al., *Proc. Natl. Acad. Sci.*, 81: 6851 [1984]); Neuberger et al., *Nature*, 312: 604 [1984]; Takeda et al., *Nature*, 314: 452 [1985]; EP 184,187; EP 171,496; EP 173,494; PCT WO 86/01533; Shaw et al., *J. Nat. Canc. Inst.*, 80: 1553–1559 [1988]; Morrison, *Science*, 229: 1202–1207 [1985]; and Oi et al., *BioTechniques*, 4: 214 [1986]) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

In a preferred embodiment of the invention, humanized antibodies are used to reduce or eliminate any anti-globulin immune response in humans. As used herein, the term "humanized" antibody is an embodiment of chimeric antibodies wherein substantially less than an intact human variable domain has been substituted by the corresponding sequence from a non-human species. In practice, humanized antibodies are typically human antibodies in which some amino acid residues from the complementarity determining regions (CDRs), the hypervariable regions in the variable domains which are directly involved with formation of the antigen-binding site, and possibly some amino acids from the framework regions (FRs), the regions of sequence that are somewhat conserved within the variable domains, are substituted by residues from analogous sites in rodent antibodies. The construction of humanized antibodies is described in Riechmann et al., *Nature*, 332: 323–327 (1988), Queen et al., *Proc. Natl. Acad. Sci. USA*, 86: 10029–10033 (1989), Co et al., *Proc. Natl. Acad. Sci. USA*, 88: 2869–2873 (1991), Gorman et al., *Proc. Natl. Acad. Sci.*, 88: 4181–4185 (1991), Daugherty et al., *Nucleic Acids Res.*, 19: 2471–2476 (1991), Brown et al., *Proc. Natl. Acad. Sci. USA*, 88: 2663–2667 (1991), Junghans et al., *Cancer Res.*, 50: 1495–1502 (1990), Fendly et al., *Cancer Res.*, 50: 1550–1558 (1990) and in PCT application WO 89/06692.

In some cases, substituting CDRs from rodent antibodies for the human CDRs in human frameworks is sufficient to transfer high antigen binding affinity (Jones et al., *Nature*, 321: 522–525 [1986]; Verhoeyen et al., *Science*, 239: 1534–1536 [1988]) whereas in other cases it is necessary to additionally replace one (Riechmann et al., supra) or several (Queen et al., supra) FR residues. See also Co et al., supra.

In a particularly preferred embodiment of the invention, the humanized antibodies are designed and constructed according to the methods described in PCT application WO 92/22653, the entire disclosure of which is specifically incorporated herein by reference.

Techniques for creating recombinant DNA versions of the antigen-binding regions of antibody molecules (known as Fab fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed Fab protein to migrate to the periplasmic space (between the bacterial cell membrane and the cell wall) or to be secreted. One can rapidly generate and screen great numbers of functional Fab fragments for those that bind the antigen. Such rPTK-binding molecules (Fab fragments with specificity for the rPTK) are specifically encompassed within the term "antibody" as it is defined, discussed, and claimed herein.

The antibody preferably does not cross-react with other known receptor protein tyrosine kinases.

4. Uses of rPTK Antibodies rPTK antibodies may be used as ligands to the rPTK and are also useful in diagnostic assays for rPTK, e.g., detecting its expression in specific cells, tissues, or serum. The antibodies are labeled in the same fashion as rPTK described above and/or are immobilized on an insoluble matrix. In one embodiment of a receptor binding assay, an antibody composition that binds to all or a selected plurality of members of the rPTK family is immobilized on an insoluble matrix, the test sample is contacted with the immobilized antibody composition to adsorb all rPTK family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

The antibodies of this invention are also useful in passively immunizing patients.

rPTK antibodies also are useful for the affinity purification of rPTK or rPTK ECD from recombinant cell culture or natural sources. rPTK antibodies that do not detectably cross-react with other receptor protein tyrosine kinases can be used to purify rPTK or rPTK ECD free from these other known proteins.

Suitable diagnostic assays for rPTK and its antibodies are well known per se. For example, competitive, sandwich and steric inhibition immunoassay techniques are useful. The competitive and sandwich methods employ a phase-separation step as an integral part of the method while steric inhibition assays are conducted in a single reaction mixture. Fundamentally, the same procedures are used for the assay of rPTK and for substances that bind rPTK, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for rPTK or its antibodies all use one or more of the following reagents: labeled analyte analogue, immobilized analyte analogue, labeled binding partner, immobilized binding partner, and steric conjugates. The labeled reagents also are known as "tracers."

The label used (and this is also useful to label rPTK nucleic acid for use as a probe) is any detectable functionality that does not interfere with the binding of analyte and its binding partner. Numerous labels are known for use in immunoassay, examples including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Those of ordinary skill in the art will know of other suitable labels that may be employed in accordance with the present invention. The binding of these labels to rPTK, antibodies, or fragments thereof can be accomplished using standard techniques commonly known to those of ordinary skill in the art. For instance, coupling agents such as dialdehydes, carbodiimides, dimaleimides, bis-imidates, bis-diazotized benzidine, and the like may be used to tag the polypeptide with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); Nygren, *J. Histochem. and Cytochem.*, 30: 407–412 (1982); O'Sullivan et al., *Methods in Enzymology*, ed. J. J. Langone and H. Van Vunakis, Vol. 73 (Academic Press, New York, N.Y., 1981), pp. 147–166; Kennedy et al., *Clin. Chim. Acta*, 70: 1–31 (1976); and Schurs et al., *Clin. Chim. Acta*, 81: 1–40 (1977). Coupling techniques mentioned in the lattermost reference are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the assays of the present invention are alkaline phosphatase, HRP, beta-galactosidase, urease, glucose oxidase, glucoamylase, malate dehydrogenase, and glucose-6-phosphate dehydrogenase. Urease is among the more preferred enzyme labels, particularly because of chromogenic pH indicators that make its activity readily visible to the naked eye.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, rPTK or its immunologically active fragments are conjugated with a bifunctional organic bridge to an enzyme such as peroxidase. Conjugates are selected for use with anti-rPTK so that binding of the anti-rPTK inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of rPTK or rPTK antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-rPTK monoclonal antibody as one antibody and a polyclonal anti-rPTK antibody as the other is useful in testing samples for rPTK activity.

The foregoing are merely exemplary diagnostic assays for rPTK and antibodies. Other methods now or hereafter developed for the determination of these analytes are included within the scope hereof, including the bioassays described above.

5. rPTK Ligand Preparation

As discussed above, rPTK ligands can comprise antibodies (including polyclonal antibodies, monoclonal antibodies and humanized monoclonal antibodies) against the rPTK. Other protein and non-protein ligands are also contemplated within the scope of the invention.

The ligand preferably constitutes the endogenous ligand to the rPTK. In order to isolate the endogenous rPTK ligand, primary cells purified from natural sources (e.g., blood tissue extracts or urine) or cell lines expressing the ligands are screened for the ligand. Cells used to isolate the ligands may, for example, be selected from human kidney and brain cells. Cell lines can be established using well known techniques such as immortalization of the cells via transformation with viral DNA (e.g., SV40 DNA).

The endogenous ligand can then be identified and isolated using techniques which have been established in the art. For example, the techniques disclosed in WO/92/20798 can be used to isolate the ligand to the rPTK. Generally, the ligand will be recovered from a cellular membrane fraction or a secreted form of the ligand will be isolated from the culture medium. Accordingly, the culture medium or lysate is centrifuged to remove particulate cell debris. The ligand is then purified from the soluble protein fraction or the membrane fraction of the culture lysate by biochemical separation. The following procedures are exemplary of suitable purification procedures: fractionation on an immunoaffinity or ion-exchange column; ethanol precipitation; reversed phase HPLC; chromatography on silica, Heparin Sepharose or on a cation exchange resin such as DEAE; chromatofocusing; SDS-PAGE; ammonium sulfate precipitation; and gel filtration using, for example, Sephadex G-75. Each of the fractions can then be assayed for its ability to phosphorylate the rPTK (see Example 1 for a suitable assay for tyrosine kinase activity), in order to isolate the fraction containing the ligand to the rPTK. Further purification of the fraction can then be carried out as required.

Alternatively, the techniques used by Flanagan et al., *Cell*, 63: 185–194 (1990) can be carried out. Flanagan et al. isolated the ligand to the c-kit proto-oncogene by genetically fusing the c-kit ECD to placental alkaline phosphatase thereby forming a soluble receptor affinity reagent with an enzyme tag that could be readily traced. Binding of the fusion proteins is detectable by the enzymatic activity of the alkaline phosphatase secreted into the medium. The fusion protein so formed, termed APtag-KIT, binds with high affinity to cell lines expressing the ligand of interest. The bound cells are then isolated from the APtag-KIT complex. Accordingly, a chimeric nucleic acid construct encoding the ECD of Rse or the ECD of HPTK6 fused to the secretable alkaline phosphatase marker can be generated.

To clone the cDNA that encodes the ligand, a cDNA library is constructed from the isolated cells in a suitable expression vector, such as the vectors discussed earlier herein. The library is then transfected into host cells (see above) and cells having the ligand on their surface are detected using the techniques of Flanagan et al. Single cell suspensions are incubated with the APtag-KIT and, after removing APtag-KIT proteins which are not bound to the cells by centrifugation, cells are panned on plates coated with antibodies against alkaline phosphatase (Seed et al., *Proc. Natl. Acad. Sci.*, 84:, 3365–69 [1987]). Cells to which the antibodies are bound are isolated and the DNA is extracted therefrom using techniques available to the skilled artisan.

6. Uses, Therapeutic Compositions and Administration of rPTK Ligand rPTK ligands are believed to find therapeutic use for treating mammals via stimulation of cell growth and/or differentiation. For example, Rse ligand may be used to treat neuro-degenerative diseases (e.g. senile dementia of the Alzheimer's type, peripheral neuropathies, Parkinson's disease and Huntington's disease) or diseases of the kidney (e.g., glomerulus sclerosis, which is associated with diabetes). Rse ligand may also be used to generate the production of platelets from megakaryocytes. Like Rse ligand, HPTK6 ligand may be used to treat kidney diseases, such as glomerulus sclerosis. An antagonist ligand for HPTK6 may find therapeutic use in the treatment of cancer, e.g. breast cancer.

Therapeutic formulations of rPTK ligand are prepared for storage by mixing the ligand having the desired degree of purity with optional physiologically acceptable carriers, excipients, or stabilizers (*Remington's Pharmaceutical Sciences*, supra), in the form of lyophilized cake or aqueous solutions. rPTK ligand to be used for in vivo administration must be sterile. This is readily accomplished by filtration through sterile filtration membranes, prior to or following lyophilization and reconstitution. rPTK ligand ordinarily will be stored in lyophilized form or in solution.

Therapeutic rPTK ligand compositions generally are placed into a container having a sterile access port, for example, an intravenous solution bag or vial having a stopper pierceable by a hypodermic injection needle.

The route of rPTK ligand administration is in accord with known methods, e.g., injection or infusion by intravenous, intraperitoneal, intracerebral, intramuscular, intraocular, intraarterial, or intralesional routes, or by sustained release systems as noted below. rPTK ligand is administered continuously by infusion or by bolus injection.

An effective amount of rPTK ligand to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer rPTK ligand until a dosage is reached that achieves the desired effect. The progress of this therapy is easily monitored by conventional assays.

7. Uses, Therapeutic Compositions and Administration of rPTK ECD

As discussed above, rPTK ECD can be used for the identification and isolation of ligands to the rPTKs using the techniques disclosed in Flanagan et al., supra, for example.

rPTK ECD is also believed to find use as a therapeutic compound for removal of excess systemic or tissue-localized rPTK ligand which has been administered to a patient. Removal of excess ligand is particularly desirably where the ligand may be toxic to the patient. The rPTK ECD acts to bind the ligand in competition with endogenous rPTKs in the patient. Similarly, it is contemplated that the rPTK ECD can be administered to a patient simultaneously, or subsequent to, administration of the ligand in the form of a sustained release composition. The ECD acts as a soluble binding protein for the ligand, thereby extending the half-life of the ligand. Also, the ECD may constitute a ligand to the receptor in so far as it is able to bind to, and activate, the ECD of an adjacent membrane bound rPTK. Accordingly, the ECD may be used as a ligand to the rPTK.

The nucleic acid encoding the rPTK ECD may be used as a diagnostic for tissue-specific typing. For example, such procedures as in situ hybridization, Northern and Southern blotting, and PCR analysis may be used to determine whether DNA and/or RNA encoding rPTK is present in the cell type(s) being evaluated.

Therapeutic formulations of rPTK ECD are prepared for storage by mixing rPTK ECD having the desired degree of purity with optional physiologically acceptable carriers, excipients, or stabilizers (*Remington's Pharmaceutical Sciences*, supra), in the form of lyophilized cake or aqueous solutions.

rPTK ECD to be used for in vivo administration must be sterile. This is readily accomplished by filtration through sterile filtration membranes, prior to or following lyophilization and reconstitution. rPTK ECD ordinarily will be stored in lyophilized form or in solution.

Therapeutic rPTK ECD compositions generally are placed into a container having a sterile access port, for example, an intravenous solution bag or vial having a stopper pierceable by a hypodermic injection needle.

The route of rPTK ECD administration is in accord with known methods, e.g., injection or infusion by intravenous, intraperitoneal, intracerebral, intramuscular, intraocular, intraarterial, or intralesional routes, or by sustained release systems as noted below. rPTK ECD is administered continuously by infusion or by bolus injection.

An effective amount of rPTK ECD to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer rPTK ECD until a dosage is reached that achieves the desired effect. The progress of this therapy is easily monitored by conventional assays.

The following examples are offered by way of illustration and not by way of limitation. The disclosures of all literature references cited in the specification are expressly incorporated herein by reference.

EXAMPLE 1

Isolation and Characterization of Rse

A. cDNA Cloning and Sequencing

Degenerate oligodeoxyribonucleotide primers were designed to sequences encoding conserved amino acids in tyrosine kinases (Lai et al., supra). These primers were used to amplify fragments of tyrosine kinase containing genes from cDNA prepared from human brain RNA. Amplified fragments were cloned and sequenced. Nested oligodeoxyribonucleotide primers (pair A: 5'-CGGATCCAC(AC)G (ATGC)GA(CT)(CT)T (SEQ ID NO: 13) and 5'-GGAATTCC(TC)TC(AT)GGAG(CT)(AG)TCCA(TC) (TC)T (SEQ ID NO: 14); pair B: 5'-CGGATCCATCCACAGAGATGT (SEQ ID NO: 15) and 5'-GGAATTCCAAAGGACCA(GC)AC(GA)TC) (SEQ ID NO: 16) were used to amplify fragments of cDNA prepared from human brain RNA. Amplified DNA fragments were cloned as BamHI and EcoRI inserts in pUCl9 (see Hanks et al., supra). Amplification reactions were performed using Taq DNA polymerase in a Perkin-Elmer 480 thermocycler, 40 cycles of 94° C. for 30 seconds, 45° C. for 30 seconds, and 72° C. for 1 minute; L5 primer-pair B was added following cycle 20. Recombinants were identified and sequenced using the dideoxynucleotide method. A 50 base single-stranded oligodeoxyribonucleotide probe (5'-GACCGTGTGTGTGGCTGACTTTG-GACTCTCCTGGAAGATC (SEQ ID NO: 17)) was used as a probe to screen $1.2\times10^6$ plaques from a random-primed lambda gt10 library prepared from RNA isolated from human fetal brain. Conditions for plating libraries, hybridizing and washing filters were as previously described (Godowski, et al., *Proc. Natl. Acad. Sci.* 86: 8083–8087 [19891]). One positive plaque was obtained, with an insert size of approximately 1.2 Kb. An oligodeoxyribonucleotide probe (5'-GGCTGTGCCTCCAAATTGCCCGT-CAAGTGGCTGGCCCTGG (SEQ ID NO: 18)) based on sequence obtained from the 5' end of the 1.2 Kb clone was used to screen $1.2 \times 10^6$ plaques from an oligo dT-primed lambda gt10 library prepared from RNA from the Hep 3B cell line. The inserts from 15 positive plaques were characterized, and the largest insert, approximately 3.5 Kb in length, was sequenced. An oligodeoxyribonucleotide primer (5'-AGCCGGTGAAGCTGAACTGCAGTGTG-GAGGGGATGGAGGAGCCTGACATC (SEQ ID NO: 19)) based on sequence from the 5' region of the 3.5 Kb clone was used to screen $1.2 \times 10^6$ plaques from a second lambda gt10 Hep 3B library. Four clones were obtained, and one of these contained a 3.0 Kb insert that contained the putative initiator methionine.

The murine homologue of Rse was obtained by screening a murine brain cDNA library prepared in lambda gt10 (Clontech, Palo Alto Calif.) with a random-primed probe corresponding to nucleotides 1–1163 from the human Rse cDNA (FIG. 1A). Thirteen clones were purified and the size of the inserts was determined. Two overlapping clones, mbptk3.1 and mbptk3.8 (corresponding to nucleotides 737–3759 and 367–3785 of the murine Rse cDNA, respectively, of FIG. 1B) were sequenced. To obtain the 5' region of the murine Rse cDNA, an oligonucleotide probe derived from the 5' end of the mbptk3.8 clone (5'-TCCAGCTACAACGCTAGCGTGGC-CTGGGTGCCAGGTGCTGACGGCCTAGC (SEQ ID NO: 20)) was used to rescreen the murine brain cDNA library. Two positive plaques were purified, and the 5' end of the mbptk3.14 insert was sequenced and shown to contain the 5' end of the murine Rse cDNA.

Figure 4A:
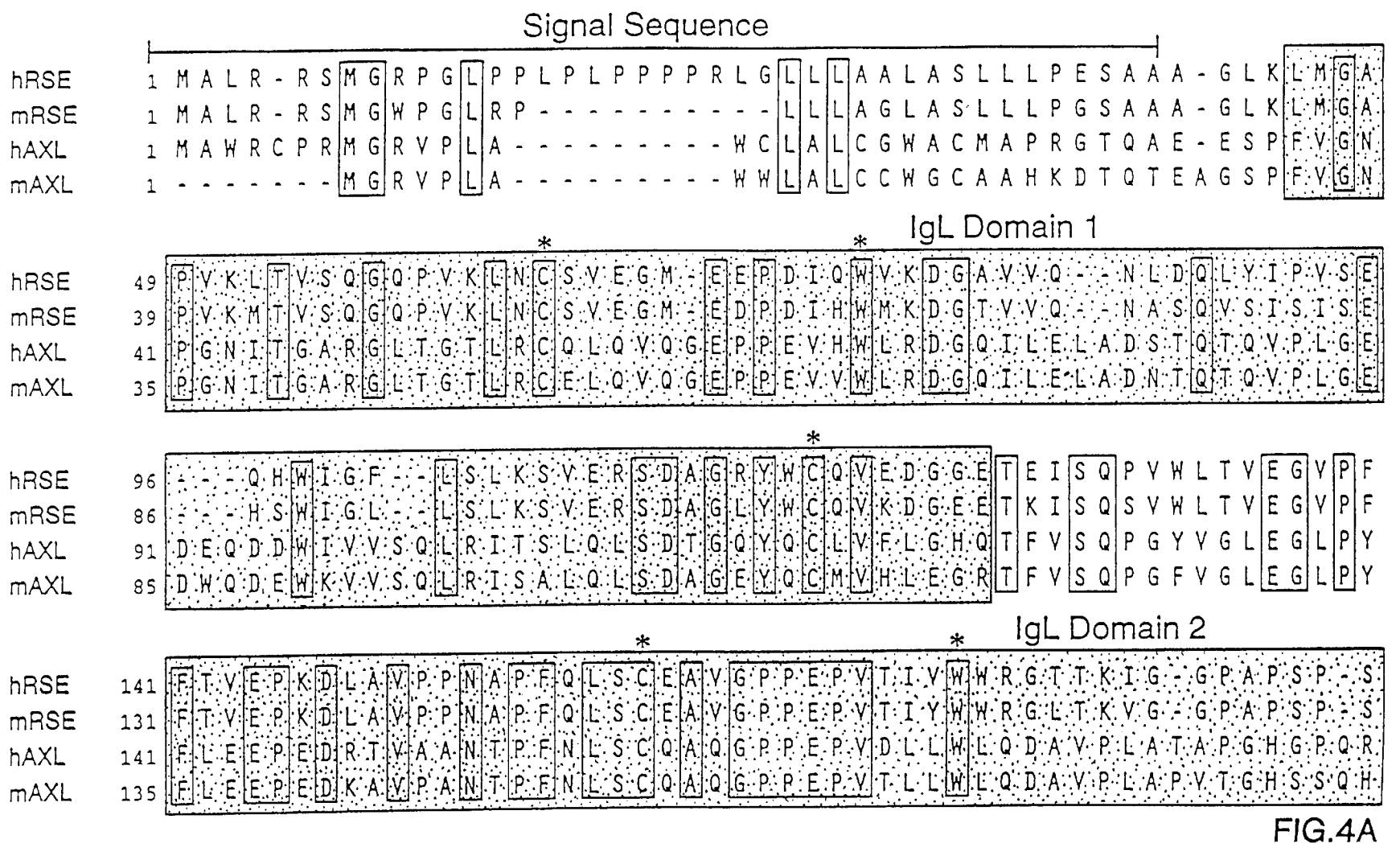
Figure 4B:
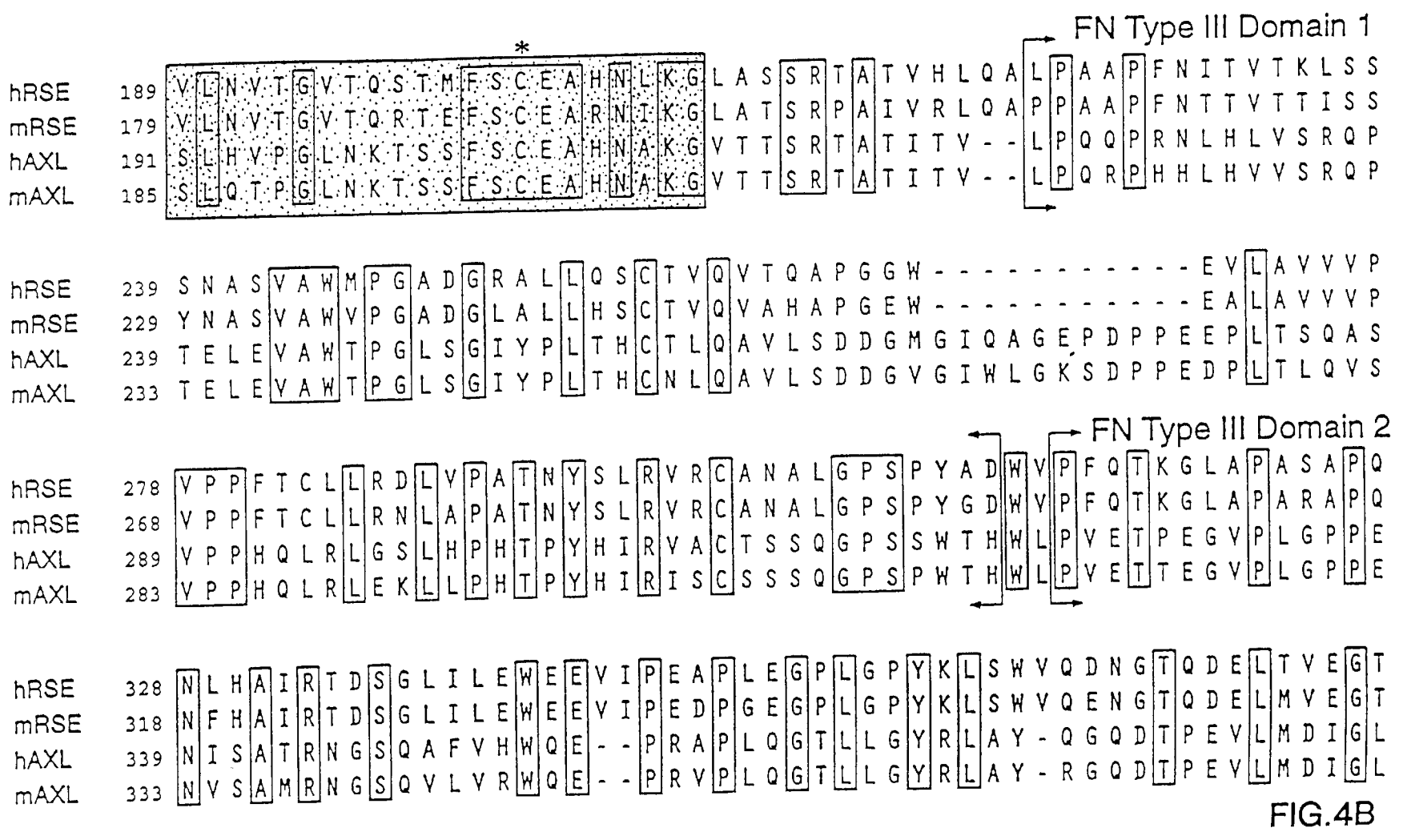
Figure 4C:
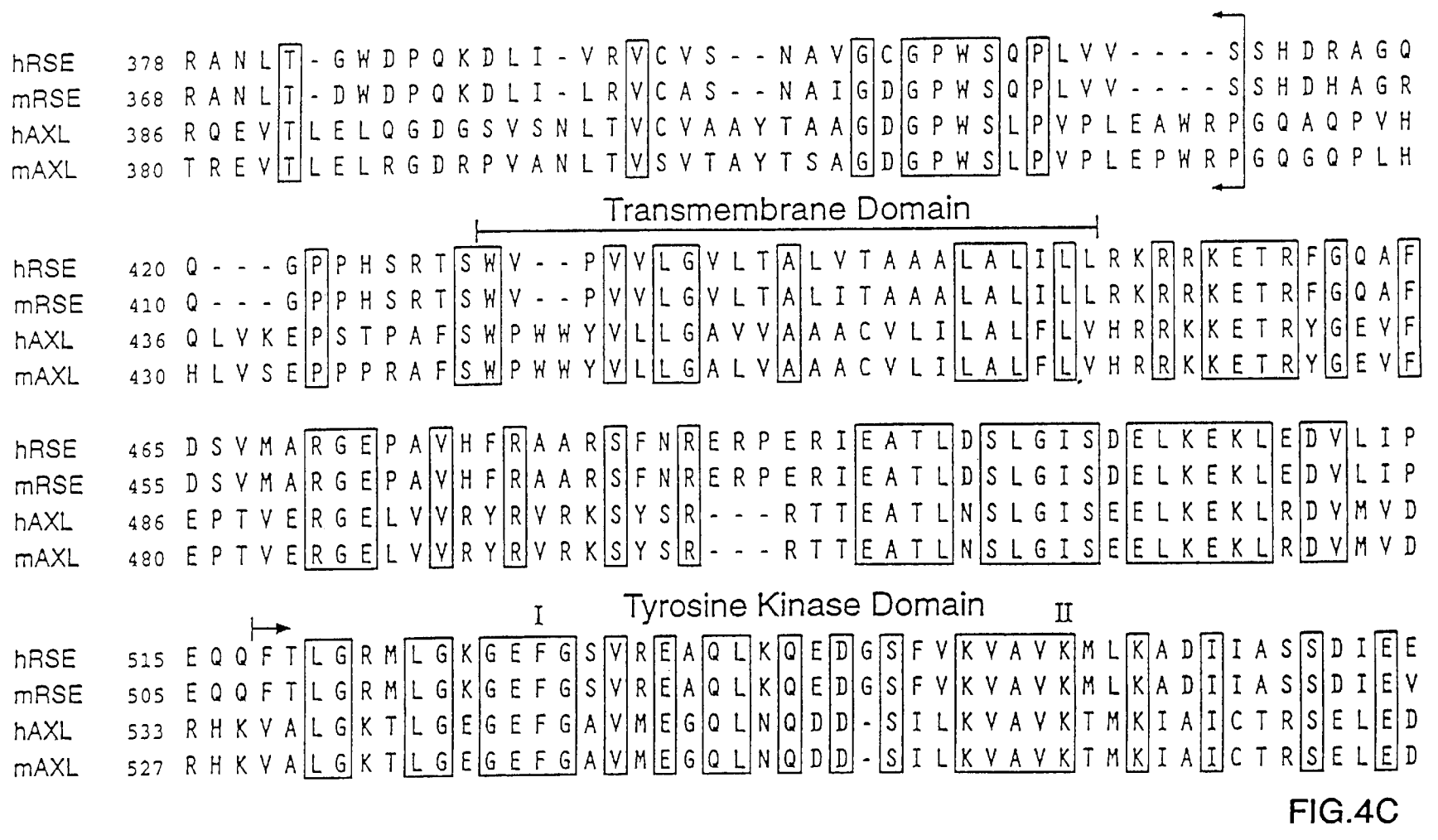

The assembled nucleotide and deduced amino acid sequences of human Rse are shown in FIG. 1A. The Rse cDNA sequence contains an open reading frame of 890 amino acids with two in-frame potential initiation codons (Kozak, M., *J. Cell Biol.* 115: 887–903 [1991]). The first of these methionine codons precedes a hydrophobic region encoding a putative signal sequence of 40 amino acids (FIGS. 1A and 4). A second hydrophobic region is located between amino acids 429–451 and may serve as a transmembrane domain (FIG. 4). This putative transmembrane region is followed by 5 basic amino acids that are characteristic of a stop transfer sequence. Thus, the mature form of human Rse is predicted to contain an ECD of 388 amino acids and an ICD of 439 amino acids. The human Rse cDNA was used as a basis to obtain overlapping clones encoding murine Rse cDNA from a murine brain cDNA library. The assembled nucleotide and deduced amino acid sequences are shown in FIG. 1B. The murine Rse cDNA sequence contains an open reading frame of 880 amino acids. Murine Rse contains a potential signal sequence of 30 amino acids, and a hydrophobic region between amino acids 419 and 441 that may encode a transmembrane domain (FIGS. 1B and 4). The overall amino acid sequence identity of murine and human Rse is 90%, with a sequence identity of 85% in the ECD and 93% in the ICD. Human and murine Rse contain significant homology in the ICD with a number of proteins. Amino acids 650–703 of murine Rse matched the partial rat Tyro-3 sequence in 54 out of 54 positions (Lai et al., supra); human Rse contains a single amino acid difference with rat Tyro-3; $Q^{712}$ of human Rse is replaced with H in the rat sequence. Tyro-3 expression was detected at high levels in the rat brain, and in several other tissues that were examined. In situ hybridization studies show that Tyro-3 is expressed in a highly restricted pattern within the brain, with strong hybridization seen in the CA1 field but little hybridization observed in the CA2, CA3 or CA4 fields of the hippocampus (Lai et al., supra).

The expression of Rse in murine brain samples was also analyzed, using a probe from the ECD portion of the murine cDNA to reduce the possibility of cross-hybridization with mRNAs encoding other protein tyrosine kinases. An identical pattern of hybridization for murine Rse in the hippocampus as that previously reported for Tyro-3 was detected.

Taken together, these results indicate that Tyro-3 encodes a portion of the rat homologue of Rse. In the tyrosine kinase domain, human Rse was most similar to the human rPTKs Axl (64%), hepatocyte growth factor (HGF) receptor (45%), insulin receptor (43%), insulin-like growth factor I (IGF-I) receptor (42%) and Ros (42%) [O'Bryan, J. P., *Mol. Cell. Biol.* 11: 5016–5031 (1991); Janssen, J. W. G., et al., *Oncogene* 6:2113–2120 (1991); Park M., et al., *Proc. Natl. Acad. Sci.* 84: 6379–6383 (1987); Ullrich, A., et al., *Nature* 313: 756–761 (1985); Ullrich, A., et al., *EMBO J.* 5: 2503–2512 (1986); and Birchmeier, C., et al., *Mol. Cell. Biol.* 6: 3109–3116 (1986)]. Human and murine Rse contain a consensus site for $Mg^{2+}$-ATP binding ($GxGxxG(x)_{15-20}AxKxM$) beginning at amino acids 525 and 515, respectively, and a second site, IHRDLAARN (SEQ ID NO: 21), beginning at amino acids 652 and 642, respectively. These sites are characteristic of protein tyrosine kinases (Hanks, et al., supra). The ECD of Rse contains 35% sequence identity with human Axl, which contains two immunoglobulin-like (IgL) repeats followed by two fibronectin type III (FNIII) repeats (FIG. 4). The conserved cysteine and tryptophan residues that are characteristic of IgL domains are present in human and murine Rse (FIG. 4). These features indicate that Axl and Rse share a similar organization of structural domains in the ECD, and that Rse represents the second member of the Axl family of rPTKs. It is noted that Axl contains a unique sequence in the tyrosine kinase domain (KWIAIE (SEQ ID NO: 22)) that has been used to distinguish it from other kinases [(K/T)W (T/M)APE (SEQ ID NO: 23)]. In this same position, Rse contains the sequence [KWLALE (SEQ ID NO: 24)] which is similar to Axl, but more similar to the HGFr (KWMALE (SEQ ID NO: 25)).

A distinguishing feature of the Axl/Rse family of rPTKs is the unique juxtaposition of IgL and FN-type III domains in the ECD. Axl and Rse contain two membrane distal IgL repeats and two membrane proximal FN-type III repeats. The amino acid identity of human Axl and Rse in the first and second IgL repeats is 33% and 58% respectively, and 36% and 42% in first and second FN-type III domains, respectively. A similar level of amino acid identity is observed in comparison of the murine Axl and Rse IgL and FNIII domains. Without being limited to any one theory, it is believed that the combination of IgL and FNIII domains in the ECD of Rse may suggest that this protein plays a role in cellular adhesion. Cell adhesion molecules are grouped into either the immunoglobulin superfamily or the cadherin family based on homology and analysis of binding properties. The cadherins mediate cell-cell adhesion in a calcium dependent manner (Takeichi et al., *Annu. Rev. Biochem.*, 59: 237–252 [1990]). Cadherins associate with the actin cytoskeleton through their intracellular domains via bridging proteins termed catenins (Ozawa et al., *EMBO J.*, 8: [1989]). Cell adhesion mediated by members of the immunoglobulin superfamily is calcium-independent.

Recently, the rPTK Dtrk (Pulido et al., *EMBO J.*, 11:391–304 [1992]), and the receptor protein phosphatase rPTPµ A have been shown to promote cell adhesion in a calcium-independent homophilic manner (Brady-Kalnay et al., *J. Cell. Biol.*, 122: 961–972 [1993]). Brady-Kalnay et al. have suggested that a ligand for rPTPµ A may be the ECD of the same type of receptor on an adjacent cell. The interaction of the ECDs is not dependent on, nor appears to affect the properties of, the phosphatase activity of the receptor. The ECDs of human and murine Rse contain multiple consensus sites for N-linked glycosylation (NxS/T), suggesting that Rse is glycosylated (FIGS. 1A and 1B).

B. Construction of Cell Lines Expressing gD-Rse

To facilitate the analysis of the Rse protein, an epitope-tagged version (referred to herein as gD-Rse) was constructed. The coding sequence for the 40 amino acid signal sequence of Rse was replaced with a sequence encoding amino acids 1–53 of the herpes simplex virus type I (HSV I) glycoprotein D (gD) [Lasky, L. A., et al., *DNA* 3: 23–29 (1984); and Paborsky, L. R. et al. *Pro. Eng.* 3: 547–553 (1990)]. Amino acids 1–25 encode the signal sequence of gD while amino acids 26–56 contain an epitope for the monoclonal antibody 5B6. Oligos (5'-CAGCTGCTCGAGGCAGGTCTGAAGCTCATG (SEQ ID NO: 26), and 5'-GCATGAATTCATGGCACACCTTCTACCGTG (SEQ ID NO: 27)) were used to add a Xho I site to the human Rse cDNA by PCR. The gD-Rse cDNA was inserted into the CMV-based expression vector pRK5 (Suva, L. J et al., *Science*, 237: 893–896 [1987]). NIH3T3 cells were transfected with the gD-Rse expression vector and the vector pCMV-Neo using a modified CaPO4 protocol (Gorman, C., *DNA Cloning: A Practical Approach*, vol II:.143–190, Glover, D. M., ed, IRL Press, Washington D.C. [1985]). After 9 days, individual G418 resistant clones were picked and expanded.

Figure 5:
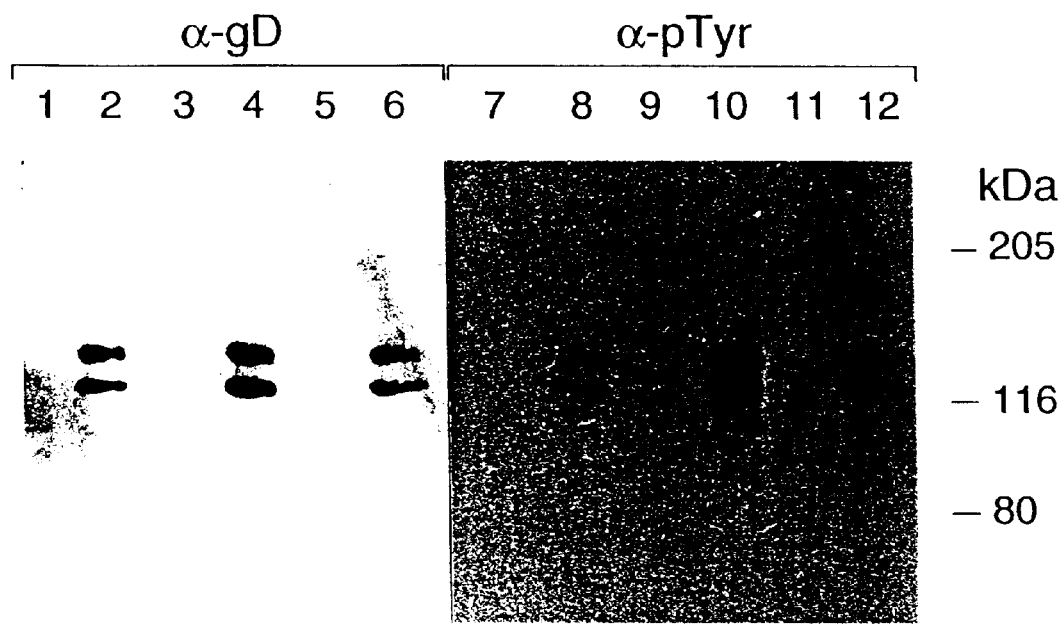
FIG. 5 illustrates expression and activation of gD-Rse. Total lysates from NIH3T3 cells (lanes 1, 3, 5, 7, 9, and 11) or 3T3. gD.R11 cells (lanes 2, 4, 6, 8, 10, and 12) were immunoprecipitated with the antibody 5B6 which detects the gD portion of the fusion protein, and the immunoprecipitates were resolved by SDS-PAGE and immunoblotted with anti-phosphotyrosine antibodies (lanes 7–12). After the blots were developed, they were stripped and re-probed with antibody 5B6 (lanes 1–6). Lysates were prepared from cells grown in the absence of added antibody (lanes 1, 2, 7, and 8) or incubated with antibody 5B6 (lanes 3, 4, 9, and 10) or an isotype-matched control antibody A3.1.2 (lanes 5, 6, 11, and 12). Molecular masses (kDa) are indicated on the right.

To identify clones expressing gD-Rse, the anti-gD monoclonal antibody 5B6 was used to immunoprecipitate proteins from lysates prepared from candidate clones. Immunoprecipitates were fractionated on a 7% SDS-polyacrylamide gel under reducing conditions, and Western blots prepared from the gels were probed with the 5B6 antibody. A stable clone, 3T3. gD.R11, was isolated that expressed novel proteins of 120 kDa and 140 kDa that were reactive with 5B6 and not expressed in the parental 3T3 cells (FIG. 5, lanes 1 and 2). The predicted molecular weight of gD-Rse is approximately 96 kDa. The ECD of human Rse contains 7 potential sites for N-linked glycosylation, and is glycosylated. Thus, while not being limited to any one theory, it is possible that the 120 kDa and 140 kDa forms represent different glycoforms of gD-Rse. Alternatively, the 120 kDa form may represent a proteolytically processed form of gD-Rse. Fluorescence activated cell sorting using the anti-gD monoclonal antibody 5B6 confirmed the presence of the gD epitope at the cell membrane.

C. Analysis of Tyrosine Kinase Activity of gD-Rse

The generally accepted mechanism by which ligands activate rPTKs involves ligand induced dimerization (Schlessinger, J., and Ullrich, A., *Neuron* 9: 383–391 [1992]; Ullrich, A., and Schlessinger, J., *Cell* 61: 203–212 [1990]; and Pazin, M. J., and Williams, L. T. *TIBS* 17: 374–378 [1992]). In some cases, rPTKs can be activated by antibodies directed to the receptor ECD (Yarden, Y. *Proc. Natl. Acad. Sci. U.S.A.* 87: 2569–2573 [1990]; McClain, D. A. *J. Biol. Chem.* 265: 21363–21367 [1990] and Sarup, J. C., *Growth Regul.* 1: 72–82 [1991]). It is believed that these bivalent antibodies mimic ligand-induced activation by promoting receptor oligomerization. It was determined if an antibody (i.e., monoclonal antibody 5B6) to the epitope tag of gD-Rse could function as an agonist. Serum starved 3T3.gD.R11 or control NIH3T3 cells were exposed to 5B6 monoclonal antibody, or a control antibody, for 10 minutes. Using an anti-phosphotyrosine antibody (5E2) to probe Western blots of immunoprecipitated lysates, an increase in phosphorylation of the 140 kDa form of gD-Rse in 3T3.gD.R11 cells treated with 5B6 was clearly detected (FIG. 5, lanes 8 and 10). NIH3T3 cells and 3T3. gD.R11 cells were plated at a density of $2 \times 10^6$ cells per 60 mm dish in DMEM:F-12 (50:50)+10% FBS+glutamine+G418 media. After 16 hours, the media was replaced with serum-free media for 2 hours, and then antibodies were added at a concentration of 500 ng/ml. Cells were harvested, lysates were immunoprecipitated with the 5B6 antibody, fractionated by SDS-PAGE, and Western blots were probed with the indicated antibodies as described (Lokker, N. A. et al., *EMBO* 11:2503–2510 [1992]).

Figure 6:
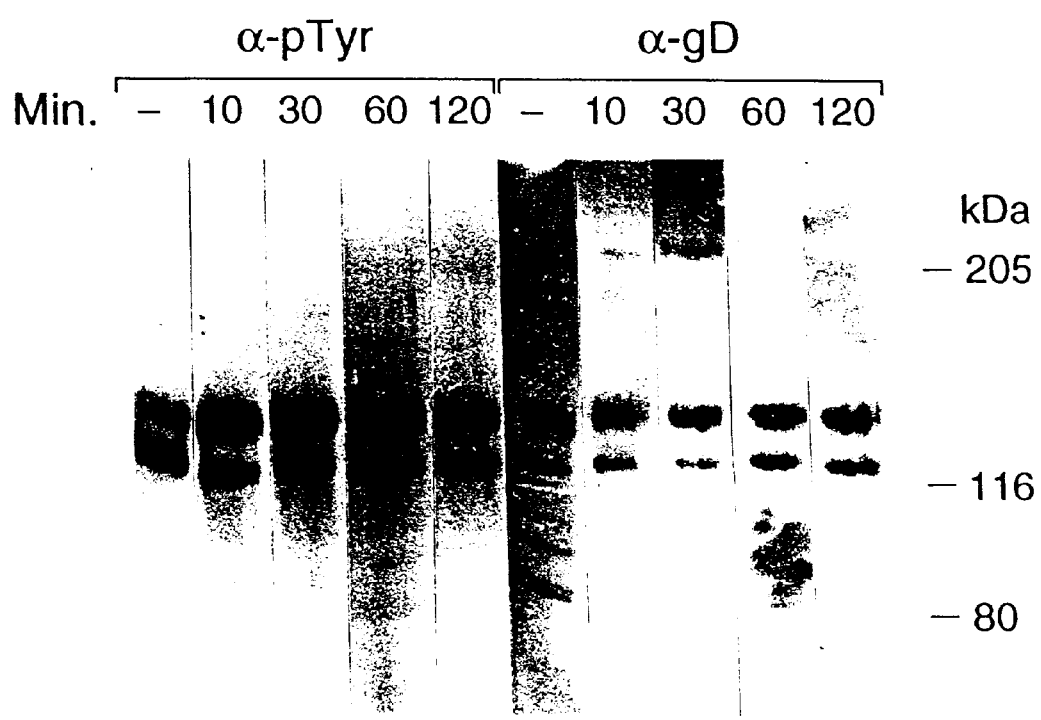
FIG. 6 depicts a time course of antibody induced stimulation of gD-Rse tyrosine kinase activity. 3T3. gD.R11 cells were incubated without (–) or with antibody 5B6 for 10, 30, 60, or 120 minutes (Min.) as indicated. Western blots were prepared as described for FIG. 5. The blot was reacted first with the anti-phosphotyrosine antibody 5E2 (α-pTyr) then stripped and reacted with antibody 5B6 (α-gD) to control for the amount of gD-Rse on the blots.

As discussed below, only minor differences in phosphorylation of the 120 kDa band were observed following treatment of 3T3.gD.R11 cells with 5B6 antibody. The amount of phosphorylation of the 140 kDa band was not affected by treatment of 3T3.gD.R11 cells with control antibody (FIG. 5, lane 12). As an additional control, the blots were stripped and reprobed with the 5B6 monoclonal antibody to show that the amount of gD-Rse loaded on the gel was similar (FIG. 5, lanes 2, 4, and 6). As expected, the increased phosphorylation of the 140 kDa gD-Rse protein was not observed in control NIH3T3 cells treated with either the 56 or control antibody (FIG. 5, lanes 7, 9, and 11). Thus, it was concluded that the tyrosine kinase domain of Rse is functional and that it can be regulated by receptor oligomerization. A time course experiment showed that the kinetics of antibody-induced autophosphorylation were similar to those observed with other rPTKs; induction was observed within 10 minutes, and declined gradually over the next 1–2 hours (FIG. 6). These results indicate that dimerization of the Rse receptor is sufficient to induce intrinsic tyrosine kinase activity. Considerably less antibody-induced autophosphorylation of the 120 kDa form of gD-Rse than of the 140 kDa form was detected (FIGS. 5 and 6). Both forms are expressed at similar levels in the 3T3.gD.R11 cells, and both contain the gD epitope. There are a number of potential explanations for this observation. For example, without being limited to any one theory, the 120 kDa gD-Rse might not be localized to the cell membrane. FACS analysis suggests that at least a portion of the gD-epitope is localized at the cell surface. However, these studies do not distinguish the relative ratios of the 120 kDa and 140 kDa forms at the membrane.

D. Northern Analysis

The expression of Rse was characterized using Northern blot hybridization of polyadenylated RNA isolated from human tissues. A fragment from the portion of the cDNA encoding the ECD was used as a probe to minimize the possibility of cross-reaction with other tyrosine kinases. The human Rse probe was a 485 bp Pst I fragment corresponding to nucleotides 195–680 (FIG. 1A). Northern blots containing 2 µg of polyadenylated RNA from various human tissues or cell lines were hybridized with random-primed probes, washed and exposed according to conditions as described by the manufacturer Clontech, Palo Alto. The RNA blot shown in FIG. 7 was purchased from Clontech, Palo Alto, Calif. As a control for integrity of the RNA, the blots were stripped and reprobed with a 2 Kb human b-actin DNA fragment (Clontech, Palo Alto Calif.). The probe detected a single predominant band of approximately 4.0 Kb (FIG. 7A). The highest amount of hybridization was detected in samples of RNA from the brain and kidney, with lower expression observed in breast, heart, placenta, liver, lung, skeletal muscle, and pancreas. Probing the same blot with a control human b-actin cDNA confirmed the integrity of the RNA in all of the samples (FIG. 7B). In other human tissues that were examined, Rse was expressed at high levels in the breast and at low levels in the adrenal gland and the large and small intestine. See Table 2 below.

TABLE 2

Expression of Rse mRNA in Human Tissues and Cell Lines

| Tissue | Expression Level[a] |
|---|---|
| Breast | +++ |
| Adrenal | + |
| Large Intestine | + |
| Small Intestine | + |
| Cell Line | |
| CMK11-5 | ++ |
| DAMI | ++ |
| THP-1 | − |
| Hep 3B | +++ |
| RAJI | − |
| K562 | + |
| MCF 7 | + |
| U937 | + |

[a]Expression quantitated as follows: (+++) = highest; (++) = moderate; (+) = weak, (−) = below limits of detection.

The expression of Rse in various human cell lines was also analyzed. Little, or no, Rse mRNA was detected by Northern blotting of mRNA samples from the monocyte cell line THP-1 or the lymphoblast-like RAJI cells (Table 2). However, the Rse transcript was detected in a number of hematopoietic cell lines, including cells of the myeloid (i.e., myelogenous leukemia line K562 and myelomonocytic U937 cells) and the megakaryocytic leukemia lines DAMI and CMK11-5, and the human breast carcinoma cell line MCF-7. In the cell lines examined, the highest level of expression was observed in Hep 3B cells, a human hepatocarcinoma cell line.

E. Chromosomal Localization of Human Rse Gene

Primers corresponding to unique regions in the 3' end of the Rse gene were used to amplify human DNAs present in a panel of human-CHO hybrid cell lines (FIG. 8). Chromosomal localization was performed using two sets of primer pairs (Btk 3-1$^{2724}$: 5'-CACTGAGCTGGCTGACTAAG (SEQ ID NO: 28), Btk 3-4: 5'-CCTGATAGGCTGGGTACTCC (SEQ ID NO: 29); Btk 3-2$^{2815}$: 5'-AAGCCCGGACTGACCAAA (SEQ ID NO: 30), Btk 3-3: 5'-GTGCGGAATCAGAAAGATGG (SEQ ID NO: 31)) derived from unique sequence in the 3'-untranslated region of RSE, amplifying DNA from a panel of 25 human-hamster hybrid cell lines containing full complement of the human genome (BIOS, New Haven, Conn.). PCR was performed with 250 ng DNA and 50 pmol each of the 5' and 3' primers, 50 mM KCl, 1.5 mM MgCl$_2$, 20 μg/ml gelatin, 0.2 mM dNTPs and 2.5 units Taq polymerase in a final volume of 100 μl. Cycles of 94° C. for 30 sec, 60° C. for 30 sec and 72° C. for 30 sec were repeated 30 times. A portion of each sample (15 μl) was electrophoresed through a 1.5% agarose gel and either visualized by ethidium bromide staining or transferred to a nylon membrane and hybridized to a $^{32}$P-labeled Rse insert probe prior to 5 hour autoradiography. Positives were scored and compared to a matrix summary of human chromosomal material present in each of the somatic cell hybrid, human control or hamster control DNAs. This analysis localized the Rse gene to human chromosome 15.

F. Construction of Human Rse-IgG Fusion Protein

The coding sequence of the ECD of Rse was fused to that of the human IgG-γ1 heavy chain in a multi-step process. PCR was used to generate a fragment with a unique BstEII site 3' to the coding sequences of the Rse amino acid 428. The 5' primer ( 5'-TCAAGACAATGGAACCCA (SEQ ID NO: 32)) and the 3' primer (5'-CATGGAATTCGGTGACCGATGTGCGGCT-GTGAGGAG (SEQ ID NO: 33)) were used in a 100 μl reaction containing 20 mM Tris-HCl, pH 8.2, 10 mM KCl, 6 mM (NH$_4$)$_2$SO$_4$, 1.5 mM MgCl$_2$, 0.1% Triton X-100, 200 dNTPs and 1 U of Pfu DNA polymerase (Stratagene) and 50 pmol each of the forward primer and the reverse primer and 40 ng of pBS.bptk3.9, which contains a Rse cDNA insert containing most of the extracellular domain, as template. After thirty cycles of denaturation (95° C., 1 min), annealing (55° C., 30 secs) and extension (72° C., 1 min), the PCR product was purified using Geneclean (Bio101), digested with BamHI and BstEII and recovered from low-melting temperature agarose gels. The PCR product was joined to the human IgG-γ$_1$ heavy chain cDNA through a unique BstEII site in that construct (Mark et al., J. Cell. Biol., 267: 26166–26171 [1992]). The resulting construct (termed pRK.bpTK3.IgG.Fusion) contained the coding sequences for amino acids 375–428 of Rse joined to those encoding human IgG-γ$_1$ heavy chain. The remaining portion of the Rse ECD (amino acids 1–374) was then added by linkage through the Bam HI site in pRK.bpTK3.IgG.Fusion to yield pRK.Rse.IgG. Sequencing of the construct was carried out as described above.

G. Establishment of Stable Cell Populations Expressing Rse-IgG

For stable populations, the cDNA encoding Rse-IgG was subcloned into the episomal CMV-driven expression plasmid pCIS.EBON, a pRK5 derivative disclosed in Cachianes et al., Bio. Techniques, 15: 225–259 (1993), the disclosure of which is expressly incorporated herein by reference. Human fetal kidney 293 cells (obtained from ATCC, 12301 Parklawn Drive, Rockville, Md., USA) were transfected by the calcium phosphate technique. Cell monolayers were incubated for four hours in the presence of the DNA precipitate, glycerol shocked, and cultured in F12: DMEM (1:1) containing 2 mM glutamine, 10% fetal bovine serum, penicillin and streptomycin. After 48 hours, populations were replated in media containing G418 to select for a stable population of cells. Conditioned media was collected from cells expressing Rse-IgG that had been cultured in serum-free media for 72 hours in the absence of G418.

H. Analysis of Rse-IgG by Western Blotting

For the Western blot analysis, 72-hour conditioned media from transfected 293 cells was subjected to electrophoresis under reducing conditions on a 7% SDS-acrylamide gel. The gel was blotted onto nitrocellulose with a Pharmacia LKB Novablot Western transfer apparatus. The filter was blocked in 1×NET (150 mM NaCl, 5 mM EDTA, 50 mM Tris-OH, pH 7.5, 0.05% Triton-X 100) with 0.25% gelatin overnight at room temperature and then incubated with an HRP-conjugated antibody to the human IgG Fc (ICN). The Western blot was developed by a chemiluminescent detection system as described by the manufacturer (Amersham).

I. Purification and Analysis of Rse-IgG

Rse-IgG was purified by affinity chromatography on a protein A column using procedures as described by Chamow, S. M., et al., *Biochemistry*, 29:9885–9891 (1990) with the following minor modifications. Conditioned media collected from cells expressing the Rse-IgG was adjusted to 0.1 M citrate pH 6.0 and loaded directly onto a protein A column (Repligen). The column was washed with 0.1 M citrate, pH 6.0, and was eluted with 3 M $MgCl_2$ with 10% glycerol. Fractions were pooled and desalted on a PD-10 column, dialyzed and concentrated against PBS. Protein concentrations were determined by an ELISA against human IgG (Fc). The protein was analyzed for purity by Coomassie staining of PAGE gels.

J. Generation of Rabbit Polyclonal Antisera Against Rse-IgG

Polyclonal antibodies were generated in New Zealand White rabbits against Rse-IgG. 4 μg in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93, 3–12 [1983]). For subsequent boosts, the protein was injected into subcutaneous and intramuscular sites. 1.3 μg protein/kg body weight was injected every 3 weeks with bleeds taken 1 and 2 weeks following each boost.

K. Stimulation of 3T3.gD.R11 Cells with Anti-Rse-IgG Polyclonal Antisera

Figure 9:
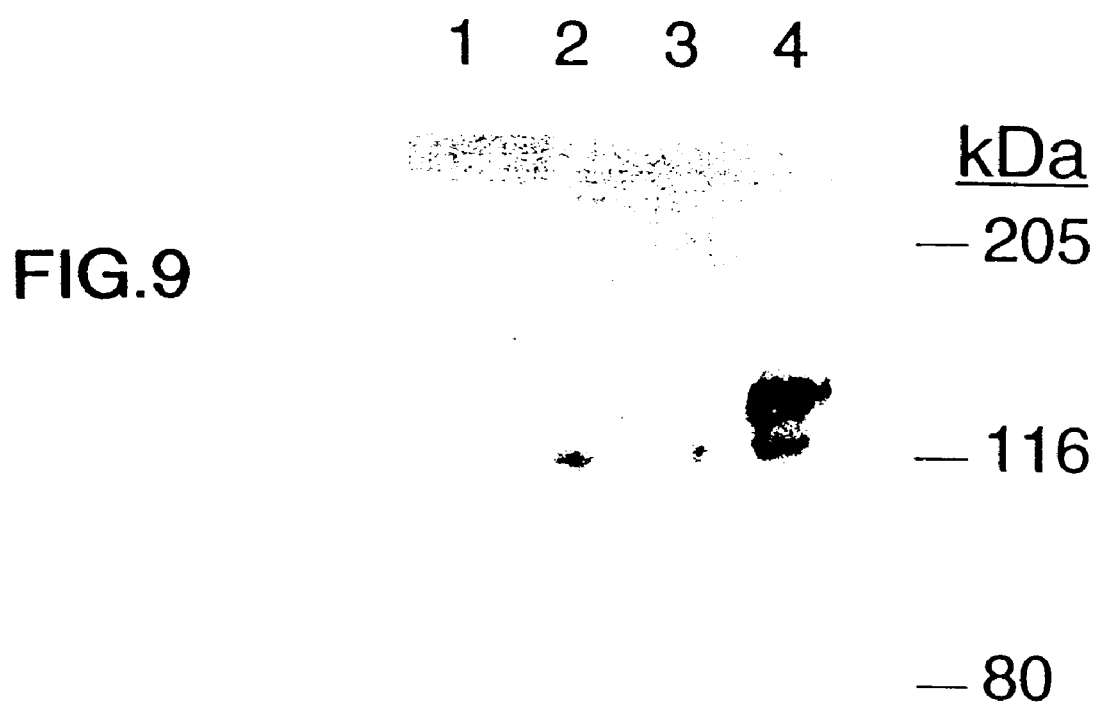
FIG. 9 depicts stimulation of gD-Rse by polyclonal antibodies. Immunoprecipitates from control NIH3T3 cells (lanes 1 and 3) or 3T3. gD.R11 cells (2 and 4) were prepared using the anti-gD antibody 5B6, resolved by SDS-PAGE and immunoblotted with antiphosphotyrosine antibodies. Cells were either untreated (lanes 1 and 2) or treated (lanes 3 and 4) for 10 minutes with rabbit polyclonal antiserum prepared against a fusion protein containing the extracellular domain of Rse.

Serum starved 3T3.gD.R11 cells or NIH3T3 cells were exposed to pre-immune serum or polyclonal antisera directed against Rse-IgG at a 1/200 dilution for 10 minutes. The gD-Rse protein was immunoprecipitated from extracts using the anti-gD monoclonal antibody 5B6, as described above in section B. Proteins were fractionated on a 7% SDS-PAGE under reducing conditions and transferred to nitrocellulose. Phosphoproteins were detected with the anti-phosphotyrosine antibody 5E2, as described in section C above. The results are depicted in FIG. 9. As can be seen in the figure, treatment of the 3T3.gD.R11 cells with anti-Rse ECD antisera stimulated the phosphorylation of the 140 kDa gD-Rse protein (lane 4). This increase was not observed in cells treated with pre-immune sera.

L. Deposit of Materials

The following *E. coli* host cells containing plasmid DNA encoding hRse have been deposited with the American Type Culture Collection, 12301 Parklawn Drive, Rockville, Md., USA (ATCC):

| Host Cells | ATCC Accession No. | Deposit Date |
| --- | --- | --- |
| *E. coli* strain 294 | 69519 | Dec. 15, 1993 |

This deposit was made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. The deposited DNA will be made available by ATCC under the terms of the Budapest Treaty, and subject to an agreement between Genentech, Inc. and ATCC, which assures permanent and unrestricted availability of the deposited DNA to the public upon issuance of the pertinent U.S. patent or upon laying open to the public of any U.S. or foreign patent application, whichever comes first, and assures availability of the deposited DNA to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited DNA should be lost or destroyed, it will be promptly replaced on notification with a specimen of the same DNA. Availability of the deposited DNA is not to be construed as a license to practice the invention in contravention of the rights granted under the authority of any government in accordance with its patent laws.

EXAMPLE 2

Isolation and Characterization of HPTK6

A. cDNA Cloning and Sequencing

Degenerate oligodeoxyribonucleotide primers designed to sequences encoding conserved amino acids in tyrosine kinases were used to isolate a primer which was used to screen a liver carcinoma (Hep 3B) cDNA lambda library (see the procedures set forth in Example 1). Two full length clones encoding HPTK6 were found which differed in their 3' untranslated DNA sequences.

The assembled nucleotide and deduced amino acid sequences of human HPTK6 are shown in FIG. 2. The HPTK6 cDNA sequence contains an open reading frame of 913 amino acids. The mature form of human HPTK6 is predicted to contain an ECD of 417 amino acids (i.e., amino acid residues 19 to 417, shown in FIG. 2) and an ICD of 473 amino acids (i.e., amino acid residues 440 to 913 shown in FIG. 2). The sequence appears to be substantially homologous to the human rPTK called DDR disclosed by Johnson et al., supra, sharing 99.5% overall sequence identity therewith. Similarly, the sequence shared 93.1% overall sequence identity with the rPTK termed NEP, which appears to be the murine equivalent of HPTK6 (see Zerlin et al., supra).

B. Northern Analysis

Figure 10A:
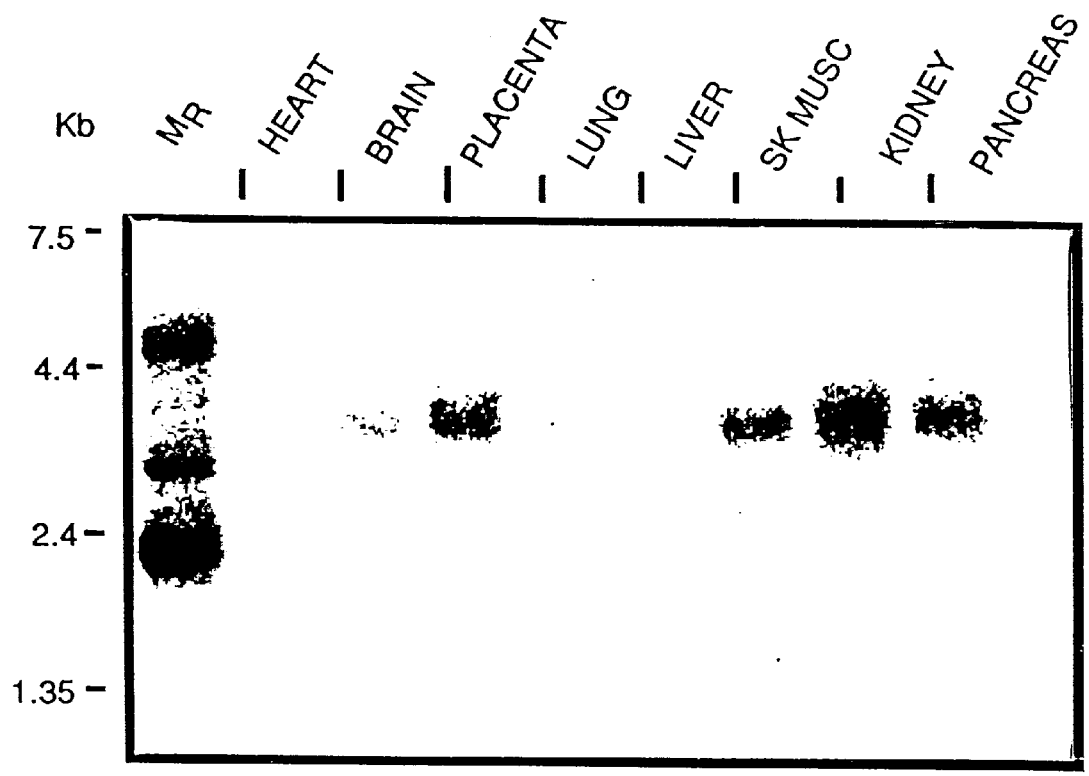
FIGS. 10A and 10B show a Northern blot analysis of HPTK6 mRNA expression in adult (FIGS 10A) and fetal (FIG. 10B) human tissues. A Northern blot containing 2 μg of poly(A) RNA isolated from human tissues was hybridized to a $^{32}$P-labeled probe corresponding to human HPTK6 nucleotides 11–622 (FIG. 2). Positions of markers are indicated on the left in Kb.
Figure 10B:
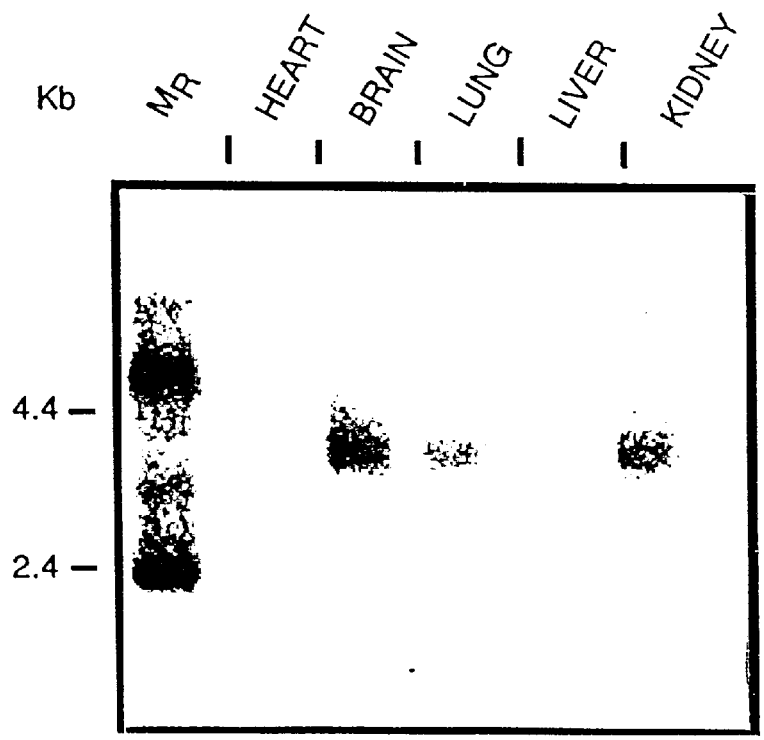

The expression of HPTK6 was characterized via Northern blot hybridization of polyadenylated RNA isolated from human tissues. A 611 base pair fragment from the portion of the cDNA encoding the ECD was used as a probe to minimize the possibility of cross-reaction with other tyrosine kinases. Northern blots containing 2 μg of polyadenylated RNA from various human tissues or cell lines were hybridized with random-primed probes, washed and exposed as described by the manufacturer Clontech, Palo Alto, Calif. The RNA blots shown for human adult and human fetal tissues in FIG. 10 were purchased from Clontech, Palo Alto, Calif. The probe detected a single predominant band of 3.8–3.9 Kb (FIG. 10). In the human adult tissues, the highest amount of hybridization was detected in samples of RNA from the kidney and placenta, with lower expression observed in the brain, lung, skeletal muscle and pancreas. No expression in the liver was detected. See FIG. 10A. Expression of HPTK6 in the fetal tissues was different from expression in the adult tissues. With reference to FIG. 10B, the highest expression was observed in the fetal brain with lower expression evidenced in the fetal kidney and lung tissue, respectively. Like the adult tissue, no expression in the liver was observed. In the adult and fetal tissues studied, the expression of HPTK6 was generally low.

Figure 11A:
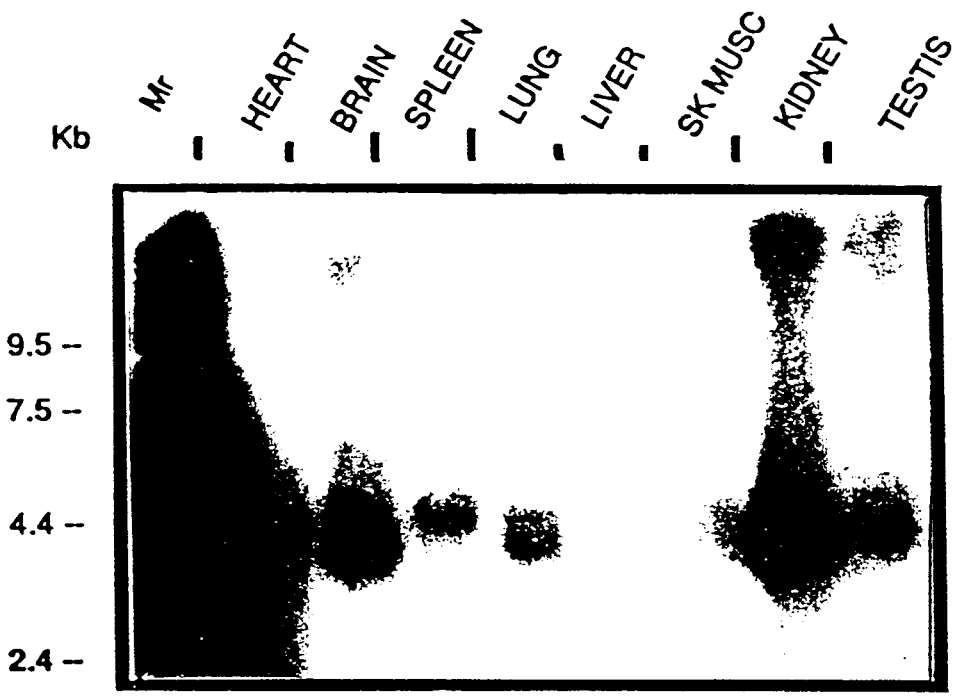
FIGS. 11A and 11B show a Northern blot analysis of HPTK6 mRNA expression in adult mouse tissue.
Figure 11B:
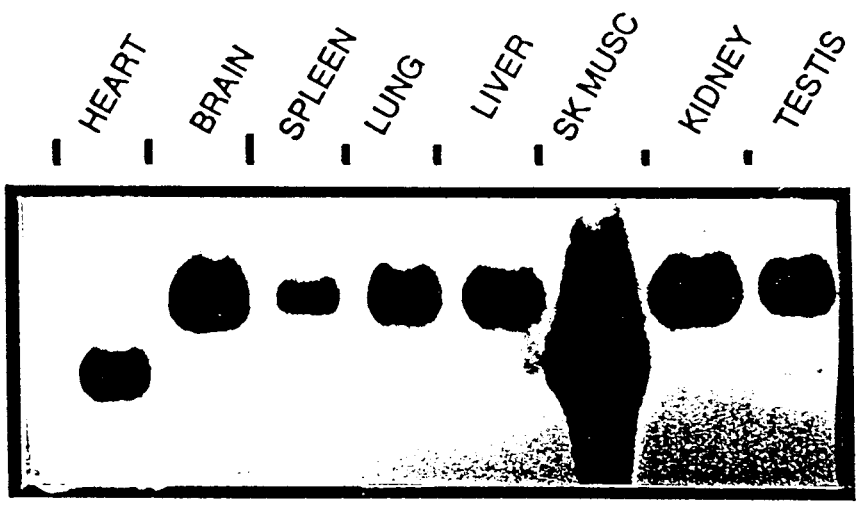

Expression of HPTK6 in murine tissue was also investigated. The RNA blot shown in FIGS. 11A and B was obtained from Clontech, Palo Alto, Calif. As a control for integrity of the RNA, the blots were stripped and reprobed with a 2 Kb human b-actin DNA fragment (Clontech, Palo Alto Calif.), FIG. 11B. Bands of about 4.0 and 4.3 Kb were detected. The highest amount of hybridization was detected in samples of RNA from the kidney and brain, with lower expression observed in the testis, spleen and lung.

Expression of HPTK6 in various cell lines was also studied via Northern blotting of mRNA samples from these cell lines. The results of these experiments are shown in Table 3 below.

TABLE 3

Expression of HPTK6 mRNA in Human Cell Lines

| Cell Line | Expression Level[a] |
|---|---|
| MCF 7 (human breast carcinoma) | ++ |
| Thymoma | ++ |
| Hep 3B (liver carcinoma) | + |
| CMK11-5 (megakaryocyte progenitor) | – |
| DAMI (megakaryocyte progenitor) | – |
| BMMC (bone marrow mononucleocytes) | – |
| PBMC (peripheral blood mononuclear cells) | – |
| Megakaryoblast | – |

[a]Expression quantitated as follows: (++) = highest; (+) = moderate/weak; (–) below limits of detection.

Figure 12C:
FIGS. 12A, 12B, and 12C depict in situ hybridization of HPTK6 in human (FIG. 12A) and mouse (FIGS. 12B and 12C) fetal tissue. Transverse section through human or mouse embryos were hybridized with $^{32}$P-labeled antisense (−ve) and sense (tve) strands.
Figure 12B:
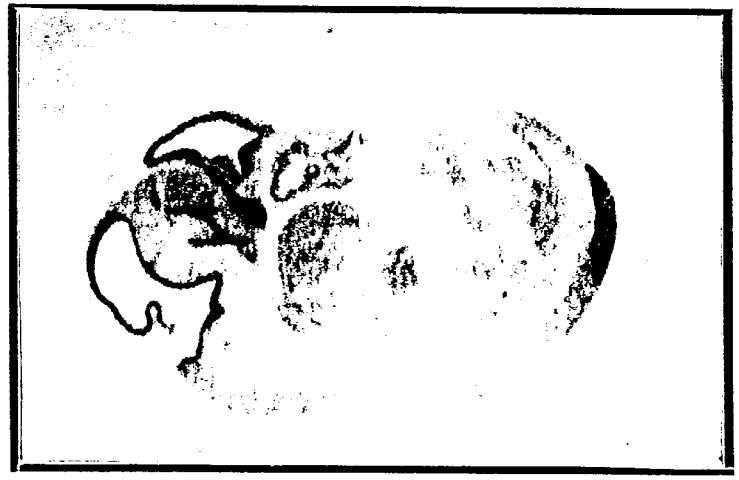
Figure 12A:

In situ hybridization of HPTK6 RNA in deparaffinized sections of human and murine embryos was performed according to Haub & Goldfarb, Development, 112: 396–406 [1991], using $^{35}$S-labeled cRNA riboprobes. DNA fragments from HPTK6 cDNA served as templates for synthesis of sense (+ve) and antisense (–) riboprobes. Hybridized slides were subjected to autoradiography. The traverse sections of human and mouse fetal tissues are shown in FIGS. 12A–C. Antisense riboprobes gave signals, while sense probes gave no signal. As indicated in FIG. 12, high levels of expression were observed in the fetal brain and spinal cord for both the mouse and human.

These results indicate that HPTK6 may play a role in cancer formation in certain cells, e.g., human breast carcinoma cells. Accordingly, antagonist ligands to the receptor may be useful for cancer therapies. The high level of expression in fetal brain indicates that HPTK6, or its ligands, may be useful for treating neurodegenerative diseases as discussed earlier herein.

What is claimed is:

1. An isolated polypeptide, comprising a mammalian receptor protein tyrosine kinase (rPTK) encoded by nucleic acid which hybridizes under stringent conditions to the complement of a nucleic acid sequence encoding an amino acid sequence as set forth in SEQ ID NO:4.

2. A composition comprising the isolated polypeptide of claim 1 and an acceptable carrier.

3. The isolated polypeptide of claim 1 which is human rPTK.

4. The isolated polypeptide of claim 3 comprising an amino acid sequence as set forth in SEQ ID NO:4.

5. The isolated polypeptide of claim 1 which is not associated with naturally occurring glycosylation.

6. The isolated polypeptide of claim 1 which is not glycosylated.

7. An isolated polypeptide, comprising an extracellular domain of mammalian rPTK, wherein the isolated polypeptide is essentially free of transmembrane and intracellular domains of a mammalian rPTK, and is encoded by nucleic acid which hybridizes under stringent conditions to the complement of a nucleic acid encoding an amino acid sequence as set forth in SEQ ID NO:8.

8. A fusion protein comprising amino acid sequence SEQ ID NO:8 and an immunoglobulin chain.

9. The fusion protein of claim 8 wherein the immunoglobulin chain is derived from a human IgG immunoglobulin.

10. The isolated polypeptide of claim 7 which comprises an amino acid sequence as set forth in SEQ ID NO:8.

* * * * *

UNITED STATES PATENT AND TRADEMARK OFFICE
CERTIFICATE OF CORRECTION

PATENT NO.    : 6,087,144
DATED         : July 11, 2000
INVENTOR(S)   : Scadden et al.

Figure 3B:
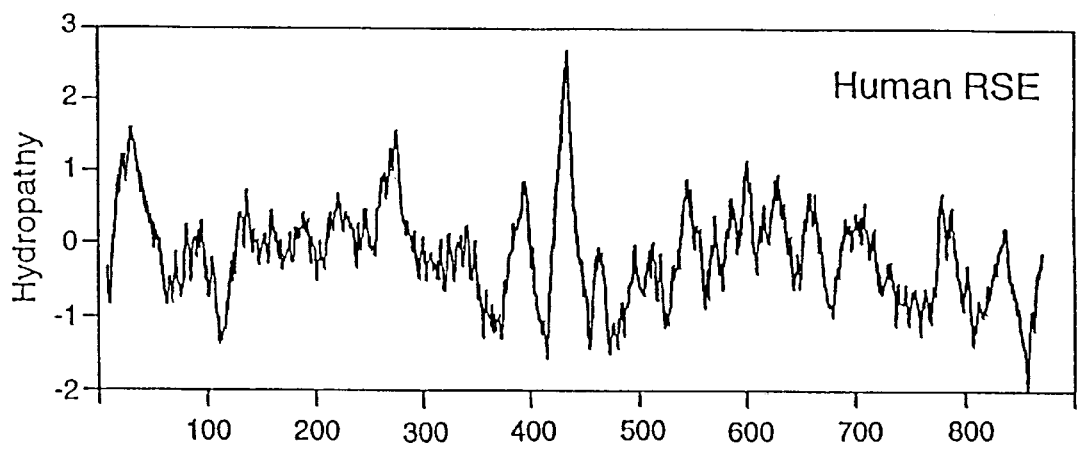
Figure 3C:
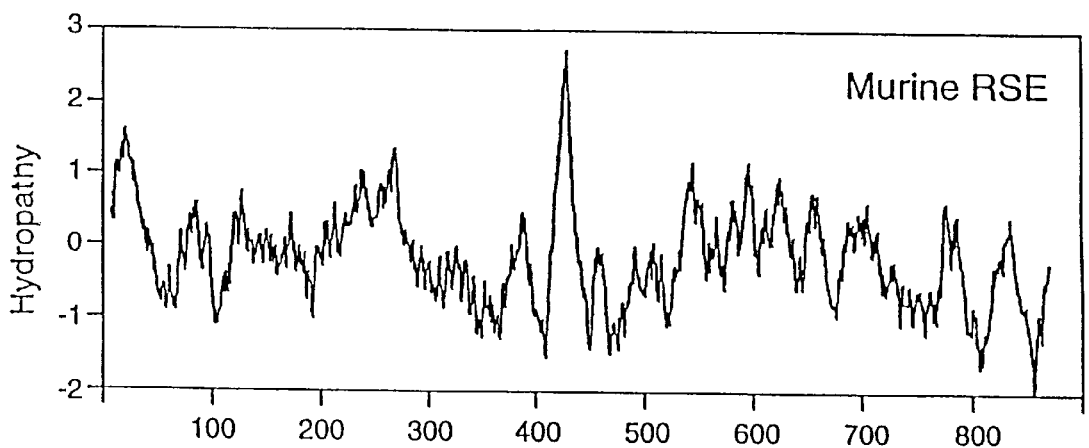
FIG. 3C is shown. The HYDRO program (Genentech, Inc.) was used to obtain the hydrophobicity plots.

It is certified that error appears in the above-identified patent and that said Letters Patent is hereby corrected as shown below:

Column 5,
Line 14, delete "FIG. 1" and insert therefor -- FIG. 1A-C --.
Line 19, delete "FIG. 1B" and insert therefor -- FIG. 1D-F --.
Line 56, delete "FIG. 3" and insert therefor -- FIG. 3A --.

Signed and Sealed this

Eleventh Day of December, 2001

Attest:

NICHOLAS P. GODICI
*Attesting Officer*   *Acting Director of the United States Patent and Trademark Office*